US008853160B2

(12) United States Patent
Greig et al.

(10) Patent No.: US 8,853,160 B2
(45) Date of Patent: *Oct. 7, 2014

(54) GLP-1, EXENDIN-4, PEPTIDE ANALOGS AND USES THEREOF

(75) Inventors: Nigel H. Greig, Phoenix, MD (US); Josephine M. Egan, Baltimore, MD (US); Maire Doyle, Baltimore, MD (US); Harold W. Holloway, Middle River, MD (US); Tracy Perry, Baltimore, MD (US)

(73) Assignee: The United States of America, as represented by the Secretary, Department of Health & Human Services, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/594,313

(22) Filed: Aug. 24, 2012

(65) Prior Publication Data

US 2012/0329715 A1 Dec. 27, 2012

Related U.S. Application Data

(63) Continuation of application No. 12/317,042, filed on Dec. 18, 2008, now Pat. No. 8,278,272, which is a continuation of application No. 10/485,140, filed as application No. PCT/US02/24141 on Jul. 30, 2002, now Pat. No. 7,576,050.

(60) Provisional application No. 60/309,076, filed on Jul. 31, 2001.

(51) Int. Cl.

| *A61K 38/26* | (2006.01) |
| *A61P 3/10* | (2006.01) |
| *A61P 7/12* | (2006.01) |
| *C07K 14/605* | (2006.01) |
| *C07K 14/575* | (2006.01) |
| *A61K 38/00* | (2006.01) |
| *A61K 38/22* | (2006.01) |

(52) U.S. Cl.
CPC ........... *C07K 14/57563* (2013.01); *A61K 38/00* (2013.01); *A61K 38/26* (2013.01); *A61K 38/2278* (2013.01)
USPC ...................................................... 514/11.7

(58) Field of Classification Search
None
See application file for complete search history.

(56) References Cited

U.S. PATENT DOCUMENTS

| 3,710,795 | A | 1/1973 | Higuchi et al. |
| 5,424,286 | A | 6/1995 | Eng |
| 6,268,479 | B1 | 7/2001 | Stern et al. |
| 6,429,197 | B1 * | 8/2002 | Coolidge et al. ............... 514/6.8 |
| 7,157,429 | B1 | 1/2007 | Bachovchin et al. |
| 7,576,050 | B2 * | 8/2009 | Greig et al. ..................... 514/1.1 |
| 7,803,753 | B2 * | 9/2010 | Chu et al. ........................ 514/7.2 |
| 8,278,272 | B2 | 10/2012 | Greig et al. |
| 2002/0115605 | A1 | 8/2002 | During et al. |
| 2003/0004162 | A1 | 1/2003 | Treadway |
| 2003/0050227 | A1 | 3/2003 | Kondo |
| 2004/0018981 | A1 | 1/2004 | Dong |
| 2004/0053370 | A1 * | 3/2004 | Glaesner et al. ............. 435/69.7 |
| 2005/0239854 | A1 | 10/2005 | Sugiyama et al. |

FOREIGN PATENT DOCUMENTS

| AU | 2002317599 B2 | 4/2008 |
| AU | 2008202893 A1 | 7/2008 |
| CA | 2455963 A1 | 2/2003 |
| EP | 0 658 568 A1 | 6/1995 |
| EP | 02748271.0 | 7/2002 |
| EP | 1304121 A1 | 4/2003 |
| JP | 2000-175686 A | 6/2000 |
| JP | 2003-517083 A | 5/2003 |
| WO | 95/31214 A1 | 11/1995 |
| WO | 97/46584 A1 | 12/1997 |
| WO | 98/30231 A1 | 7/1998 |
| WO | 99/038501 A2 | 8/1999 |
| WO | 99/40788 A1 | 8/1999 |
| WO | 99/43705 A1 | 9/1999 |
| WO | 99/46283 A1 | 9/1999 |
| WO | 99/067278 A1 | 12/1999 |
| WO | 00/09666 A2 | 2/2000 |
| WO | 0016797 A2 | 3/2000 |
| WO | 00/34332 A1 | 6/2000 |
| WO | WO-0034331 A2 | 6/2000 |
| WO | WO 0034331 A2 * | 6/2000 |

(Continued)

OTHER PUBLICATIONS

McIntosh et al "The molecular and cellular sequelae of experimental traumatic brain injury: pathogenetic mechanisms" Neuropathology and Appl Neurobiology 24:251-267. Presented Jan. 7, 1998.*

(Continued)

*Primary Examiner* — Maury Audet
*Assistant Examiner* — Zachary J Miknis
(74) *Attorney, Agent, or Firm* — Edwards Wildman Palmer LLP; Peter F. Corless

(57) ABSTRACT

The invention relates to novel polypeptide analogs of GLP-1 and exendin-4. The polypeptide, in a preferred embodiment, is insulinotropic and long-acting. Preferably, the polypeptide's insulinotropic effect is comparable to or exceeds the effect of an equimolar amount of GLP-1 or exendin-4. The invention also relates to a method of treating a subject with diabetes, comprising administering to the subject the polypeptide of the invention in an amount that has an insulinotropic effect. The invention also relates to methods of using GLP-1, exendin-4, and polypeptide analogs thereof for neuroprotective and neurotrophic effects.

20 Claims, 28 Drawing Sheets

(56) References Cited

FOREIGN PATENT DOCUMENTS

| WO | 00/41546 A2 | 7/2000 |
|---|---|---|
| WO | 00/47219 A2 | 8/2000 |
| WO | 00/66142 A2 | 11/2000 |
| WO | 00/69911 A1 | 11/2000 |
| WO | 00/73331 A2 | 12/2000 |
| WO | 01/04156 A1 | 1/2001 |
| WO | 01/51078 A1 | 7/2001 |
| WO | 02/46227 A2 | 6/2002 |

OTHER PUBLICATIONS

Roberston et al "Protection against spinal cord ischemia with insulin-induced hypoglycemia" J Neurosurg 67:739-744. Published 1987.*

Sala et al "Role of glycemia in acute spinal cord injury data from a rat experimental model and clinical experience" Annals of New York Acad Sci 890:133-154. Published Dec. 1999.*

Steinmann and Zamvil "How to Successfully Apply Animal Studies in Experimental Allergic Encephalomyelitis to Research on Multiple Sclerosis" Ann. Neurol. 60:1-12. Published Jun. 26, 2006.*

Sriram and Steiner "Experimental Allergic Encephalomyelitis: A Misleading Model of Multiple Sclerosis" Ann. Neurol. 58:939-945. Published Nov. 28, 2005.*

C. Montrose-Rafizadeh et al., "High Potency Antagonists of the Pancreatic Glucagon-like Peptide-1 Receptor", The Jounal of Biological Chemistry, 272(34), pp. 21201-21206 (1997).

Montrose-Rafizadeh et al., "Incretin Hormones Regulate Glucose-Dependent Insulin Secretion in RIN 1046-38 Cells: Mechanism of Action." Endocrinology 135: 589-594 (1994).

Montrose-Rafizadeh et al., "High Potency Antagonists of the Pancreatic Glucagon-Like Peptide-1 Receptor," J. Biol Chem 272: 21201-21206 (1997).

Montrose-Rafizadeh et al., "Incretin Hormones Regulate Glucose-Dependent Insulin Secretion in RIN 1046-38 Cells: Mechanism of Action," Endocrinology 135: 589-594 (1994).

Montrose-Rafizadeh et al.,"Overexpression of Glucagon-Like Peptide-1 Receptor in an Insulin-Secreting Cell Line Enhances Glucose Responsiveness." Mol. Cell Endocrinol. 130 (1-2): 109-117 (1997).

Montrose-Rafizadeh et al.,"Novel Signal Transduction and Peptide Specificity of Glucagon-Like Peptide Receptor 3T3-L1 Adipocytes." J. Cell Physiol. 172: 275-280 (1997).

Nathan et al., "Insulintropic Action of Glucagonlike Peptide-1-)7-37) in Diabetic and Nondiabetic Subjects," Diabetes Care 15:270-276 (1992).

Nauck et al., "Preserved Incretin Activity of Glucagon-Like Peptide 1 (7-36) But Not of Synthetic Human Gastric Inhibitory Polypeptide in Patients With Type-2 Diabetes Mellitus", J. Clin. Invest. 91:301-307 (1993).

Nauck et al., "Normalization of Fasting Hyperglycaemia by Exogenous Glucagon-Like Peptide1 (7-36 amide) in Type 2 (Non-Insulin Dependent) Diabetic Patients," Diabetpologia 36: 74+-744 (1993).

Naya et al., "Diabetes, Defective Pancreatic Morphogenesis, and Abnormal Enteroendocrine Differentiation in Beta2/NeuroD-Deficient Mice," Genes Dev. 11:2323-2334 (1997).

Noma, "Overexpression of Neurod in PC12 Cells Alters Morphology and Enhances Expression of the Adenylate Kinase Isozyme 1 Gene," Molecular Brain research 67:53-63 (1999).

O'Harte et al., "N-Terminally Modified Glucagon-Like Peptide-1 (7-36) Amide Exhibits Resistance To Enzymatic Degradation While Maintaining Its Antihyperglycaemic Activity In Vivo", Biochim. Biophys. Acta 1474:13-22 (2000).

Oka et al., "Behavorial Studies Indicate a Rold for Glucagon-like Peptide-1 in Memory and Learning in Rat," Society for Neuroscience 25:1862, 742.13 (1999).

J. Oka et al., "Endogenous GLP-1 is involved in b-amyloid protein-induced memory impairment and hippocampal neuronal death in rats", Brain Research, vol. 878, pp. 194-198 (2000).

Oka et al., "Partial Translation of Effect of a GLP-1 on Beta-Amyloid Protein-Induced Memory Impairment and Hippocampal Neuronal Death," The 22nd Annual Meeting of the Japanese Neuroscience Society, Program Abstract, p. 146, I-P-207 (1999).

Okamoto et al., "Treatment of Vascular Dementia", Ann. New York Academy of Science, pp. 5507-5512 (2002).

Orskov, "Glucagon-like peptide-1, a new hormone of the entero-insular axis," Diabetologia 35: 701-711 (1992).

Ott et al., "Diabetes mellitus and the risk of dementia: The Rotterdam Study," Neurology 53: 1937-1942 (1999).

Patel, et al., "Pharmacotherapy of Cognitive Impairment in Alzheimer's Disease: A Review", J. Geriatr. Psychiatry Neurol. vol. 8 pp. 81-95 (1995).

Perfetti et al., "Age-Dependent Reduction on Insulin Secretion and Insulin MRNA in Isolated Islets From Rats." Am. J. Physiol. 269: E983-990 (1995).

Perry et al, "A Novel Neurotrophic Property of Glucagon-Like Peptide1: A Promoter of Nerve Growth Factor-Mediated Differentiation in PC12 Cells," The journal of pharmacology and experimental therapeutics 300 (3): 958-966 (Mar. 2002).

Perry et al., "Behavorial, Histological and Immunocytochemical Consequences Following 192 IgG-Saporin Immunolesions of the Basal Forebrain Cholinergic System," Brain Res. Bull 54:29-48 (2001).

Perry et al, "Evidence of GLP-1 Mediated Neuroprotection in an Animal Model of Pyridoxine-Induced Peripheral Sensory Neuropathy," Experimental Neurology 203:293-301 (2007).

Pinderhuges et al., "Evicence-Based Approach to Management of Feverin Patients With End-Stage Dementia", Ann. New York Academy of Science, pp. 507-412 (2002).

Poewe, W. "The Need for Neuroprotective Therapies in Parkinson's Disease", Neurology 66: s2-29 (2006).

Ritzel et al., "Pharmacokinetic Insulintropic, and Glucagonostatic Properties of GLP-17 (7-36 Amide) After Subcutaneous Injection in Healthy Volunteers. Dose-Response-Relationships," Diabetologia 38: 720-725 (1995).

Robertson, et al., "Protection Against Spinal Cord Ischemia With Insulin Induced Hypoglycemia", J. Neurosurg. 67: 739-744 (1987).

Sala, et al., "Role of Glycemia in Acute Spinal Cord Injury Data From a Rat Experimental Model and Clinical Experience", Annals of New York Academy of Sciences, vol. 890, pp. 133-154 (Dec. 1999).

Sandyk, R., "The Relationship Between Diabetes Mellitus and Parkinson's Disease", International Journal of Neuroscience, vol. 69, No. 1-4 (125-130), 1993 (Abstract Only pp. 1-2).

Satoh et al., "Characterization of Human and Rat Glucagon-Like Peptide-1 Receptors in the Neurointermediate Lobe: Lack of Coupling to Either Stimulation or Inhibitition of Adenylyl Cyclase," Endocrinology 141: 1301-9 (200).

Shughrue et al., "Glucagon-like Peptide-1 Recept (GLP1-R) MRNA in the Rat Hypothalmus," Endocrinology 137 (11): 5159-62 (1996).

Siram et al., "Experimental Allergic Encephalomyelitis a Misleading Model of Multiple Sclerosis", Ann. Neurol. vol. 58, pp. 939-945 (2005).

Steinman et al., "How to Successfully Apply Animal Studies in Experimental Allergic Encephalomyelitis to Research on Multiple Sclerosis", Ann. Neurol. vol. 60, pp. 12-21 (2006).

Suzuki et al,, "A Role of Endogenous GLP-1 in Amnesia and Neuronal Death Induced by Ccontinuous 1.C.V. Infusion of Beta-Amyloid Protein in Rat." Jpm. J. Pharmacol. 82(1):236P, p. 468 (2000).

Suzuki et al., "An Increased Percentage of Long Amyloid b Protein Secreted by Familial Amyloid b Protein Precursor (bAPP217) Mutants," Science 264: 1336-1340 (1994).

Tancredi et al., "Synthesis and Biological Activity of New Bradykinin Pseudopeptide B1 Receptor Agonists Containing Alkylic Spacers", Bioorganic & Medicinal Chemistry Letters 7:2661-2664 (1997).

Teitelman "Induction of Beta-Cell Neogenesis by Islet Injury," Diabetes Metabolism Rev. 12: 91-102 (1996).

Thorens et al., "Expression Cloning of the Pancreatic Beta Cell Receptor for the Glucoincretin Hormone Glucagon-like Peptide 1," Proc. Natl. Acad. Sci. USA 89: 8641-8645 (1992).

(56) References Cited

OTHER PUBLICATIONS

Thorens et al., "Glucagon-Like Peptide-1 and the Control of Insulin Secretion in the Normal State and in NIDDM," Diabetes 42: 1219-1225 (1993).
Thorens et al., "Cloning and Functional Expression of the Human Isleet GLP-1 Receptor Demonstartion That Exendin-4 Is an Agonist and Exendin-(9-39) an Antagonist of the Receptor," Diabetes 42: 1678-1682 (1993).
Valverde and Villanueva-Penacarrillo et al., "In Vitro Insulinomimetic Effects of GLP-1 in Liver, Muscle and Fat." Acta Physiologica Scandinavica 157: 359-360 (1996).
Wang et al., "GIP Regulates Glucose Transporters, Hexokinases, and Glucose-Induced Insulin Secretion in RIN 1046-38 Cells," Mol. Cell. Endo. 116: 81-87 (1996).
Wang et al., "Glucagon-Like Peptide-1 Affects Gene Transcription and Messenger Ribonucleic Acid Stability of Components of the Insulinsecretory System in RIN 1046-38 Cells," Endocrinology 136: 4910-4917 (1995).
Wang et al., "Glucagon-Like Peptides-1 Can Reverse the Age Related Decline in Glucose Tolerance in Rats." J. Clin. Invest. 99:2883-2889 (1997).
Wang et al., "Glucagon-Like Peptide-1 is a Physiological Incretin in Rat." J. Clin Invest 95:417-421 (1995).
Wei et al., "Tissue-Specific Expression of the Human Receptor for Glucagon-Like Peptide-1: Brain Heart and Pancreatic Forms Have the Same Deduced Amino Acid Sequences," FEBS Letters 358 (3): 219-224 (Jan. 30, 1995).
Widman et all, "Desensitization and Phosporylation of the Glucagon-Like Peptide-1 (GLP-1) Receptor by GLP-1 and 4-Phorbol 12-Myristate 13-Acetate," Mol. Endocrinol. 10:62-75, (1996).
Willms et al., "Gastric Emptying, Glucose Responses, and Insulin Secretion After a Liquid Test Meal: Effects of Exogenousglucagon-Like Peptide-1 (GLP-1)-(7-36) Amide in Type 2 (Non-Insulin-Dependent) Diabetic Patients," Clin. Endocrinol. Metab. 81:327-332 (1996).
Yada et al., "Glucagon-Like Peptide-1-(7-36) Amide and Rise in a Cyclic Adenosine 3',5'-Monophasphate Increase Cyosolic Free CA2+ in Rat Pancreatic b-Cells by Enhancing CA2+ Channel Activity." Endocrinology 133: 1685-1692.
Robertson, et al., "Protection Against Spinal Code Ischemia With Insulin Induced Hypoglycemia", J. Neurosurg. 67: 739-744 (1987).
Ahren et al., "No Correlation Between Insulin and Islet Amyloid Polypeptide After Stimulation With Glucagon-Like Peptide-1 in Type 2 Diabetes", EP Journal of Endocrinology, 1997, vol. 137, pp. 643-649.
Azzouz, M., "Gene Therapy for ALS: Progress and Prospects,", Biochim. Biophys. Acta 1762: 1122-1127 (2006).
Bressler et al., "Pharmacological Regulation of Blood Glucose Levels in Non-Insulin Dependent Diabetes Mellitus," Arch. Int. Med. 157:836-848 (1997).
Burcelin, et al., "Long-Lasting ANTIDIAbETIC Effect of a Dipeptidyl Peptidase IV-Resistant Analog of Glucagon-Like Peptide-1", Metabolism 48: 252-258 (1999).
Calvo et al., "Structural Characterization by Affinty Cross-Linking of Gulcagon-Like Peptide-1(7-36) Amide Receptor in Rat Brain," J. Neurochem, 64 (1): 299-306 (1995).
Campos et al., "Divergent Tissue-Specific and Developmental Expression of Receptors for Glucagons and Glucagon-Like Peptide-1 in the Mouse," Endocrinology 134: 2156-64 (1994).
Chen at al., "Tissue-specific expression of unique mRNAS that encode proglucagon-derived peptides of exendin-4 in the lizard," J. Biol. Chem. 272: 4108-4115 (1997).
Citron, M. "Alzheimer's Disease: Treatments in Discovery and Development", Nature Neuroscience 5:1055-1057 (2002).
Deacon et al., "Dipeptidyl Peptidase IV Resistant Analogues of Glucagons-Like Peptide-1 Which Have Extended Metabolic Stability and Improved Biological Activity", Diabetologia 41: 271-278 (1998).

De Ore et al., "The effect of GLP-1 on insulin release in young and old rats in the fasting state and during an intravenous glucose tolerance test," J. Gerontol. 52: B245-249 (1997).
M.E. Doyle et al., "Insertion of an N-Terminal 6-Aminohexanoic Acid after the 7 Amino Acid Position of Glucagon-Like Peptide-1 Produces a Long-Acting Hypoglycemic Agent", Endocrinology, 142(10), pp. 4462-4468 (2001).
Doyle M. et al, "Insertion of an N-Terminal 6-Aminohexanoic Acid After the 7 Amino Acid Position of Glucagon-Like Peptide-1 Produces a Long-Acing Hypoglycemic Agent" Endocrinology, vol. 142. No. 10, p. 4462-4468 (2001).
Drucker et al., "Glucagon-like peptide 1 stimulates insulin gene expression and increases cyclic AMP levels in a rat islet cell line," Proc. Natl. Acad. Sci.: 84: 3434-343 (1987).
Drucker, "Minireview; The Glucagon-Like Peptides," Endocrinology 142:521-527 (2001).
Egan et al. "Glucagon-like peptide-1 (7-36) aminde (GLP-1) enhances insulin-stimulated glucose metabolism in 3T3-1I adipocytes: One of several potential extrapancreatic sites of GLP-1 actoion," Endocrinology 135:2070-2075 (1994).
Elahi et al., "The Insulinotropic Actions of Glucose-Dependent Insulinotropic Polypeptide (GIP) and Glucagon-Like Peptide-1 (7-37) in Normal and Diabetic Subjects," Regul. Pep. 51:63-74 (1994).
Elahi et al., "The effect of age and glucose concentration on insulin secretion by the isolated perfused pancreas." Endocrinology 116: 11-16 (1985).
Federal Register 63, Friday, Feb. 20, 1998, p. 8652.
Fehman, "Cell and Molecular Biology of the Incretin Hormones Glucagon-Like Peptide-1 and Glucose-Dependent Insulin Releasing Polypeptide." Endocrine Rev. 16:390-410 (1995).
Fehmann et al "Insulinotropic Hormone Glucagon-Like Peptide-1 (7-37) Stimulation of Proinsulin Gene Expression and Proinsulin Biosynthesis in Insulinoma bTC-1 Cells." Endocrinology 130: 159-166 (1992).
File Medline on STN An No. 2005478947, Simmons, Zachary, "Management Strategies for Patients with Amyotrphoic Lateral Sclerosis From Diagnosis Through Death", The Neurologist (Sep. 2005), vol. 11, No. 5, pp. 257-270 Abstract Only.
Gefel et al., "Glucagon-Like Peptide I Analogs:Effects on Insulin Secretin and Adenosine 3',5'-Monophosphate Formation." Endocrinology 126:2164-68 (1990).
Geula and Mesulam, "Cortical Cholinergic Fibers in Aging and Alxheimers Disease: A Morphometric Study," Neuroscience 33: 469-481 (1989).
Ghazzi, et al, "Cardiac and Glycemic Benefits of Troglitazone Treatment in NIDDM," Diabetes 46: 433-439 (1997).
Goke et al., "Distribution of GLP-1 Binding Sites in the Rat Brain : Evidence That Exendin-4 Is a Ligand of Brain GLP-1 Binding Sites," Eur. J. Neurosci: 2294-2300 (1995).
Goke et al., "Exendin-4 Is a High Potency Agonist and Truncated Exendin-(9-39)-Amide in an Antagonist At the Glucagon-Like Peptide-1-(7-36)-Amide Receptor of Insulin-Secreting b-Cells," J. Biol. Chem. 268: 19650-19655 (1993).
Greig et al., "Once Daily Injection of Exendin-4 to Diabetic Mice Achieves Long-Term Beneficial Effects on Blood Glucose Concentrations." Diabetologia 42: 45-50 (1999).
Gromoda et al, "Glucagon-like peptide 1(7-36) Amide Stimulates Exocytosis in Human Pancreatic b-cells by both proximal and distal regulatory steps in stimullus-secretion Coupling" Diabetes 47: 57-65 (1998).
Gutniak et al., "Antidiabticogenic Effet of Glucagon-Like Peptide-1(7-36 Amide) in Normal Subjects and Patients With Diabetes Mellitus," N. Eng. J. Med. 326: 1316-1322 (1992).
Guz et al., "Expression of Murine STF-1, Aputative Insulin Gene Transcription Factor, in b Cells of Pancreas, Duodenal Epithelium and Pancreatic Excrine and Endocrine Progenitors During Ontogeny." Development 121: 11-18 (1995).
Hawes et al., "Distinct Pathways of G1 and GQ-Mediated Mitogen-Activiated Protein Kinase Actiation," J. Biol. Chem. 270: 17148-17153 (1995).

(56) References Cited

OTHER PUBLICATIONS

Holz et al., "Activation of a Camp-Regulated CA2+-Signaling Pathway in Pancreatic Beta-Cells by the Insulintropic Hormone Glucagon-Like-Peptide-1." J. Boil. Chem. 270: 17749-17757 (1995).

Hosokawa et al., "Mechanism of Impaired Glucose-Potentiated Insulin Secretion in Diabteic 90% Pancreatectomy Rats. Study Using Glucagonlike Peptide-1 (7-37)" J. Clin. Invest 97:180-1860 (1996).

Iwai et al., "Effects of Glucagon-Like Pepties-1 on LTP in Beta-Amyloid Protein (1-42)-Treated Hippocampal Slices." Soc. Neurosci. Abstr. 26 (12): 1116 Abstract No. 420.7 (2000).

Jin et al., "Distribution of Glucagonlike Peptide 1 (GLP-1), Glucagon, and Glucentin in the Rat Brain: An Immunocytochemical Study," J. Comp. Neurol. 271: 519-532 (1988).

Kimura et al., "High Concentrations of Cholecystoskinin Octapeptide Suppress Protein Kinases C Activity in Guinea Pig Pancreatic Acini." Peptides 17: 917-925 (1996).

Koide et al., "Biosynthesis of a Protein Containing a Nonprotein Amino Acid by *Escherichia coli*: L-2-Aminohexanoic Acid At Position 21 in Human Epidermal Growth Factor," Proc. Natl. Acad.Sci. USA, 1998 vol. 85, pp. 6237-6241.

Kondo et al., "Effects of Endogenous GLP-1 on Neurite Elongation in Rat Primary Cultured Hippocampal Neurons," Jpn., J. Pharmacol. 85(1):276, p. 866 (2001).

Korczyn et al., "Emerging Therapies in the Pharmacological Treatment of Parkinson's Disease", Drugs. vol. 62, No. 5, pp. 775-786 (2002).

Lahiri et al., "Cholinestrase Inhibitors, b-Amyloid Precursor Protein and Amyloid b-Peptides in Alzheimer's Disease," Acta Neurol. Scand. Suppl. 176: 60-67 (2000).

Lahiri et al., "Exendin-4 (ex-4) Revives PC12 Cells From Nerve Growth Factor (NGF)-Mediated Cell Death and Apoptosis," Soc. Neurosci. Abstr. 27(2); 2620, Abstract No. 983.16 (2001).

Lee "Neurod and Neurogenesis," Dev. Neuroscience 19: 27-32 (1997).

Lovshin et al. "Glucagon-Like Peptide (GLP)-2 Action in the Murine Central Nervous System Is Enhanced by Elimination of GLP-1 Receptor Signaling," J. Biol.Chem. 276(24):21486-21499 (Jun. 2001).

Margolis et al., "Diagnosis of Huntington Disease", Clinical Chemistry, vol. 49, No. 10, pp. 1726-1732 (2003).

Malhotra et al., "Exendin-4, a New Peptide From Heloderma Suspectum Vemon, Poteniates Cholecystokinin-Induced Amylase From Rat Pancreatic Acini." Regul. Pept. 41: 149-156 (1992).

Mark et al., "Amyloid b-Peptide Impairs Glucose Transport in Hippocampal and Cortical Neurons: Involvement of Membrane Lipid Peroxidation." J. Neurosci. 17: 1046-1054 (1997).

Mashima et al., "Betacellulin and Activin A. Coordinately Convert Amylase-Secreting AR$2J Cells Into Insulin-Secreting Cells." J. Clin. Invest. 97:1647-1654 (1996).

Mashima et al., "Formation of Insulin-Production Cells From Pancreatic Acinar AR42J Cells by Hepatocyte Growth Factor." Endocrinology 137:3969-3976 (1996).

Mattson et al., "Neurotrophic Factors Attenuate Glutamate-Induced Accumulation of Peroxides, Elevation of Intracellular CA2+ Concentration, and Neurotoxocity and Increase Antioxidant Enzyme Activities in Hippocampal Neurons," J. Neurochem 65 (4): 1740-1751 (1995).

Moceri et al., "Early-Life Rish Factors and the Development of Alzheimer's Disease," Neurology 54:415-420 (2000).

McIntosh et al. "The molecular and cellular sequelae of experimental traumatic brain injury: pathogenetic mechanisms" Neuropathology and Appl Neurobiology 24: p. 251-267; Jan. 7, 1998.

* cited by examiner

FIG. 1A

| # | SEQ ID | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|
| 12 | SEQ ID NO:9  | H | A | E | G | T | F | T | S | D | V | S | S | Y | L | E | G | Q | A | A | K | E | F | I | A | W | L | V | K | G | G | R | P | S | S | G | A | P P P S |
| 13 | SEQ ID NO:10 | H | A | E | G | T | F | T | S | D | L | S | K | Q | M | E | E | E | A | V | R | L | F | I | E | W | L | K | N | G | G |   | P | S | S | G | A | P P P S |
| 14 | SEQ ID NO:11 | H | A | E | G | T | F | T | S | D | L | S | K | Q | M | E | E | E | A | V | R | L | F | I | E | W | L | K | N | G | G | | | | | | | |
| 15 | SEQ ID NO:12 | H | G | E | G | T | F | T | S | D | L | S | K | Q | M | E | E | E | A | V | R | L | F | I | E | W | L | K | N | G | G | | P | S | S | G | A | P P |
| 16 | SEQ ID NO:13 | H | G | E | G | T | F | T | S | D | L | S | K | Q | M | E | E | E | A | V | R | L | F | I | E | W | L | K | N | G | G | | P | S | S | G | A | P P P S |
| 17 | SEQ ID NO:14 | H | G | E | G | T | F | T | S | D | L | S | K | Q | M | E | E | E | A | V | R | L | F | I | E | W | L | K | N | G | G | | P | S | S | G | A | |
| 18 | SEQ ID NO:15 | H | G | E | G | T | F | T | S | D | L | S | K | Q | M | E | E | E | A | V | R | L | F | I | E | W | L | K | N | G | G | | P | S | S | | | |
| 19 | SEQ ID NO:16 | H | G | E | G | T | F | T | S | D | L | S | K | Q | M | E | E | E | A | V | R | L | F | I | E | W | L | K | N | G | G | | | | | | | |
| 20 | SEQ ID NO:17 | H | G | E | G | T | F | T | S | D | L | S | K | Q | M | E | E | E | A | V | R | L | F | I | E | W | L | K | N | G | | | | | | | | |
| 21 | SEQ ID NO:18 | H | G | E | G | T | F | T | S | D | L | S | K | Q | M | E | E | E | A | V | R | L | F | I | E | W | L | | | | | | | | | | | |
| 22 | SEQ ID NO:19 | H | G | E | G | T | F | T | S | D | L | S | K | Q | M | E | E | E | A | V | R | L | F | I | | W | L | | | | | | | | | | | |
| 23 | SEQ ID NO:20 | H | G | E | G | T | F | T | S | D | L | S | K | Q | M | E | E | E | A | | V | R | | | | | | | | | | | | | | | | |
| 24 | SEQ ID NO:21 | H | A | E | G | T | F | T | S | D | | | | | | | | | | | | | | | | | | | | | | | | | | | | |
| 25 | SEQ ID NO:22 | H | A | E | G | T | F | T | S | D | V | S | S | Y | L | E | G | Q | A | A | K | E | F | I | A | W | L | V | K | G | R | 4 AA spacer at 8 and 9 | | | | | | |
| 26 | SEQ ID NO:23 | H | A | E | G | T | F | T | S | D | V | S | S | Y | L | E | G | Q | A | A | K | E | F | I | A | W | L | V | K | G | R | 8 AA spacer at 8 and 9 | | | | | | |
| 27 | SEQ ID NO:24 | H | G | E | G | T | F | T | S | D | V | S | S | Y | M | E | E | Q | A | A | K | E | F | I | A | W | L | V | K | G | R | | | | | | | |
| 28 | SEQ ID NO:25 | H | G | E | G | T | F | T | S | D | V | S | S | Y | M | E | G | Q | A | A | K | E | F | I | A | W | L | V | K | G | R | | | | | | | |
| 29 | SEQ ID NO:26 | H | G | E | G | T | F | T | S | D | V | S | S | Y | L | E | E | Q | A | A | K | E | F | I | A | W | L | V | K | G | R | | | | | | | |
| 30 | SEQ ID NO:27 | H | G | E | G | T | F | T | S | D | V | S | S | K | Y | L | E | G | Q | A | A | K | E | F | I | A | W | L | V | K | G | R | | | | | | |
| 31 | SEQ ID NO:28 | H | G | E | G | T | F | T | S | D | V | S | S | K | Y | L | E | E | Q | A | A | K | E | F | I | A | W | L | V | K | G | R | | | | | | |
| 32 | SEQ ID NO:29 | H | G | E | G | T | F | T | S | D | V | S | S | K | Y | L | E | E | A | A | K | E | F | I | A | W | L | V | K | G | G | | | | | | | |
| 33 | SEQ ID NO:30 | H | G | E | G | T | F | T | S | D | V | S | S | K | Y | L | E | E | A | A | K | E | F | I | A | W | L | V | K | G | R | | | | | | | |

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|---|---|---|---|---|---|---|---|---|---|---|---|---|---|---|---|---|---|---|---|
| 34 (Ex-4 WOT R) (SEQ ID NO:31) | H | G | E | G | T | F | T | S | D | L | S | K | Q | M | E | E | E | A | V | R | L | F | I | E | W | L | K | N | G | R | | | | | | | | | |
| 35 (SEQ ID NO:32) | H | G | E | G | T | F | T | S | D | L | S | K | Q | M | E | E | E | A | V | R | L | F | I | A | W | L | K | N | G | R | | | | | | | | | |
| 36 (SEQ ID NO:33) | H | G | E | G | T | F | T | S | D | L | S | K | Q | M | E | E | E | A | V | R | E | F | I | A | W | L | K | N | G | R | | | | | | | | | |
| 37 (SEQ ID NO:34) | H | G | E | G | T | F | T | S | D | V | S | S | Y | L | E | G | Q | A | A | K | E | F | I | A | W | L | K | N | G | C | P | S | S | G | A | P | P | P | |
| 38 (SEQ ID NO:35) | H | G | E | G | T | F | T | S | D | V | S | S | Y | L | E | G | Q | A | A | K | E | F | I | A | W | L | K | N | G | G | P | S | S | G | A | P | P | P | |
| 39 (SEQ ID NO:36) | H | G | E | G | T | F | T | S | D | V | S | S | Y | L | E | G | Q | A | V | R | L | F | I | E | W | L | K | N | G | R | | | | | | | | | |
| 40 (SEQ ID NO:37) | H | G | E | G | T | F | T | S | D | V | S | S | Y | L | E | G | Q | A | A | K | E | F | I | A | W | L | K | N | G | R | | | | | | | | | |
| 41 (SEQ ID NO:38) | H | G | E | G | T | F | I | S | D | Y | S | I | A | M | D | K | I | H | Q | Q | D | F | V | N | W | L | L | A | Q | K | G | K | K | N | D | W | K | H | N I T Q |
| 42 (SEQ ID NO:39) | H | G | E | G | T | F | T | S | D | V | S | S | Y | L | E | G | Q | A | A | K | E | F | I | A | W | L | V | K | G | R | P | S | S | G | A | P | P | P | S S G A P |
| 43 (SEQ ID NO:40) | H | G | E | G | T | F | T | S | D | V | S | S | Y | L | E | G | Q | A | A | K | E | F | I | A | W | L | V | K | G | R | P | S | S | G | A | P | P | P | S S |
| 44 (SEQ ID NO:41) | H | G | E | G | T | F | T | S | D | V | S | S | Y | L | E | G | Q | A | A | K | E | F | I | A | W | L | V | K | G | R | P | S | S | G | A | P | P | P | S S G A P |
| 45 (SEQ ID NO:42) | H | G | E | G | T | F | T | S | D | V | S | S | Y | L | E | G | Q | A | A | K | E | F | I | A | W | L | V | K | G | R | P | S | S | G | A | P | P | P | S S |
| 46 (SEQ ID NO:43) | H | A | E | G | T | F | T | S | D | V | S | S | Y | L | E | G | Q | A | A | K | E | F | I | A | W | L | V | K | G | R | P | S | S | G | A | P | P | P | S S G A P |
| 47 (SEQ ID NO:44) | H | A | E | G | T | F | T | S | D | V | S | S | Y | L | E | G | Q | A | A | K | E | F | I | A | W | L | V | K | G | R | P | S | S | G | A | P | P | P | S S |
| 48 (SEQ ID NO:45) | H | A | E | G | T | F | T | S | D | V | S | S | Y | L | E | G | Q | A | A | K | E | F | I | A | W | L | V | K | G | R | P | S | S | G | A | P | P | P | S S G A P |
| (SEQ ID NO:46) | H | A | E | G | T | F | T | S | D | V | S | S | Y | L | E | G | Q | A | A | K | E | F | I | A | W | L | V | K | G | R | P | S | S | G | A | P | P | P | S S |
| (SEQ ID NO:47) | H | A | E | G | T | F | T | S | D | V | S | S | Y | L | E | G | Q | A | A | K | E | F | I | A | W | L | V | K | G | R | P | S | S | G | A | P | P | P | S S G A P |
| 48 (SEQ ID NO:48) | Y | A | E | G | T | F | I | S | D | Y | S | I | A | M | D | K | I | H | Q | Q | D | F | V | N | W | L | L | A | Q | K | G | K | K | N | D | W | K | H | N I T Q |

SEQUENCE LISTING

```
<160> NUMBER OF SEQ ID NOS: 52

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 2
<211> LENGTH: 39
```

-continued

```
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 3

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 5

His Gly Glu Gly Thr Phe Thr Ser Asp Leu Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 6
```

```
His Gly Glu Gly Thr Phe Thr Ser Asp Leu Ser Lys Gln Met Glu Gly
1               5                   10                  15

Gln Ala Ala Lys Glu Phe Ile Ala Trp Leu Val Lys Gly Arg
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 8

His Xaa Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 30
<223> OTHER INFORMATION: Xaa=any amino acid

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa Pro Ser
            20                  25                  30

Ser Gly Ala Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 10
```

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 11

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 13
<211> LENGTH: 35
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 15

His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Asn
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 16

His Gly Glu Gly Thr Phe Thr Ser Asp Leu Ser Lys Gln Met Glu Glu
 1               5                   10                  15

Glu Ala Val Arg Leu Phe Ile Glu Trp Leu
            20                  25

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 17

His Gly Glu Gly Thr Phe Thr Ser Asp Leu Ser Lys Gln Met Glu Glu
 1               5                   10                  15

Glu Ala Val Arg Leu Phe Ile
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 18

His Gly Glu Gly Thr Phe Thr Ser Asp Leu Ser Lys Gln Met Glu Glu
 1               5                   10                  15

Glu Ala Val Arg
            20

<210> SEQ ID NO 19
<211> LENGTH: 17
<212> TYPE: PRT
<213> ORGANISM: Artificial Sequence

```
<220> FEATURE:
<223> OTHER INFORMATION: Description of Artificial Sequence: Note =
      Synthetic Construct

<400> SEQUENCE: 19

His Gly Glu Gly Thr Phe Thr Ser Asp Leu Ser Lys Gln Met Glu Glu
1               5                   10                  15

Glu

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 20

His Gly Glu Gly Thr Phe Thr Ser Asp Leu Ser Lys Gln Met
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 21

His Gly Glu Gly Thr Phe Thr Ser Asp Leu Ser
1               5                   10

<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 3,4,5,6
<223> OTHER INFORMATION: Xaa= aminohexanoic acid

<400> SEQUENCE: 22

His Ala Xaa Xaa Xaa Xaa Glu Gly Thr Phe Thr Ser Asp Val Ser Ser
1               5                   10                  15

Tyr Leu Glu Gly Gln Ala Ala Lys Glu Phe Ile Ala Trp Leu Val Lys
            20                  25                  30

Gly Arg

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 3,4,5,6,7,8,9,10
<223> OTHER INFORMATION: Xaa=aminohexanoic acid

<400> SEQUENCE: 23

His Ala Xaa Xaa Xaa Xaa Xaa Xaa Xaa Xaa Glu Gly Thr Phe Thr Ser
1               5                   10                  15
```

```
Asp Val Ser Ser Tyr Leu Glu Gly Gln Ala Ala Lys Glu Phe Ile Ala
            20                  25                  30

Trp Leu Val Lys Gly Arg
        35
```

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 24

```
His Gly Glu Gly Thr Phe Thr Ser Asp Val Ser Ser Tyr Met Glu Glu
 1               5                  10                  15

Gln Ala Val Arg Leu Phe Ile Ala Trp Leu Val Lys Gly Arg
            20                  25                  30
```

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 25

```
His Gly Glu Gly Thr Phe Thr Ser Asp Val Ser Ser Tyr Met Glu Glu
 1               5                  10                  15

Gln Ala Ala Lys Glu Phe Ile Ala Trp Leu Val Lys Gly Arg
            20                  25                  30
```

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 26

```
His Gly Glu Gly Thr Phe Thr Ser Asp Val Ser Ser Tyr Leu Glu Gly
 1               5                  10                  15

Gln Ala Val Arg Leu Phe Ile Ala Trp Leu Val Lys Gly Arg
            20                  25                  30
```

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 27

```
His Gly Glu Gly Thr Phe Thr Ser Asp Val Ser Lys Tyr Leu Glu Gly
 1               5                  10                  15

Gln Ala Ala Lys Glu Phe Ile Ala Trp Leu Val Lys Gly Arg
            20                  25                  30
```

<210> SEQ ID NO 28
<211> LENGTH: 30
<212> TYPE: PRT

```
<213> ORGANISM: Artificial Sequence
<220> FEATURE:
<223> OTHER INFORMATION: Description of Artificial Sequence: Note =
      Synthetic Construct

<400> SEQUENCE: 28

His Gly Glu Gly Thr Phe Thr Ser Asp Val Ser Lys Tyr Leu Glu Glu
 1               5                  10                  15

Glu Ala Ala Lys Glu Phe Ile Ala Trp Leu Val Lys Gly Arg
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 29

His Gly Glu Gly Thr Phe Thr Ser Asp Val Ser Lys Tyr Leu Glu Glu
 1               5                  10                  15

Glu Ala Ala Lys Glu Phe Ile Glu Trp Leu Val Lys Gly Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 30

His Gly Glu Gly Thr Phe Thr Ser Asp Val Ser Lys Tyr Leu Glu Glu
 1               5                  10                  15

Glu Ala Ala Lys Glu Phe Ile Glu Trp Leu Val Lys Gly Arg
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 31

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Arg
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 32

His Gly Glu Gly Thr Phe Thr Ser Asp Leu Ser Lys Gln Met Glu Glu
 1               5                  10                  15

Glu Ala Val Arg Leu Phe Ile Ala Trp Leu Lys Asn Gly Arg
```

```
                    20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 33

His Gly Glu Gly Thr Phe Thr Ser Asp Leu Ser Lys Gln Met Glu Glu
1               5                   10                  15

Glu Ala Val Arg Glu Phe Ile Ala Trp Leu Lys Asn Gly Arg
            20                  25                  30

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 34

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 35

His Gly Glu Gly Thr Phe Thr Ser Asp Val Ser Ser Tyr Leu Glu Gly
1               5                   10                  15

Gln Ala Ala Lys Glu Phe Ile Glu Trp Leu Lys Asn Gly Gly Pro Ser
            20                  25                  30

Ser Gly Ala Pro Pro Pro Ser
        35

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 36

His Gly Glu Gly Thr Phe Thr Ser Asp Val Ser Ser Tyr Leu Glu Glu
1               5                   10                  15

Glu Ala Val Arg Leu Phe Ile Ala Trp Leu Val Lys Gly Arg
            20                  25                  30

<210> SEQ ID NO 37
<211> LENGTH: 30
```

```
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 37

His Gly Glu Gly Thr Phe Thr Ser Asp Leu Ser Lys Gln Met Glu Gly
1               5                   10                  15

Gln Ala Ala Lys Glu Phe Ile Glu Trp Leu Lys Asn Gly Arg
            20                  25                  30

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 38

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 39
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 39

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Pro Ser
        35

<210> SEQ ID NO 40
<211> LENGTH: 42
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 40

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Pro Ser Gly Ala Pro
        35                  40

<210> SEQ ID NO 41
<211> LENGTH: 45
<212> TYPE: PRT
<213> ORGANISM: Artificial Sequence
```

```
<220> FEATURE:
<223> OTHER INFORMATION: Description of Artificial Sequence: Note =
      Synthetic Construct

<400> SEQUENCE: 41

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Pro Ser
             20                  25                  30

Ser Gly Ala Pro Pro Pro Ser Gly Ala Pro Pro Ser Ser
         35                  40                  45

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 42

His Xaa Ala Glu Gly Thr Phe Thr Ser Asp Val Ser Ser Tyr Leu Glu
  1               5                  10                  15

Gly Gln Ala Ala Lys Glu Phe Ile Ala Trp Leu Val Lys Gly Arg Pro
             20                  25                  30

Ser Ser Gly Ala Pro Pro Pro Ser
         35                  40

<210> SEQ ID NO 43
<211> LENGTH: 43
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 43

His Xaa Ala Glu Gly Thr Phe Thr Ser Asp Val Ser Ser Tyr Leu Glu
  1               5                  10                  15

Gly Gln Ala Ala Lys Glu Phe Ile Ala Trp Leu Val Lys Gly Arg Pro
             20                  25                  30

Ser Ser Gly Ala Pro Pro Pro Ser Gly Ala Pro
         35                  40

<210> SEQ ID NO 44
<211> LENGTH: 46
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 44

His Xaa Ala Glu Gly Thr Phe Thr Ser Asp Val Ser Ser Tyr Leu Glu
```

-continued

```
                1               5                   10                  15
Gly Gln Ala Ala Lys Glu Phe Ile Ala Trp Leu Val Lys Gly Arg Pro
                20                  25                  30
Ser Ser Gly Ala Pro Pro Ser Gly Ala Pro Pro Ser Ser
                35                  40                  45
```

<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 3
<223> OTHER INFORMATION: Xaa= aminohexanoic acid

<400> SEQUENCE: 45

```
His Ala Xaa Glu Gly Thr Phe Thr Ser Asp Val Ser Ser Tyr Leu Glu
1               5                   10                  15
Gly Gln Ala Ala Lys Glu Phe Ile Ala Trp Leu Val Lys Gly Arg Pro
                20                  25                  30
Ser Ser Gly Ala Pro Pro Ser
                35                  40
```

<210> SEQ ID NO 46
<211> LENGTH: 43
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 3
<223> OTHER INFORMATION: Xaa= aminohexanoic acid

<400> SEQUENCE: 46

```
His Ala Xaa Glu Gly Thr Phe Thr Ser Asp Val Ser Ser Tyr Leu Glu
1               5                   10                  15
Gly Gln Ala Ala Lys Glu Phe Ile Ala Trp Leu Val Lys Gly Arg Pro
                20                  25                  30
Ser Ser Gly Ala Pro Pro Ser Gly Ala Pro
                35                  40
```

<210> SEQ ID NO 47
<211> LENGTH: 46
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 3
<223> OTHER INFORMATION: Xaa= aminohexanoic acid

<400> SEQUENCE: 47

```
His Ala Xaa Glu Gly Thr Phe Thr Ser Asp Val Ser Ser Tyr Leu Glu
1               5                   10                  15
Gly Gln Ala Ala Lys Glu Phe Ile Ala Trp Leu Val Lys Gly Arg Pro
                20                  25                  30
Ser Ser Gly Ala Pro Pro Ser Gly Ala Pro Pro Ser Ser
                35                  40                  45
```

<210> SEQ ID NO 48
<211> LENGTH: 43
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 48

Tyr Xaa Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Gly
            20                  25                  30

Lys Lys Asn Asp Trp Lys His Asn Ile Thr Gln
        35                  40

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 49

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 50

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Pro Ser
        35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 51

His Gly Glu Gly Thr Phe Thr Ser Asp Val Ser Ser Tyr Leu Glu Gly
1               5                   10                  15

```
Gln Ala Ala Lys Glu Phe Ile Ala Trp Leu Val Lys Gly Arg Pro Ser
            20                  25                  30

Ser Gly Ala Pro
        35

<210> SEQ ID NO 52
<211> LENGTH: 33
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 52

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Pro Ser
            20                  25                  30

Ser
```

GLP-1, EXENDIN-4, PEPTIDE ANALOGS AND USES THEREOF

CROSS REFERENCE TO RELATED APPLICATION

This application is a continuation of U.S. patent application Ser. No. 12/317,042, filed Dec. 18, 2008, which is a continuation of U.S. patent application Ser. No. 10/485,140, filed Apr. 1, 2004, now U.S. Pat. No. 7,576,050, which is the National Stage Entry of International Patent Application No. PCT/US2002/024141, filed Jul. 30, 2002, which claims priority to U.S. Application Ser. No. 60/309,076, filed Jul. 31, 2001. The aforementioned patent applications are hereby incorporated by reference in their entirety.

BACKGROUND OF THE INVENTION

1. Field of the Invention

This invention relates generally to glucagon-like peptide-1 (GLP-1), exendin-4 and their peptide analogs. The invention also relates to their uses in the treatment of diabetes and neurodegenerative conditions.

2. Background Art

Pancreatic beta cell dysfunction and the concomitant decrease in insulin production can result in diabetes mellitus. In type 1 diabetes, the beta cells are completely destroyed by the immune system, resulting in an absence of insulin producing cells (Physician's Guide to Insulin Dependent [Type I] Diabetes Mellitus: Diagnosis and Treatment, American Diabetes Association, 1988). In type 2 diabetes, the beta cells become progressively less efficient as the target tissues become resistant to the effects of insulin on glucose uptake. Thus, beta cells are absent in people with type 1 diabetes and are functionally impaired in people with type 2 diabetes.

Beta cell dysfunction currently is treated in several different ways. In the treatment of type 1 diabetes or the late stages of type 2 diabetes, insulin replacement therapy is necessary. Insulin therapy, although life-saving, does not restore normoglycemia, even when continuous infusions or multiple injections are used in complex regimes. For example, postprandial levels of glucose continue to be excessively high in individuals on insulin replacement therapy. Thus, insulin therapy must be delivered by multiple daily injections or continuous infusion and the effects must be carefully monitored to avoid hyperglycemia, hypoglycemia, metabolic acidosis, and ketosis.

People with type 2 diabetes are generally treated with drugs that stimulate insulin production and secretion from the beta cells and/or improve insulin sensitivity. A major disadvantage of these drugs, however, is that insulin production and secretion is promoted regardless of the level of blood glucose. Thus, food intake must be balanced against the promotion of insulin production and secretion to avoid hypoglycemia or hyperglycemia. In recent years several new agents have become available to treat type 2 diabetes. These include metformin, rosiglitazone, pioglitazone, and acarbose (see Bressler and Johnson, 1997). However, the drop in hemoglobin A1c obtained by these newer agents is less than adequate (Ghazzi et al., 1997), suggesting that they will not improve the long-term control of diabetes mellitus.

Glucagon-like peptide-1 (GLP-1), a hormone normally secreted by neuroendocrine cells of the gut in response to food, has been suggested as a new treatment for type 2 diabetes (Gutniak et al., 1992; Nauck et al., *J. Clin. Invest.,* 1993). It increases insulin release by the beta cells even in subjects with long-standing type 2 diabetes (Nauck et al., *Diabetologia,* 1993). GLP-1 treatment has an advantage over insulin therapy because GLP-1 stimulates endogenous insulin secretion, which turns off when blood glucose levels drop (Nauck et al., *Diabetologia,* 1993; Elahi et al., 1994). GLP-1 promotes euglycemia by increasing insulin release and synthesis, inhibiting glucagon release, and decreasing gastric emptying (Nauck et al., *Diabetologia,* 1993; Elahi et al., 1994; Wills et al., 1996; Nathan et al., 1992; De Ore et al., 1997). GLP-1 also induces an increase in hexokinase messenger RNA levels (Wang et al., *Endocrinology* 1995; Wang et al., 1996). GLP-1 is known to have a potent insulin-secreting effect on beta cells (Thorens and Waeber, 1993; Orskov, 1992) and to increase insulin biosynthesis and proinsulin gene expression when added to insulin-secreting cell lines for 24 hours (Drucker et al., 1987; Fehmann and Habener, 1992). In studies using RIN 1046-38 cells, twenty-four hour treatment with GLP-1 increased glucose responsiveness even after the GLP-1 had been removed for an hour and after several washings of the cells (Montrose-Rafizadeh et al., 1994). Thus, GLP-1 is an insulinotropic agent known to have biological effects on βcells even after it has been metabolized from the system. GLP-1 is a product of posttranslational modification of proglucagon. The sequences of GLP-1 and its active fragments GLP-1 (7-37) and GLP-1(7-36) amide are known in the art (Fehmann et al., 1995). Although GLP-1 has been proposed as a therapeutic agent in the treatment of diabetes, it has a short biological half-life (De Ore et al., 1997), even when given by a bolus subcutaneously (Ritzel et al., 1995). GLP-1 degradation (and GLP-1 (7-36) amide), in part, is due to the enzyme dipeptidyl peptidase (DPP1V), which cleaves the polypeptide between amino acids 8 and 9 (alanine and glutamic acid).

Exendin-4 is a polypeptide produced in the salivary glands of the Gila Monster lizard (Goke et al., 1993). The amino acid sequence for exendin-4 is known in the art (Fehmann et al. 1995). Although it is the product of a uniquely non-mammalian gene and appears to be expressed only in the salivary gland (Chen and Drucker, 1997), exendin-4 shares a 52% amino acid sequence homology with GLP-1 and in mammals interacts with the GLP-1 receptor (Goke et al., 1993; Thorens et al., 1993). In vitro, exendin-4 has been shown to promote insulin secretion by insulin producing cells and, given in equimolar quantities, is more potent than GLP-1 at causing insulin release from insulin producing cells. Furthermore, exendin-4 potently stimulates insulin release to reduce plasma glucose levels in both rodents and humans and is longer acting than GLP-1. Exendin-4, however, because it does not occur naturally in mammalians, has certain potential antigenic properties in mammals that GLP-1 lacks.

In addition to the reduction in insulin production that occurs in diabetes, peripheral neuropathy is commonly associated with diabetes. Twenty to thirty percent of all diabetes subjects eventually develop peripheral neuropathy. Furthermore, there are reports of increased risk of Alzheimer's disease with heart disease, stroke, hypertension, and diabetes (Moceri et al., 2000; Ott et al., 1999). Thus, diabetes is a disease that is also associated with neurodegenerative diseases.

A number of studies have demonstrated that the GLP-1 receptor is present in both the rodent (Jin et al 1988, Shughrue et al 1996) and human (Wei and Mojsov 1995, Satoh et al 2000) brains. The chemoarchitecture of the distribution appears to be largely confined to the hypothalamus, thalamus, brainstem, lateral septum, the subformical organ and the area postrema, all circumventricular areas where generally large numbers of peptide receptors are located. However, specific binding sites for GLP-1 have also been detected throughout the caudate-putamen, cerebral cortex and cerebellum (Campos et al. 1994, Calvo et al. 1995, Goke et al. 1995), albeit at low densities.

Needed in the art are polypeptides that are of therapeutic value in the treatment of diabetes and the treatment of degenerative disorders such as Alzheimer's and Parkinson's diseases, as well as the peripheral neuropathy associated with type 2 diabetes mellitus.

SUMMARY OF THE INVENTION

In accordance with the purposes of this invention, as embodied and broadly described herein, this invention, in one aspect, relates to novel polypeptide analogues of GLP-1 and exendin-4. The polypeptide, in a preferred embodiment, is insulinotropic and long-acting. Preferably, the polypeptide's insulinotropic effect is comparable to or exceeds the effect of an equimolar amount of GLP-1 or exendin-4.

The invention further relates to a purified polypeptide, the amino acid sequence of which comprises SEQ ID NO:5, SEQ ID NO:6, SEQ ID NO:7, SEQ ID NO:8, SEQ ID NO:42, SEQ ID NO:43, SEQ ID NO:44, SEQ ID NO:45, SEQ ID NO:46, SEQ ID NO:47, SEQ ID NO:48, SEQ ID NO:9, SEQ ID NO:10, SEQ ID NO:11, SEQ ID NO:12, SEQ ID NO:13, SEQ ID NO:14, SEQ ID NO:15, SEQ ID NO:25, or SEQ ID NO:33.

In another aspect, the invention relates to a method of treating a subject with diabetes, comprising administering to the subject the polypeptide of the invention in an amount that has an insulinotropic effect.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

FIG. 1 shows sequences for the 35 synthetic polypeptides tested for their insulinotropic properties and the sequences for GLP-1 and Ex-4. Dark shading shows exendin-4-like residues and light shading shows GLP-1-like residues.

FIG. 9A shows the effect on blood glucose levels and FIG. 9B shows the effect on insulin levels following subcutaneous injection of GLP-1 6-aminohexanoic acid$^8$ (24 nmol/kg) to Wistar and Zucker fatty rats and GLP-1 Gly$^8$ (24 nmol/kg) to Zucker rats only. Both Zucker and Wistar rats were fasted overnight prior to injection. The results are means±SEM, n=6 per group.

Vertical error bars represent standard error of 3 individual experimental values. Significant difference from untreated: * p<0.05 and ** p<0.01.

Figure 12:
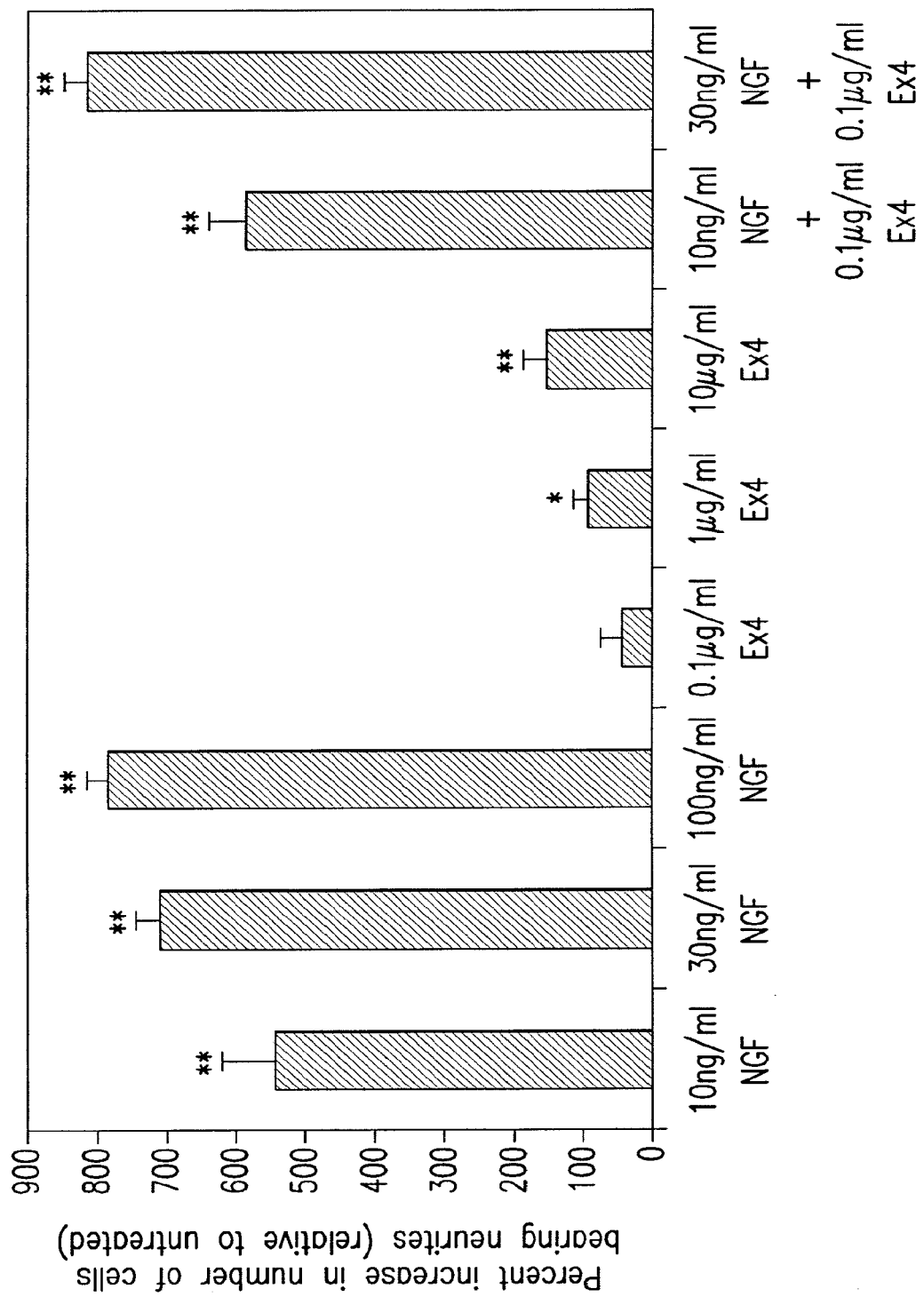

FIG. 12 shows the effect of different concentrations of NGF and/or exendin-4 treatment on neurite outgrowth in PC12 cells. Neurite outgrowth is represented as the percent increase in number of cells bearing neurites relative to untreated (low serum medium). Vertical error bars represent ±standard error of the difference between the means of six individual experimental values. Significant difference from untreated: * p<0.05 and ** p<0.01.

Figure 13:
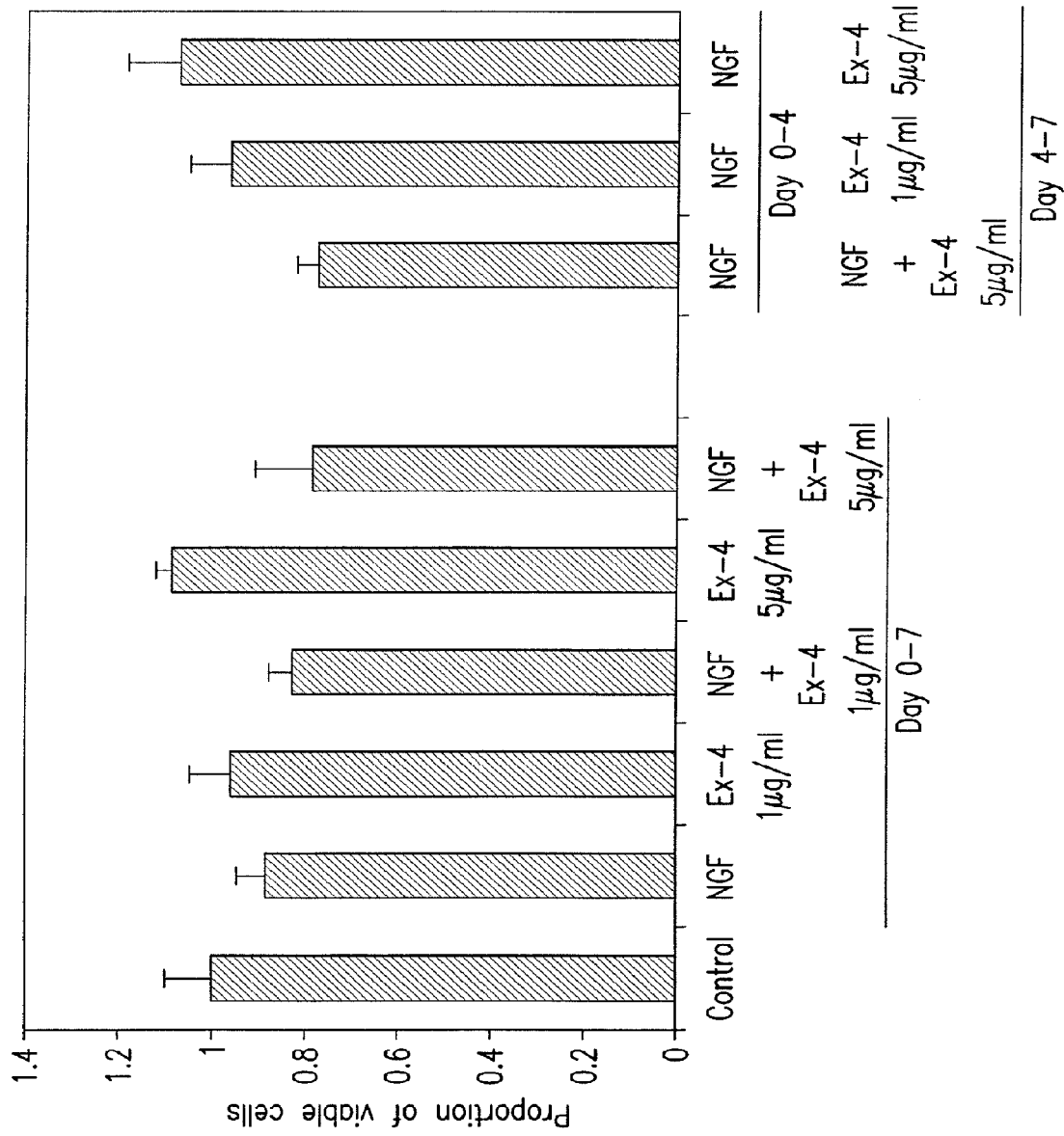

FIG. 13 shows the effect of exendin-4 treatment on NGF-mediated cell death. Combination treatments were carried out for a total of 7 days, in the presence or absence of 50 ng/ml NGF, with or without exendin-4 (at 1 or 5 mg/ml). Cells were subsequently harvested and allowed to rejuvenate in complete media for an additional 3 days. Cell survival is presented as the proportion of viable cells (by MTT method) on day 10. Vertical error bars represent ±standard error of four individual experimental values.

Figure 14:
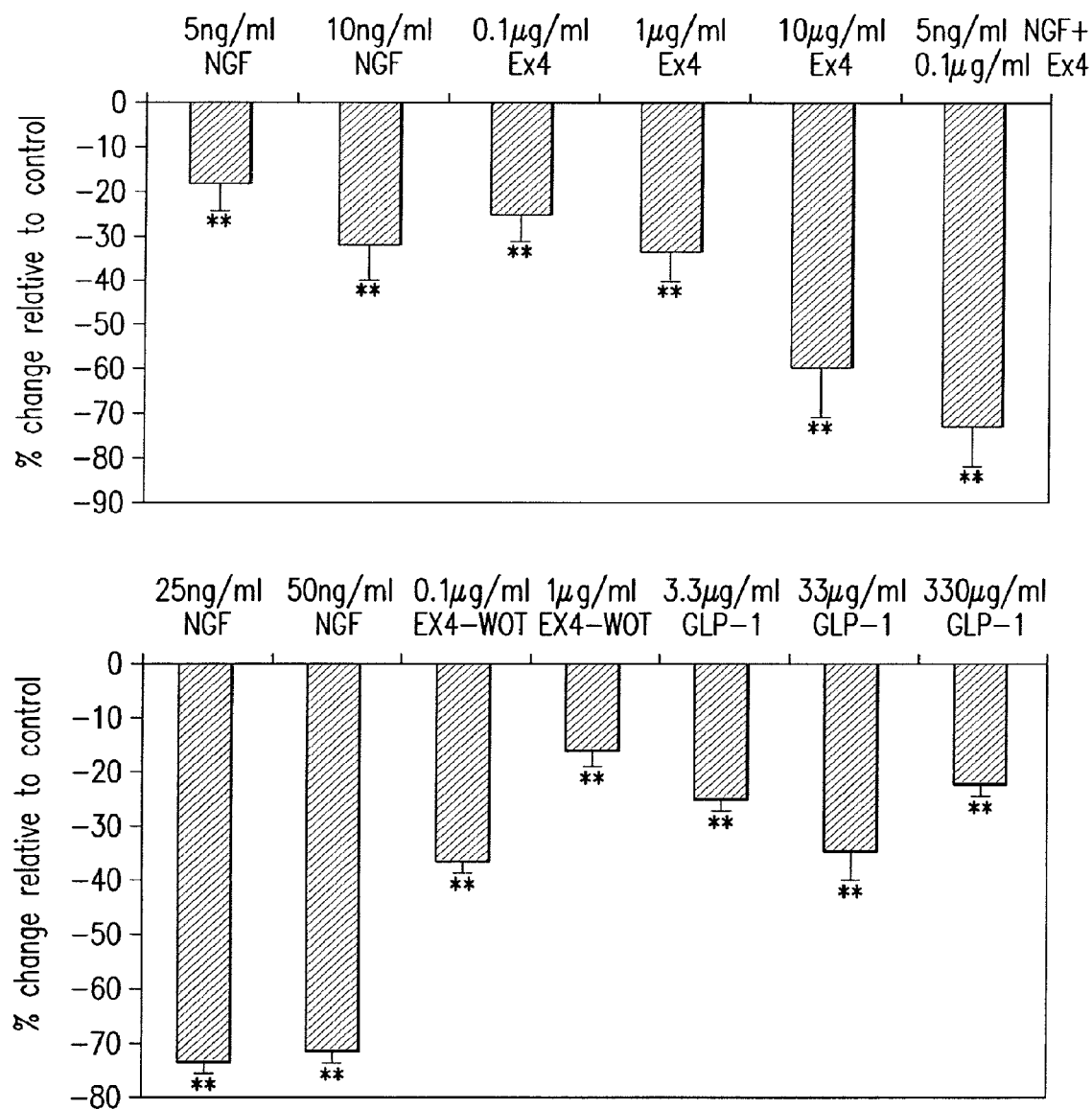

FIG. 14 shows densitometric quantification of the synaptophysin protein extracted from NGF, exendin-4, exendin-4 WOT and GLP-1 treated PC12 cells. Protein bands obtained from cell lysate samples were analyzed by Western blotting and immunoprobed with the synaptophysin monoclonal antibody, which stains neurosecretory vesicles. Synaptophysin was used as a marker of differentiation. Density of the synaptophysin protein is presented as the percent difference from untreated. Vertical error bars represent ±standard error of three individual experimental values conducted at separate time intervals. Significant difference from untreated: ** p<0.01.

Figure 15:
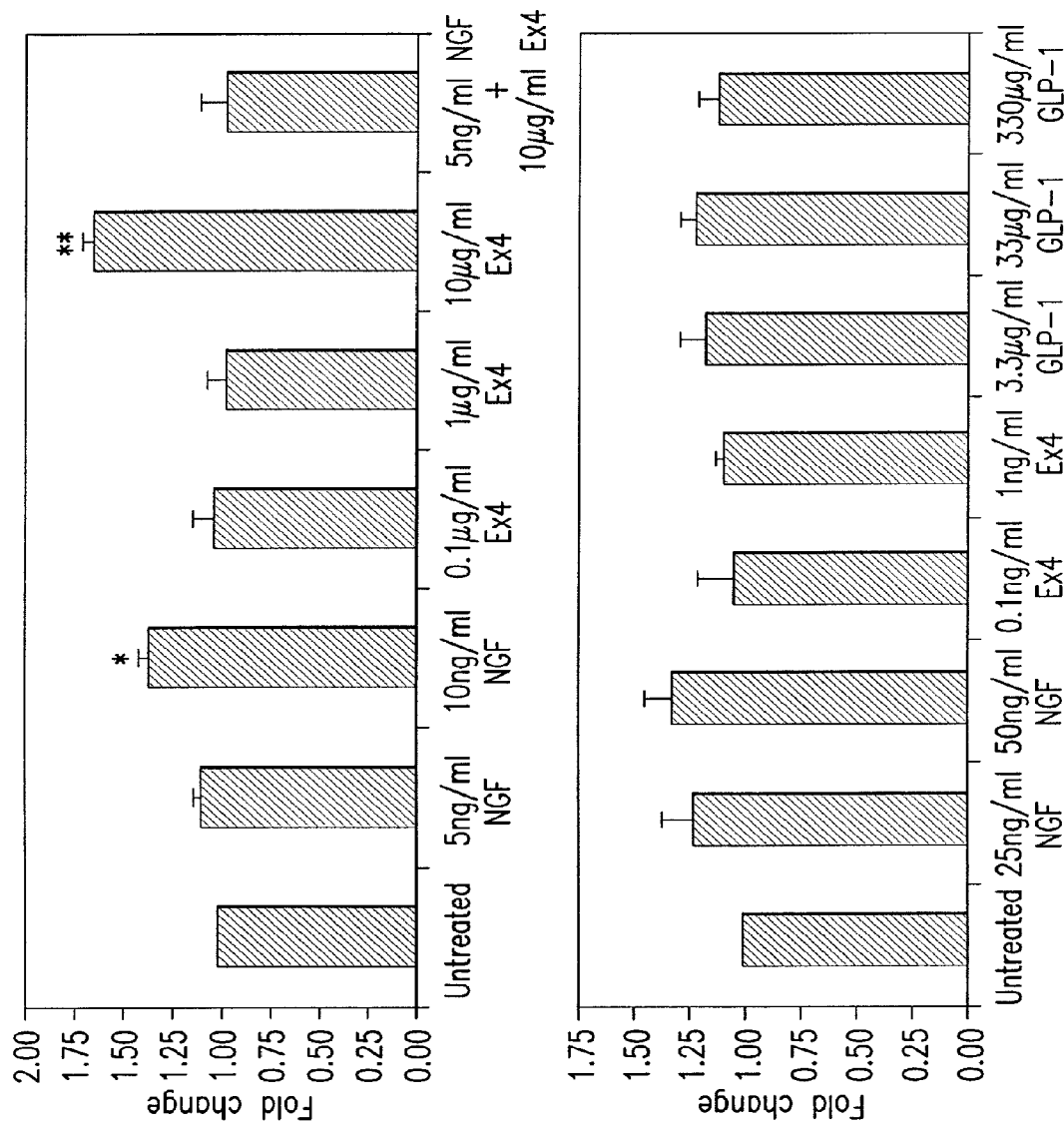

FIG. 15 shows fold increases in lactate dehydrogenase (LDH) levels in the conditioned medium of PC12 cells following treatment with NGF, exendin-4, exendin-4 WOT and GLP-1. LDH levels are a marker of cell viability, with elevated levels being associated with a loss of cell integrity. Vertical error bars represent ±standard error of the difference between the means of three individual experimental values conducted at separate time intervals. Significant difference from untreated: * p<0.05 and ** p<0.01.

FIG. 16 shows displacement of $^{125}$I-GLP-1 binding with cold GLP-1 (A), GLP-1 stimulated release of cAMP (B) and protection against glutamate-induced apoptosis (C) in cultured hippocampal neurons. $^{125}$I-GLP-1 binding to intact cultured hippocampal neurons was competed with various concentrations of GLP-1. The data are normalized to maximum values obtained in the presence of 1 µM GLP-1. Each data point represents the mean of two experimental values and is presented as the percentage of maximum binding in the absence of cold peptide. cAMP levels were assayed over 30 min incubation with 10 nM GLP-1 (B). Vertical error bars represent ±standard error of the mean of three individual experimental values. Treatment with 10 nM GLP-1 or 0.3 µM exendin-4 completely protected against the apoptotic effects of 10 µM glutamate (C). Cultures were treated overnight, fixed with 4% paraformaldehyde and stained with Hoechst 33342. The number of apoptotic nuclei were counted and the values are presented as the pooled mean of six individual dishes per treatment condition. Vertical error bars represent ±standard error of the difference between the means. Significant difference from control: * p<0.05,  p<0.01 and * p<0.001.

FIG. 17 shows choline acetyltransferase and glial fibrillary acidic protein immunoreactivity in the basal nucleus. ChAT-positive immunoreactivity, ipsilateral (A and C) and contralateral (B and D), to a partial ibotenic acid lesion. Panels A & B and C & D depict the left and right basal nucleus from individual animals which received vehicle infusion and GLP-1 infusion, respectively. ChAT—positive immunoreactivity in the ipsilateral basal nucleus in an animal which received vehicle infusion (A) was substantially lower than that in the ipsilateral basal nucleus in an animal which received GLP-1 infusion (C). Glial fibrillary acidic protein (GFAP) immunoreactivity, a marker for reactive astrocytes produced in response to injury, demonstrated areas of positive immunoreactivity surrounding the site of cannula implantation and lining of the lateral ventricle in the vicinity of the site of infusion. Interestingly, infusion of GLP-1 produced an elevated glial reaction in the basal nucleus on the infusion side (F) than that apparent as a result of the lesion (E) or after vehicle infusion.

Figure 18:
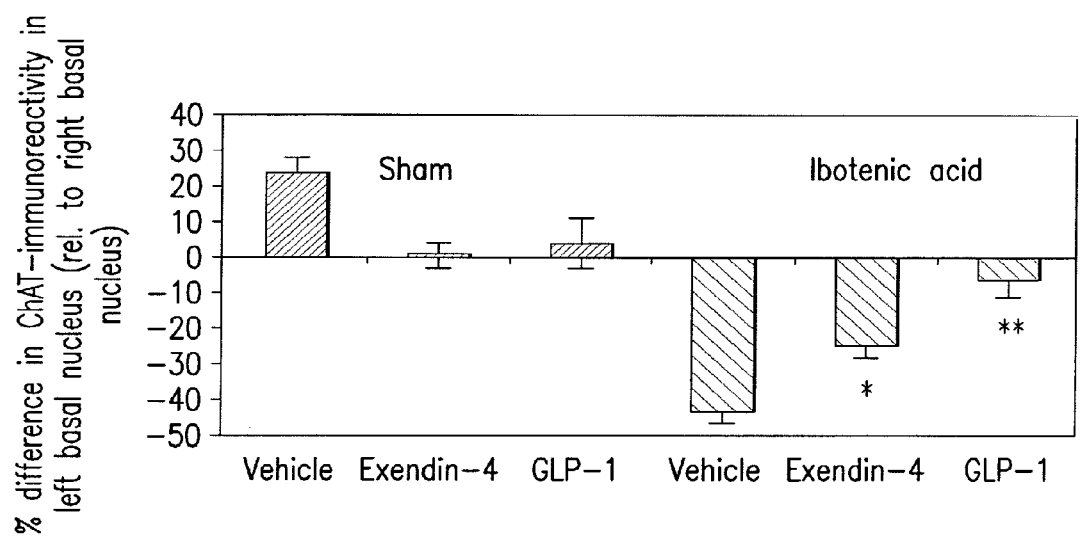

FIG. 18 shows percentage of difference in the Abercrombie corrected number of ChAT-immunoreactive cell bodies in the ipsilateral basal nucleus (lesion side) relative to the intact contralateral basal nucleus in sham and ibotenic acid animals receiving intracerebroventricularly (i.c.v.) infusion of vehicle (artifical CSF: aCSF), exendin-4 or GLP-1. Vertical error bars represent the standard error of the difference between the means. Significant difference from ibotenic acid vehicle group; * p<0.05 and ** p<0.01.

Figure 19:
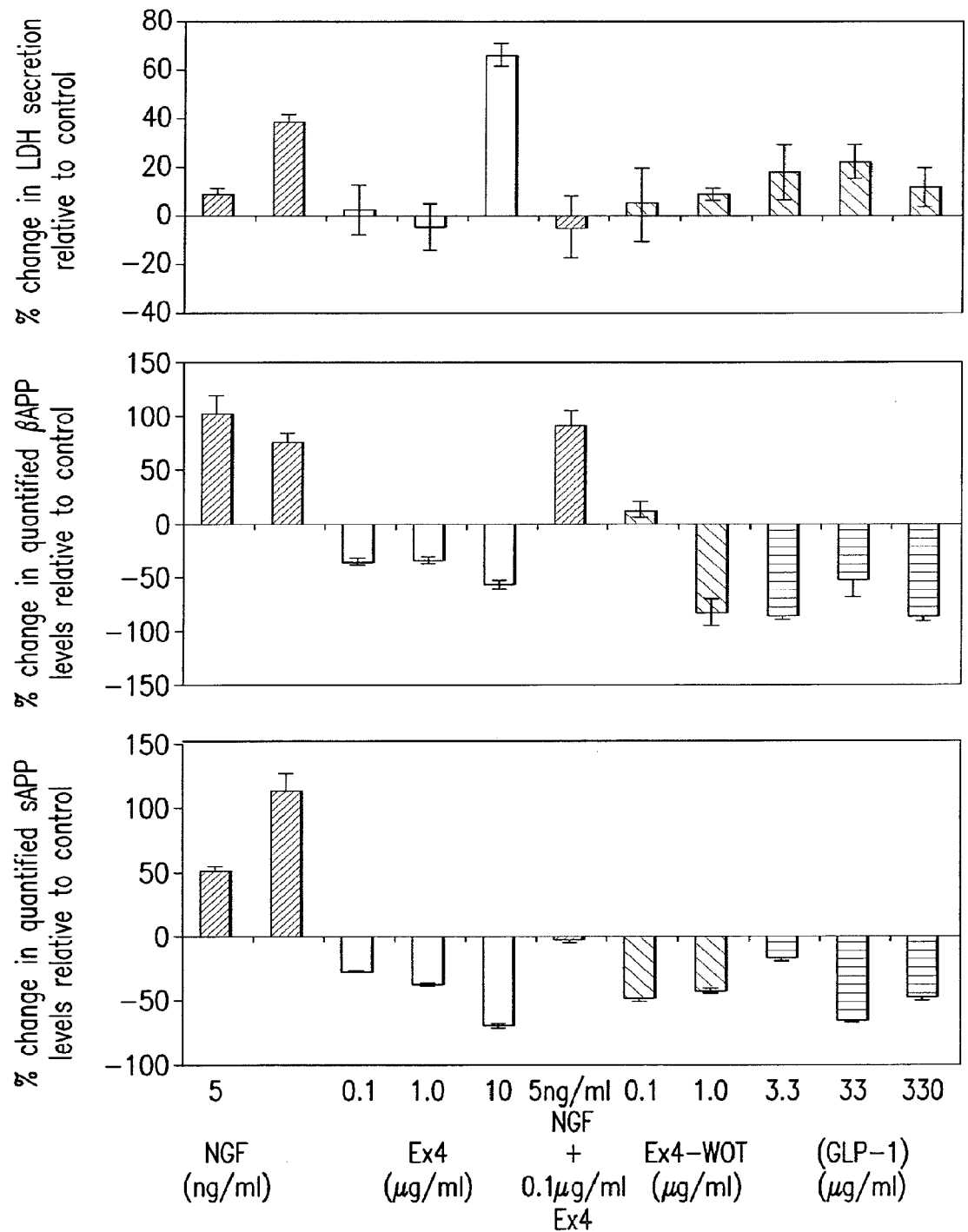

FIG. 19 shows that treatment of PC12 cells with GLP-1 and analogues significantly decreased βAPP and sAPP protein levels without cellular dysfunction. Treatment with NGF, exendin-4, exendin-4 WOT and GLP-1 was not associated with cellular dysfunction as determined by measurement of LDH levels from conditioned media samples compared with media standards (panel A). Densitometric quantification of the immunoprobed proteins are presented as the mean percent change in expression of βAPP derivatives from cell lysates samples (panel B) and soluble sAPP from conditioned media samples (panel C) taken on day 3 of treatment relative to untreated control samples cultured in low serum media alone. The treatment conditions illustrated along the x-axis are common to panels A, B and C. Vertical error bars represent standard error of 3 individual experimental values. Significant difference from untreated: * p<0.05 and ** p<0.01.

Figure 20:
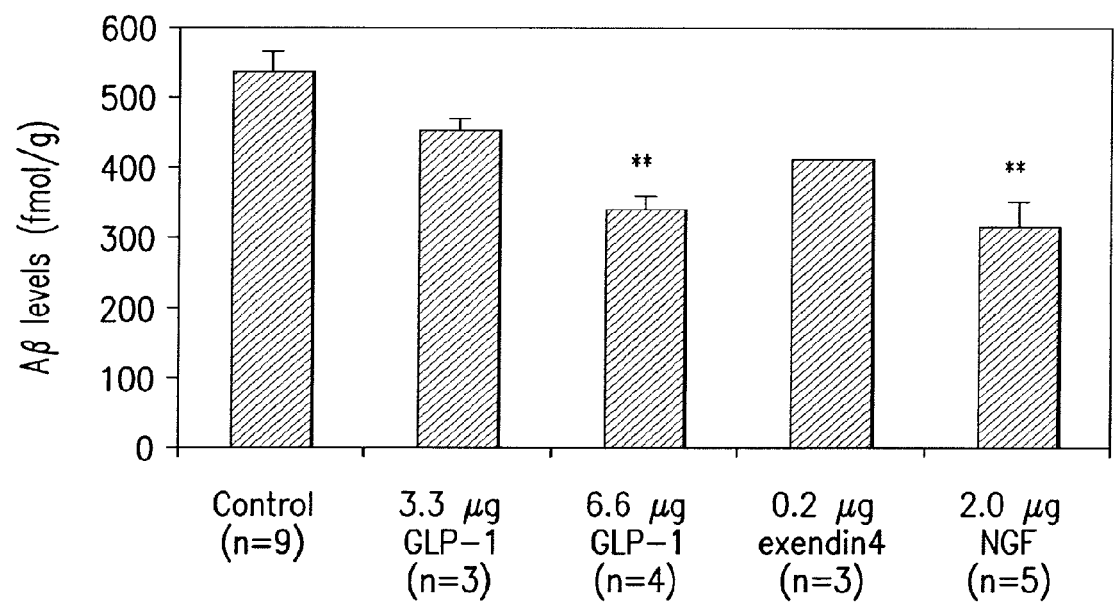

FIG. 20 shows GLP-1 treatment significantly reduced endogenous Aβ 1-40 levels in control mice. Control mice were infused i.c.v. with GLP-1 (3.3 µg and 6.6 µg), exendin-4 (0.2 µg), NGF (2 µg) and control (vehicle). Biochemical analysis of whole brain homogenates was carried out by sandwich ELISA for Aβ 1-40. Aβ values are expressed as the mean Aβ concentration in fmol/g ±SEM from treated and untreated animals. Significant difference from control: ** p<0.01.

Figure 21:
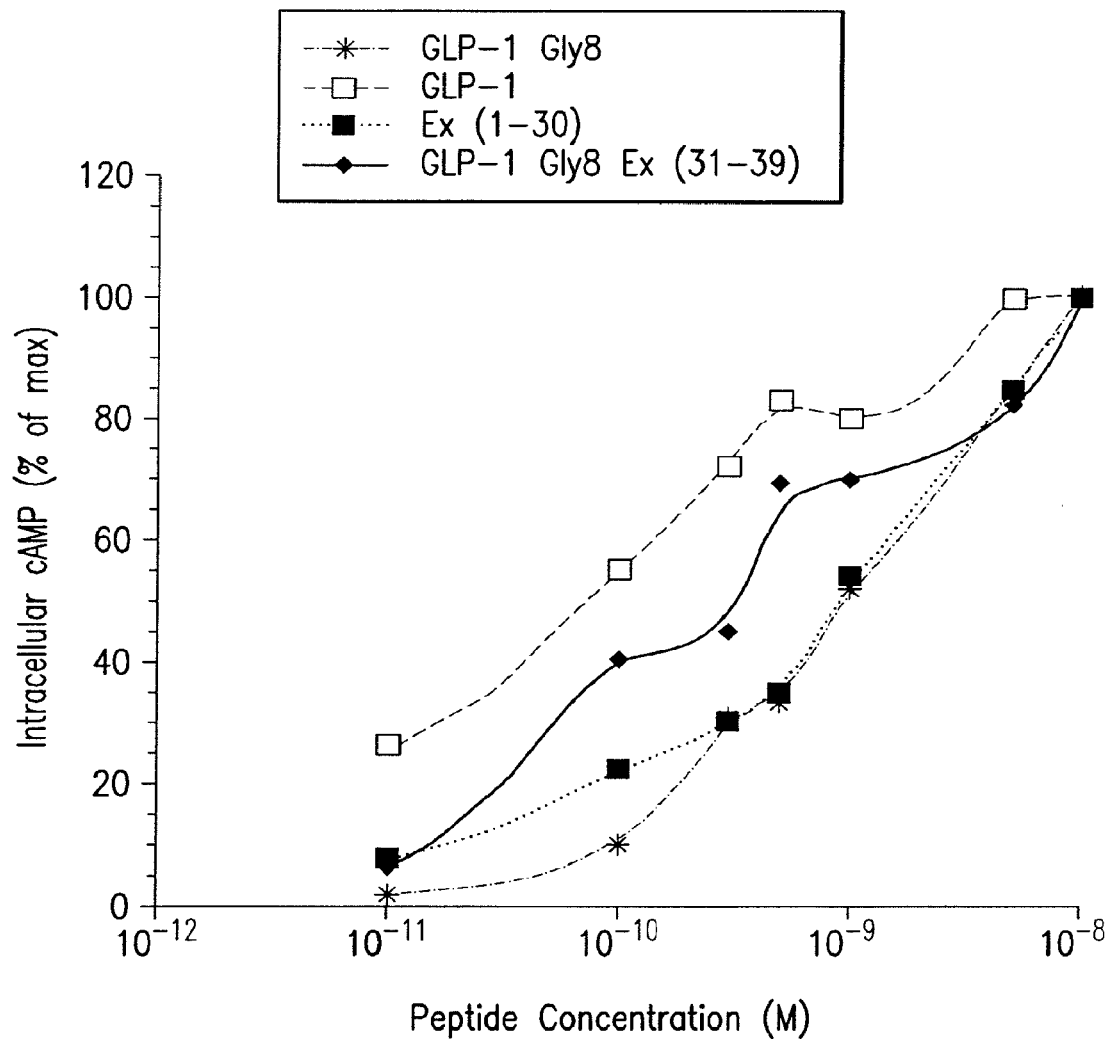

FIG. 21 shows dose response curves for some of the Ex-4 and GLP-1 Gly8 analogs. Intracellular cAMP levels were measured in Rin 1046-38 cells after treatment with the indicated concentrations of the peptides for 30 min at 37 C. The data are normalized to maximum values obtained in each experiment for each peptide.

Figure 22A:
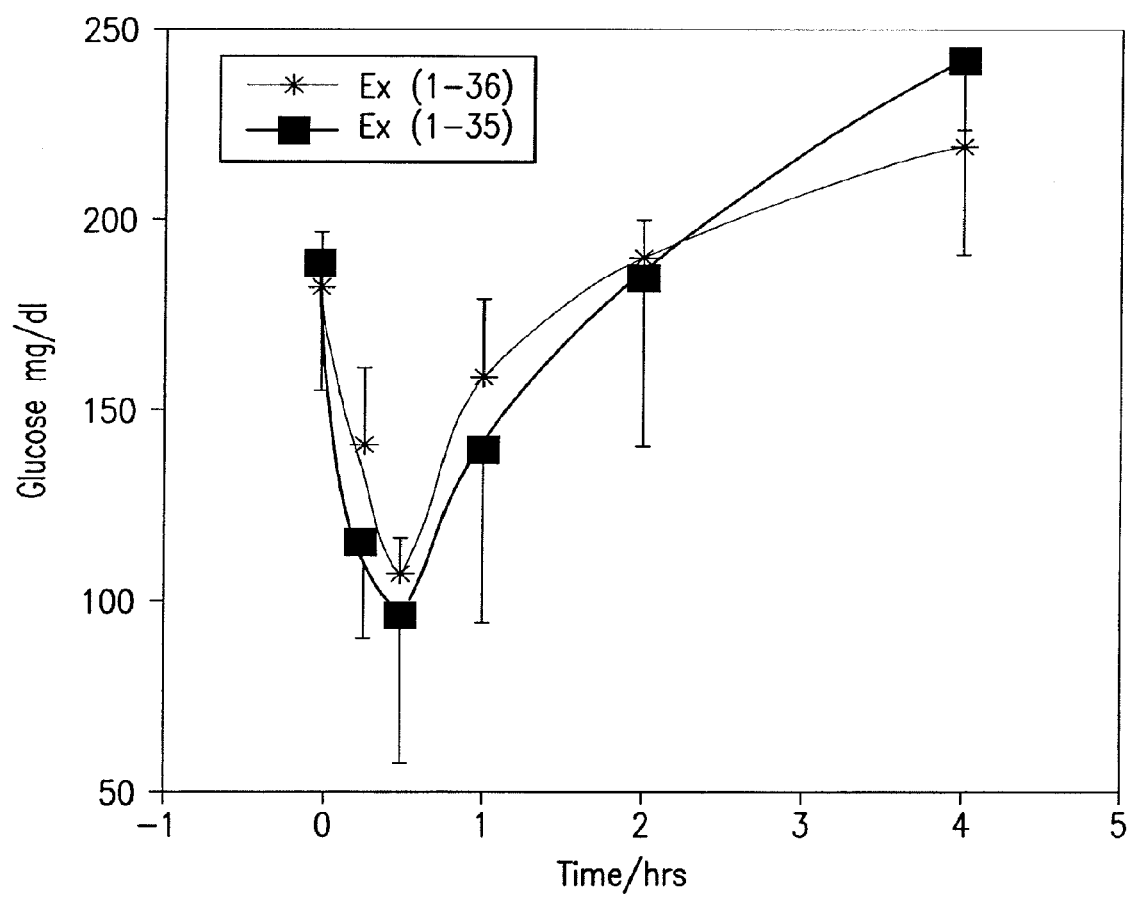
Figure 22B:
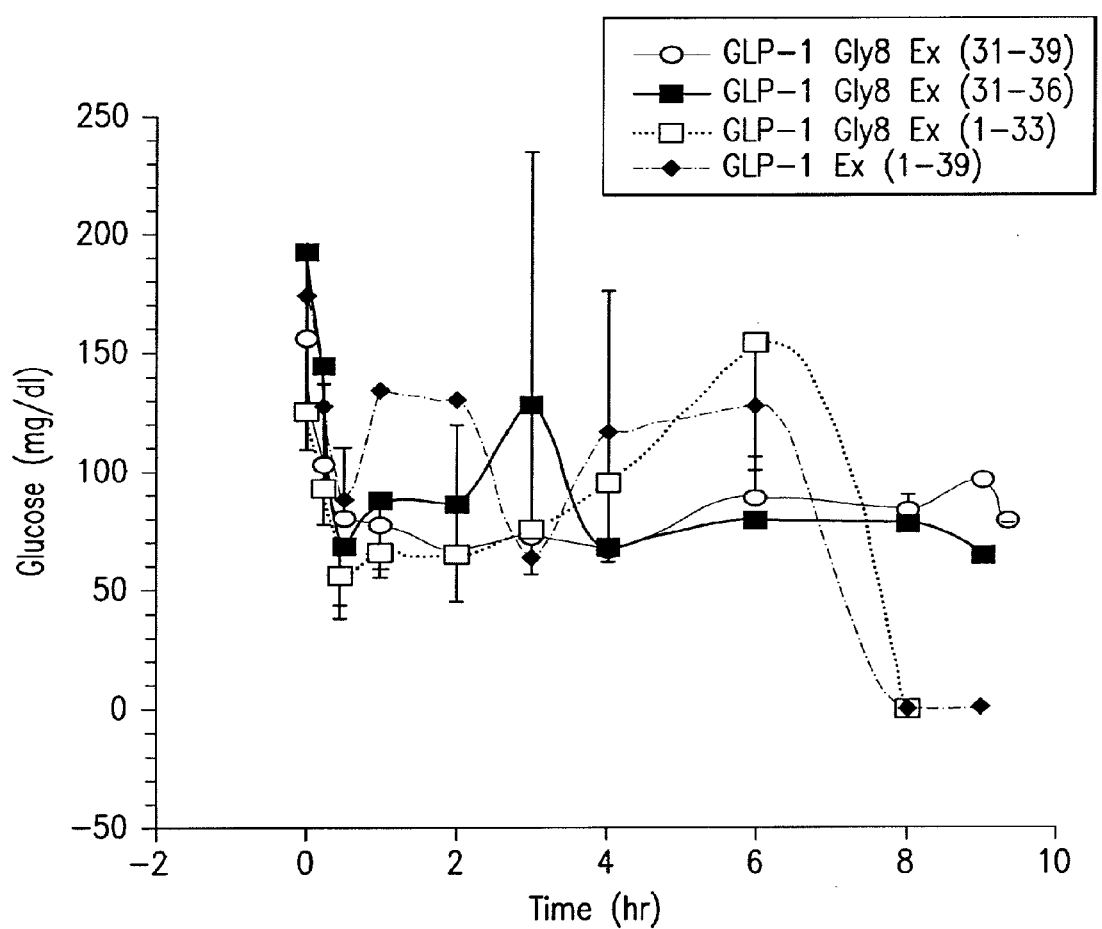

FIG. 22 shows the acute biological effects of the peptides on blood glucose levels. The results with Ex(1-36) (circle) and Ex(1-35)(square) are shown in FIG. 22A, and the results with additional peptides are shown FIG. 22B. Blood glucose and insulin levels were determined after an sc injection of 10 nmol/kg of each of the peptides to Zucker rats. The results are mean±SEM (n=4/group for FIG. 22A and n=3 for FIG. 22B).

Figure 23:
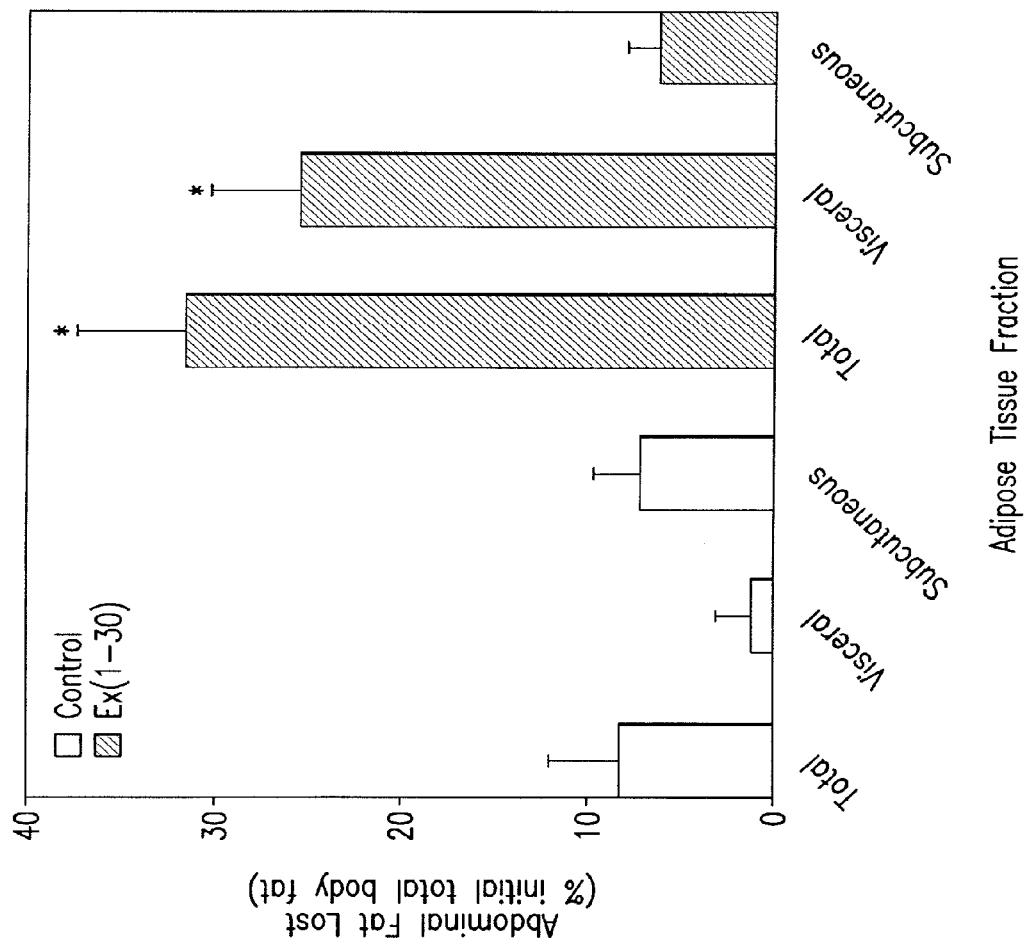

FIG. 23 shows the abdominal fat volume lost over 51 days in control (white bars) and Ex (1-30) treated animals (black bars). The values are expressed as a percentage of the initial total fat volume (0 days). For each group, the total fat lost, as well as the fat lost from the visceral and subcutaneous tissue fractions is shown. The data shows that there was a significantly greater volume of total fat and visceral fat lost in the Ex(1-30) treated animals than in the control animals. Both groups showed decreased total fat volume at the 51 day time point. In the control group, this loss was largely due to loss of fat from the subcutaneous fraction, which occurred to a similar extent in the treated animals. *P<0.05 Ex(1-30) vs control.

DESCRIPTION OF THE PREFERRED EMBODIMENTS

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific treatment regimens, or to particular purification procedures, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a polypeptide" includes mixtures of polypeptides, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, "about" refers to the given value ±10%.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

As used throughout, by "subject" is meant an individual. Preferably, the subject is a mammal such as a primate, and, more preferably, a human. Thus, the "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

The term "polypeptide" is used synonymously herein with the term "peptide." Both "polypeptide" and "peptide" include a series of naturally occurring or non-naturally occurring amino acids connected by peptide bonds.

By "isolated polypeptide" or "purified polypeptide" is meant a polypeptide that is substantially free from the materials with which the polypeptide is normally associated in nature or in culture. The polypeptides of the invention can be obtained, for example, by extraction from a natural source if available (for example, a mammalian cell), by expression of a recombinant nucleic acid encoding the polypeptide (for example, in a cell or in a cell-free translation system), or by chemically synthesizing the polypeptide. In addition, polypeptide may be obtained by cleaving full length polypeptides. When the polypeptide is a fragment of a larger naturally occurring polypeptide, the isolated polypeptide is shorter than and excludes the full-length, naturally-occurring polypeptide of which it is a fragment.

The invention relates to novel polypeptide analogues of GLP-1 and exendin-4. As used herein, "GLP-1" is used synonymously with GLP-1 7-36 amide, the amidated form of residues 7-36 of the complete GLP-1 sequence, and GLP-1 7-37. Residues of exendin-4 are aligned with GLP-1, residues 7-36, and numbered according to the numbering of the GLP-1 residues. Such a residue numbering convention is used throughout. See FIG. 1.

The polypeptides, in a preferred embodiment, are insulinotropic. By "insulinotropic" is meant that the polypeptides increase insulin synthesis, release or secretion in a glucose dependent manner as compared to levels of basal release in response to glucose alone. Such increase in insulin release preferably is at least 1.15, 1.25, 1.5, 2.0, 2.5, 3.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0 times greater than basal release. The increase in insulin release can be shown directly (e.g., by showing increased levels of insulin) or indirectly (e.g., by showing reduced levels of glucose or by showing increased levels of cAMP) either in vivo (e.g., by assaying blood glucose levels) or in vitro (e.g., by assaying the level of insulin in the culture medium) using assay methods known in the art.

Insulinotropic effects can be due to any one of several mechanisms, including, for example, an increase in the number of insulin positive cells. The insulinotropic polypeptides, for example, promote insulin release by promoting differentiation of stem cells into insulin-positive cells and by promoting de-differentiation of non-stem cells to a less differentiated state and then promoting differentiation into insulin-positive cells. As a second example, the insulinotropic effects may be caused by an increase in the amount of insulin synthesized and/or released by each insulin positive cell in a given period of time. Combined insulinotropic effects could also occur if the number of insulin positive cells is increased and the amount of insulin secreted by each cell is also increased.

By "basal release" is meant the amount of insulin released in response to a glucose stimulus in the absence of a second releasing agent.

By "insulin-positive cells" is meant any cells that have been shown to release insulin, including, for example, pancreatic islet cells, such as beta cells, or cell lines such as RIN 1048-36 cells, any cells designed to release insulin (e.g., genetically modified cells that contain insulin); or any cells that contain insulin.

By "analogue of GLP-1 or exendin-4" is meant modified GLP-1 and exendin amino acid sequences that show agonist properties (i.e., show one or more biological activities of GLP-1 or exendin-4). Such modifications include chimeric polypeptides that include one or more amino acid residues present in GLP-1 and one or more amino acid residues present in exendin-4. The modifications also include truncations of either GLP-1 or exendin-4 or the chimeric polypeptides. For example, a truncated chimeric polypeptide is exendin-4 7-36 with the G at position 36 replaced with the R in position 36 of GLP-1. The polypeptides of the present invention include one or more additional amino acids (i.e., insertions or additions), deletions of amino acids, or substitutions in the amino acid sequence of GLP-1 or exendin-4 without appreciable loss of functional activity as compared to GLP-1 or exendin-4. For example, the deletion can consist of amino acids that are not essential to the presently defined differentiating activity and the substitution(s) can be conservative (i.e., basic, hydrophilic, or hydrophobic amino acids substituted for the same) or non-conservative. Thus, it is understood that, where desired, modifications and changes may be made in the amino acid sequence of GLP-1 and exendin-4, and a protein having like characteristics still obtained. Various changes may be made in the amino acid sequence of the GLP-1 or exendin-4 amino acid sequence (or underlying nucleic acid sequence) without appreciable loss of biological utility or activity and possibly with an increase in such utility or activity.

The term "fragments" or "truncations" as used herein regarding GLP-1 or exendin-4 or polypeptides having amino acid sequences substantially homologous thereto means a polypeptide sequence of at least 5 contiguous amino acids of either GLP-1, exendin 4, or polypeptides having amino acid sequences substantially homologous thereto, wherein the polypeptide sequence has an insulinotropic function.

Other modifications include D-enantiomers, in which at least one naturally occurring L-configuration of an amino acid residue is replaced by the D-configuration of the amino acid residue.

The present invention contemplates the use of a spacer, such as a lateral spacer. The term "lateral spacer" is defined as a compound that is incorporated within the amino acid sequence by chemical bonds, whereby the compound increases the distance between two or more amino acid residues in order to reduce or eliminate the cleavage (e.g., by DPP 1V) of the amino acid sequence at or near that position. For example, in the sequence A-X-B, where A and B are amino acid residues and X is the lateral spacer, cleavage of the sequence by an enzyme is reduced or eliminated when compared to the sequence in the absence of the lateral spacer (A-B). Preferably 1 to 4 compounds can be incorporated into the amino acid sequence as the lateral spacer. Thus, 1, 2, 3, or 4 compounds are inserted in various embodiments.

In general, the lateral spacer is any compound that can form a peptide bond with an amino acid, i.e., contains at least one amino group and at least one carboxyl group ($CO_2^-$), where the carboxyl group can be a carboxylic acid or the ester or salt thereof. In one embodiment, the lateral spacer has the formula $H_2N—R^1—CO_2H$ (I), wherein $R^1$ comprises a substituted or unsubstituted, branched or straight chain $C_1$ to $C_{20}$ alkyl group, alkenyl group, or alkynyl group; a substituted or unsubstituted $C_3$ to $C_8$ cycloalkyl group; a substituted or unsubstituted $C_6$ to $C_{20}$ aryl group; or substituted or unsubstituted $C_4$ to $C_{20}$ heteroaryl group. In another embodiment, $R^1$ can be represented by the formula $(CH_2)_n$, where n is from 1 to 10. In a preferred embodiment, $R^1$ is $(CH_2)_3$ (3-aminopropionic acid) or $(CH_2)_5$ (6-aminohexanoic acid).

The present invention provides a purified polypeptide, wherein the polypeptide comprises a modified GLP-1 or exendin-4 sequence, or an anlogue thereof, with a spacer between the amino acid residues comparable to residues 7 and 8 (designated in the case of GLP-1 with a Aha spacer, for example, "GLP-1 Aha$^8$") or residues 8 and 9 (designated in the case of GLP-1 with a Aha spacer, for example, "GLP-1Aha$^9$") of GLP-1. The lateral spacer, in one embodiment, is one or more aminoproprionic acid residues. In one embodiment, the spacer is a 6-aminohexanoic acid spacer and the 6-aminohexanoic acid spacer comprises less than four 6-aminohexanoic acid residues. The polypeptide, for example, can comprise GLP-1 7-36 with one or more 6-aminohexanoic acid residues between residues 7 and 8 (i.e., GLP-1 Aha$^8$) or can comprise GLP-1 7-36 with one or more 6-aminohexanoic acid residues between residues 8 and 9. The polypeptide can comprise GLP-1 7-36 with two or more 6-aminohexanoic acid residues between residues 7 and 8 (i.e., GLP-1 Aha$^8$) or can comprise GLP-1 7-36 with two or more 6-aminohexanoic acid residues between residues 8 and 9. The polypeptide, for example, can comprise GLP-1 7-36 with three or more 6-aminohexanoic acid residues between residues 7 and 8 (i.e., GLP-1 Aha$^8$) or can comprise GLP-1 7-36 with three or more 6-aminohexanoic acid residues between residues 8 and 9. More specifically, in one embodiment the polypeptide comprises the amino acid sequence of SEQ ID NO:8, SEQ ID NO:22, or SEQ ID NO:23. In other embodiments, the polypeptide comprises the amino acid sequence of SEQ ID NO:42, SEQ ID NO:43, SEQ ID NO:44, SEQ ID NO:45, SEQ ID NO:46, SEQ ID NO:47, SEQ ID NO: 48, or SEQ ID NO:49. In alternative embodiments, the polypeptide comprises the amino acid sequence of SEQ ID NO:5, SEQ ID NO:6, SEQ ID NO:7, SEQ ID NO:8, SEQ ID NO:42, SEQ ID NO:43, SEQ ID NO:44, SEQ ID NO:45, SEQ ID NO:46, SEQ ID NO:47, SEQ ID NO:48, SEQ ID NO:9, SEQ ID NO:10, SEQ ID NO:11, SEQ ID NO:12, SEQ ID NO:13, SEQ ID NO:14, SEQ ID NO:15, SEQ ID NO:25, SEQ ID NO:33, wherein the amino acid sequence contains a spacer between the amino acid residues comparable to residues 7 and 8 or to residues 8 and 9 of GLP-1.

In a preferred embodiment, the polypeptide of the present invention has an insulinotropic effect that is comparable to the effect of an equimolar amount of GLP-1 or, in a more preferred embodiment, an insulinotropic effect that is comparable to the effect of an equimolar amount of exendin-4. By "comparable to the effect" is meant an effect that is within about 10-15% of the effect of GLP-1 or exendin-4. In an even more preferred embodiment, the polypeptide has an insulinotropic effect that exceeds the insulinotropic effect of either GLP-1 or exendin-4. By "exceeding the effect" of GLP-1 or exendin-4 is meant an increase in insulinotropic effect compared to GLP-1 or exendin-4, preferably an increase that is greater than about 10% of the effect of GLP-1 or exendin-4. Thus, in a preferred embodiment, the polypeptide of the present invention is as potent as GLP-1 or exendin-4, and in a more preferred embodiment is more potent that GLP-1 and, optionally, more potent than exendin-4.

In a preferred embodiment, the polypeptide of the present invention is longer acting than GLP-1. In a more preferred embodiment, the polypeptide is at least as long acting as exendin-4. In an even more preferred embodiment, the polypeptide is longer acting than exendin-4. By "longer acting" is meant that the polypeptide is more resistant than GLP-1 or exendin-4 to at least one degradative enzyme. For example, the preferred embodiment of the polypeptide of the present invention is more resistant to degradation by the enzyme dipeptidyl dipeptidase (DPP1V) than is GLP-1 and, optionally, more resistant than exendin-4. Such resistance to one or more degradative enzymes can be assessed directly by detecting the amount of degradation products (e.g., the amount of N-terminal degradation products) or the amount of un-cleaved polypeptide. Alternatively, the resistance to one or more degradative enzymes can be detected indirectly by assessing the reduction in insulinotropic effect over time following administration of a polypeptide of the invention. For example, as the degradative enzymes cleave the polypeptides of the invention, plasma insulin levels should decline after a single administration. In a preferred embodiment this decline would be slower than for GLP-1 and perhaps even slower than for exendin-4.

In a preferred embodiment, the polypeptide has reduced antigenicity as compared to exendin-4. Antigenicity can be assessed using routine methods, such as biological assays designed to assess neutralizing antibodies and polypeptide clearance.

In a preferred embodiment, the polypeptide has a higher binding affinity for the GLP-1 receptor than the binding affinity of GLP-1 for the GLP-1 receptor. In a more preferred embodiment, the polypeptide has a higher binding affinity for the GLP-1 receptor than the binding affinity of exendin-4 for the GLP-1 receptor.

In a preferred embodiment, the polypeptide stimulates intracellular cAMP levels over basal levels more than GLP-1. In an even more preferred embodiment, the polypeptide stimulates intracellular cAMP levels over basal levels more than exendin-4.

Specifically, the invention provides a purified polypeptide, the amino acid sequence of which comprises SEQ ID NO:5, SEQ ID NO:6, SEQ ID NO:7, SEQ ID NO:8, SEQ ID NO:42, SEQ ID NO:43, SEQ ID NO:44, SEQ ID NO:45, SEQ ID NO:46, SEQ ID NO:47, SEQ ID NO:48, SEQ ID NO:9, SEQ ID NO:10, SEQ ID NO:11, SEQ ID NO:12, SEQ ID NO:13, SEQ ID NO:14, SEQ ID NO:15, SEQ ID NO:25, SEQ ID NO:33. More specifically, the invention provides a purified polypeptide, the amino acid sequence of which consists essentially of SEQ ID NO:5, SEQ ID NO:6, SEQ ID NO:7, SEQ ID NO:8, SEQ ID NO:42, SEQ ID NO:43, SEQ ID NO:44, SEQ ID NO:45, SEQ ID NO:46, SEQ ID NO:47, SEQ ID NO:48, SEQ ID NO:9, SEQ ID NO:10, SEQ ID NO:11, SEQ ID NO:12, SEQ ID NO:13, SEQ ID NO:14, SEQ ID NO:15, SEQ ID NO:25, SEQ ID NO:33. Even more specifically, the invention provides a purified polypeptide, the amino acid sequence of which consists of SEQ ID NO:5, SEQ ID NO:6, SEQ ID NO:7, SEQ ID NO:8, SEQ ID NO:42, SEQ ID NO:43, SEQ ID NO:44, SEQ ID NO:45, SEQ ID NO:46, SEQ ID NO:47, SEQ ID NO:48, SEQ ID NO:9, SEQ ID NO:10, SEQ ID NO:11, SEQ ID NO:12, SEQ ID NO:13, SEQ ID NO:14, SEQ ID NO:15, SEQ ID NO:25, SEQ ID NO:33.

Also, the invention provides a purified polypeptide, the amino acid sequence of which comprises SEQ ID NO:3, 4, 16, 17, 18, 19, 20, 21, 22, 23, 24, 26, 27, 28, 29, 30, 31, 32, 34, 35, 36, 37, 38, 39, 40, or 41. More specifically, the invention provides a purified polypeptide, the amino acid sequence of which consists essentially of SEQ ID NO:3, 4, 16, 17, 18, 19, 20, 21, 22, 23, 24, 26, 27, 28, 29, 30, 31, 32, 34, 35, 36, 37, 38, 39, 40, or 41. Even more specifically, the invention provides a purified polypeptide, the amino acid sequence of which consists of SEQ ID NO:3, 4, 16, 17, 18, 19, 20, 21, 22, 23, 24, 26, 27, 28, 29, 30, 31, 32, 34, 35, 36, 37, 38, 39, 40, or 41.

The polypeptides of the invention can be prepared using any of a number of chemical polypeptide synthesis techniques well known to those of ordinary skill in the art including solution methods and solid phase methods. Solid phase synthesis in which the C-terminal amino acid of the polypeptide sequence is attached to an insoluble support followed by sequential addition of the remaining amino acids in the sequence is one synthetic method for preparing the polypeptides. Techniques for solid phase synthesis are described by Merrifield et al., *J. Am. Chem. Soc.* 85:2149-2156 (1963). Many automated systems for performing solid phase peptide synthesis are commercially available.

Solid phase synthesis is started from the carboxy-terminal end (i.e., the C-terminus) of the polypeptide by coupling a protected amino acid via its carboxyl group to a suitable solid support. The solid support used is not a critical feature provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for use as solid supports are well known to those of skill in the art and include, but are not limited to, the following: halomethyl resins, such as chloromethyl resin or bromomethyl resin; hydroxymethyl resins; phenol resins, such as 4-(a-[2,4-dimethoxyphenyl]-Fmoc-aminomethyl)phenoxy resin; tert-alkyloxycarbonyl-hydrazidated resins; and the like. Such resins are commercially available and their methods of preparation are known to those of ordinary skill in the art.

The acid form of the peptides may be prepared by the solid phase peptide synthesis procedure using a benzyl ester resin as a solid support. The corresponding amides may be produced by using benzhydrylamine or methylbenzhydrylamine resin as the solid support. Those skilled in the art will recognize that when the BHA or MBHA resin is used, treatment with anhydrous hydrofluoric acid to cleave the peptide from the solid support produces a peptide having a terminal amide group.

The α-amino group of each amino acid used in the synthesis should be protected during the coupling reaction to prevent side reactions involving the reactive α-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the peptide synthesis. Protecting groups are well known to those of skill in the art. See, for example, *The Peptides: Analysis, Synthesis, Biology, Vol.* 3: *Protection of Functional Groups in Peptide Synthesis* (Gross and Meienhofer (eds.), Academic Press, N.Y. (1981)).

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the α-amino protecting group, and must be removable after completion of the peptide synthesis under conditions that will not alter the structure of the peptide.

Coupling of the amino acids may be accomplished by a variety of techniques known to those of skill in the art. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodiimide (DCC) or N,N'-diisopropylcarbodiimide (DIPCDI). Frequently, hydroxybenzotriazole (HOBt) is employed as a catalyst in these coupling reactions.

Generally, synthesis of the peptide is commenced by first coupling the C-terminal amino acid, which is protected at the N-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(a-[2,4-dimethoxyphenyl]-Fmoc-amino-methyl)phenoxy resin using N,N'-dicyclohexylcarbodiimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Novartis (Switzerland) or Bachem (Torrance, Calif.)). As an alternative to the stepwise addition of individual amino acids, appropriately protected peptide fragments consisting of more than one amino acid may also be coupled to the "growing" peptide. Selection of an appropriate coupling reagent, as explained above, is well known to those of skill in the art.

Each protected amino acid or amino acid sequence is introduced into the solid phase reactor in excess and the coupling is carried out in a medium of dimethylformamide (DMF), methylene chloride ($CH_2Cl_2$), or mixtures thereof. If coupling is incomplete, the coupling reaction may be repeated before deprotection of the N-amino group and addition of the next amino acid. Coupling efficiency may be monitored by a number of means well known to those of skill in the art. A preferred method of monitoring coupling efficiency is by the ninhydrin reaction. Peptide synthesis reactions may be performed automatically using a number of commercially available peptide synthesizers such as the Biosearch 9500™ synthesizer (Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The peptides can be isolated and purified from the reaction mixture by means of peptide purification well known to those of skill in the art. For example, the peptides may be purified using known chromatographic procedures such as reverse phase HPLC, gel permeation, ion exchange, size exclusion, affinity, partition, or countercurrent distribution.

The polypeptides of the invention can also be prepared by other means including, for example, recombinant techniques. Examples of appropriate cloning and sequencing techniques, and instructions sufficient to direct persons of skill through many cloning exercises are found in Sambrook et al. (1989) *Molecular Cloning—A Laboratory Manual* (2nd ed.) Vol. 1-3, Cold Spring Harbor Laboratory, Cold Spring Harbor Press, NY, (Sambrook).

The invention further provides a method of treating a subject with diabetes, comprising administering to the subject the polypeptide of the invention in an amount that has an insulinotropic effect. By "diabetes" is meant diabetes mellitus. The method of the present invention is considered to be useful in the treatment of a subject having type 2 diabetes. The method of the present invention could be of use in other forms of diabetes (including, for example, type 1 diabetes) when the polypeptide promotes non-insulin producing cells to produce insulin.

The polypeptides of the present invention also have uses in the nervous system. In one embodiment, the polypeptides are neurotrophic (i.e. promoting proliferation, differentiation or neurite outgrowth) or neuroprotective (i.e. rescuing neuron cells or reducing neuronal cell death). Thus, the invention further relates to a method of reducing neuronal death, comprising contacting one or more neurons with a polypeptide comprising GLP-1, exendin-4, or a neuroprotective or neurotrophic GLP-1 or exendin-4 analogue. Neuronal death may occur, for example, with mechanical injury (e.g., trauma or surgery), toxic injury, neurodegenerative disease, apoptosis, and peripheral neuropathy. One skilled in the art would recognize that rescuing neurons (i.e., promoting viability of cells that show signs of cell death) and reducing neuronal death (i.e., promoting viability of cells that do not show signs of cell death) may be desired. For example, treatment with a compound that reduced neuronal death would be useful in treating an explant or culture of neuronal cells, prior to subsequent transplantation. Also, such treatment could be used to rescue neurons and reduce neuronal death following a stroke, brain or spinal cord injury, nerve injury, or neurotoxic injury. Furthermore, rescuing neurons or reducing neuronal death would be useful in the treatment of neurodegenerative condition or disease diseases, including, for example, Alzheimer's disease, Parkinson's disease, Huntington's disease, amyotrophic lateral sclerosis, multiple sclerosis, and peripheral neuropathy.

The invention also relates to a method of promoting neuronal differentiation or proliferation, comprising contacting one or more neurons or neuronal precursor cells with a polypeptide comprising GLP-1, exendin-4, or a differentiation-inducing or proliferation-inducing GLP-1 or exendin-4 analogue. Differentiation involves a transition from a cell state in which the cell lacks neuronal characteristics (e.g., lacks characteristics such as a distinct nucleolus, neuronal processes, extensive rough endoplasmic reticulum, expression of neuronal markers) to a cell state characterized by a neuronal phenotype. By neuronal proliferation is meant that stem cells or cells of neuronal lineage divide and/or differentiate into neurons. The effect of either differentiation or proliferation is an increase in the number of neurons. By "an increase in the number of neurons" is meant an addition of neurons to the total number of all neurons present. Thus, the rate of neuronal cell death may exceed the rate of differentiation or proliferation, but the addition of new neurons is still considered to be an increase over the total neurons and such an increase in number, even in the absence of an increase in the total number of living neurons, could still have therapeutic advantages.

The present invention also relates to a method of reducing formation or accumulation of amyloid β protein, comprising contacting one or more neurons with a polypeptide comprising GLP-1, exendin-4, or a GLP-1 or exendin-4 analogue that affects β-amyloid precursor protein metabolism. Such a method could be useful in lowering levels of amyloid protein or in preventing the deposition of amyloid protein, which is observed in senile plaques in a subject with Alzheimer's Disease. The method of the present invention could reduce formation or accumulation of amyloid β protein by acting at various points in the processing of β-amyloid precursor protein. For example, the polypeptide may decrease synthesis of β-amyloid precursor protein, promote cleavage of β-amyloid precursor protein within the amyloid β protein region, increase secretion of soluble β-amyloid precursor protein, decrease secretion of amyloid β protein, or increase degradation of amyloid β protein.

The present invention also relates to a method of promoting growth of neuronal processes, comprising contacting one or more neurons with a polypeptide comprising GLP-1, exendin-4, or a process-promoting GLP-1 or exendin-4 analogue. By "growth of neuronal processes" is meant either an increase in the number of neuronal processes off of the soma, an increase in the complexity of neuronal processes (usually due to an increase in the number of branch points of axons or dendrites) or an increase in length of the processes. The growth of neuronal processes may be desired in many contexts, including for example, following a peripheral nerve injury or an injury to the central nervous system where optimization of regenerative capacity is desired. Also, in neurodegenerative conditions, the existing neurons may be able to compensate for neruonal death with an enriched field of processes.

The present invention also relates to a method of treating a subject with a neurodegenerative condition or of reducing one or more symptoms of a neurodegenerative condition in a subject, comprising administering to the subject a therapeutically effective amount of a polypeptide comprising GLP-1, exendin-4, or a therapeutically effective GLP-1 or exendin-4 analogue. More specifically, the treatment could be directed to neurodegenerative conditions selected from the group consisting of Alzheimer's disease, Parkinson's disease, Huntington's disease, amyotrophic lateral sclerosis, stroke, multiple sclerosis, brain injury, spinal cord injury, and peripheral neuropathy.

Also, provided is a method of treating a subject with a neurotoxic injury or of reducing one or more symptoms of a neurotoxic injury in a subject, comprising administering to the subject a therapeutically effective amount of a polypeptide comprising GLP-1, exendin-4, or a therapeutically effective GLP-1 or exendin-4 analogue. Such administration could be before during or after the exposure to the neurotoxin. Neurotoxins include the neurotoxic form of amyloid β-peptide, camptothecin, glutamate, etoposide, anti-cancer drugs, vinca alkaloids, 3-nitrognognonic acid, MPTP, domoic acid, kainic acid, and ibotenic acid.

The contacting step in these neural methods is performed in vivo or in vitro depending upon the desired effect. For example, neurons in culture can be treated prior to or after manipulation in culture that might cause neuronal death. Also, neurons in situ in the nervous system can be treated prior to or after exposure to a trigger that causes neuronal death. In a transplant paradigm, for example, the donor neurons to be transplanted might be treated in culture and then the transplantation area of the brain or spinal cord can be treated to prevent neuronal death of the recipient's neurons and of the transplanted neurons.

The polypeptides related to uses in the nervous system include polypeptides comprising GLP-1, exendin-4, and their biologically active analogues or agonists. Preferably, the analogues bind and activate the GLP-1/exendin-4 receptor. The polypeptides include for example polypeptides having the amino acid sequence of SEQ ID NO:1, 2, 5, 6, 7, 8, 9, 10, 11, 12, 13, 14, 15, 25, 33, 42, 43, 44, 45, 46, 47, or 48. Other examples include polypeptides having the amino acid sequence of SEQ ID NO:3, 4, 16, 17, 18, 19, 20, 21, 22, 23, 24, 26, 27, 28, 29, 30, 31, 32, 34, 35, 36, 37, 38, 39, 40, or 41.

Also provided by the present invention is a pharmaceutical composition comprised of a polypeptide of the invention, including for example, GLP-1, exendin-4, and their biologically active analogues or agonists, in combination with a pharmaceutically acceptable carrier.

One skilled in the art would recognize how to monitor the effectiveness of the treatment and how to adjust the treatment accordingly. For example, blood glucose levels could be monitored with normoglycemia being the optimal effect of treatment. If blood glucose levels are higher than preferred levels, then the amount of polypeptide administered should be increased, and, if blood glucose levels are lower than preferred levels, then the amount of polypeptide administered would be decreased.

The dosages of the polypeptides to be used in the in vivo method of the invention preferably range from about 0.1 pmoles/kg/minute to about 100 nmoles/kg/minute for continuous administration and from about 0.01 nmoles/kg to about 400 nmoles/kg for bolus injection. Preferably, the dosage of the polypeptide in in vivo methods range from about 0.01 nmoles/kg/min to about 10 nmoles/kg/min. The exact amount required will vary from polypeptide to polypeptide and subject to subject, depending on the species, age, and general condition of the subject, the severity of disease that is being treated, the particular polypeptide used, its mode of administration, and the like. Thus, it is not possible to specify an exact "insulinotropic amount" or an amount useful in treating neuronal disease or injury. However, an appropriate amount may be determined by one of ordinary skill in the art using only routine experimentation.

The polypeptides may be conveniently formulated into pharmaceutical compositions composed of one or more of the compounds in association with a pharmaceutically acceptable carrier. The compounds may be administered orally, intravenously, intramuscularly, intraperitoneally, topically, transdermally, locally, systemically, intraventricularly, intracerebrally, subdurally, or intrathecally. One skilled in the art would know to modify the mode of administration, the pharmacologic carrier, or other parameters to optimize the insulinotropic effects. The amount of active compound administered will, of course, be dependent on the subject being treated, the subject's weight, the manner of administration and the judgment of the prescribing physician.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc. See, e.g., *Remington's Pharmaceutical Sciences*, latest edition, by E.W. Martin Mack Pub. Co., Easton, Pa., which discloses typical carriers and conventional methods of preparing pharmaceutical compositions that may be used in conjunction with the preparation of formulations of the polypeptides and which is incorporated by reference herein.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

For topical administration, liquids, suspension, lotions, creams, gels or the like may be used as long as the active compound can be delivered to the surface of the skin.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Peptide Design and Synthesis

Figure 1A:
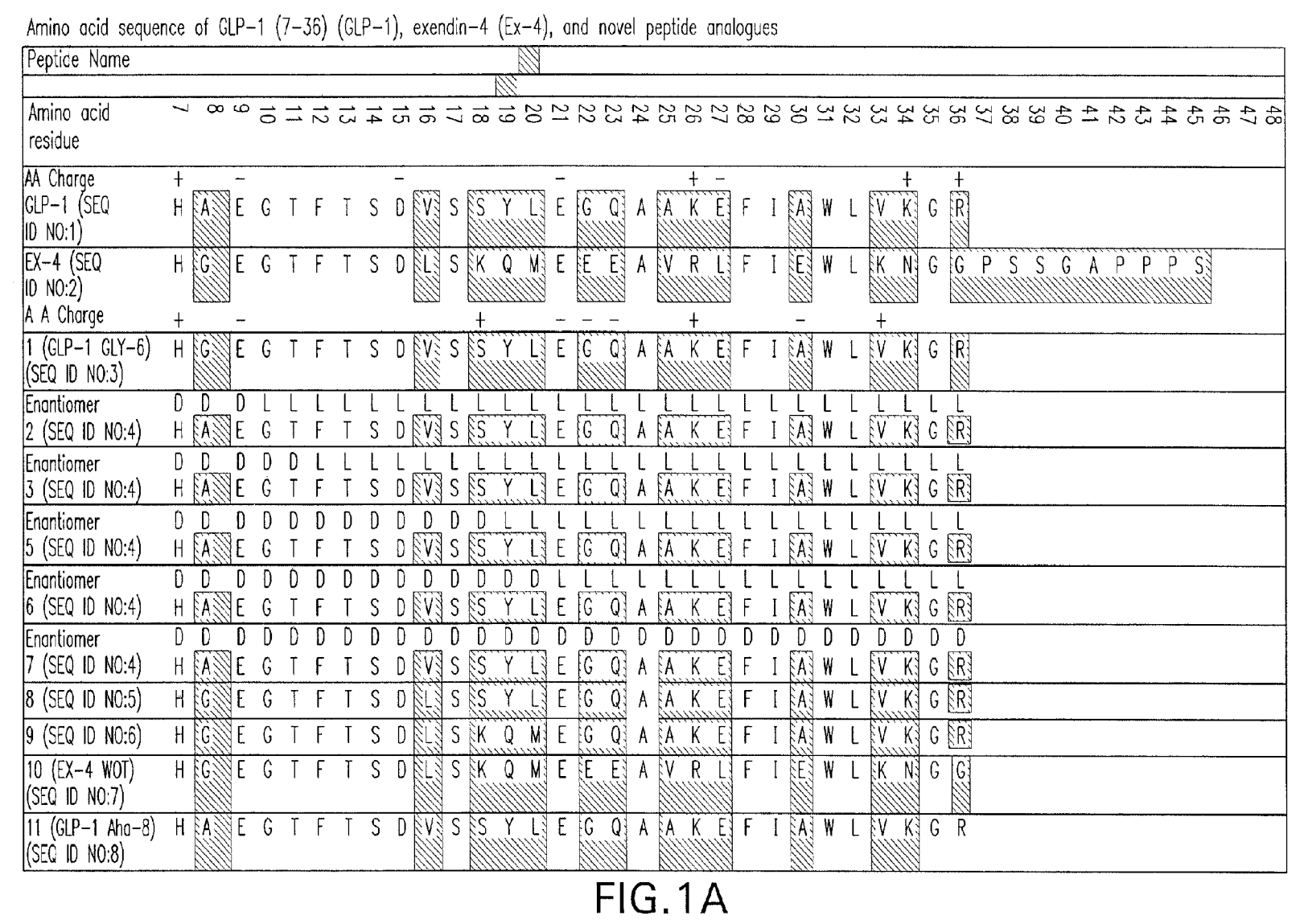

A series of chimeric peptides was designed that incorporated fundamental features of exendin-4 and GLP-1. The sequences of the 35 peptides are shown in FIG. 1, along with the sequence for GLP-1 (residues 7-36) and exendin-4 (residues 7-45 numbered according to the alignment of exendin-4 with the numbered GLP-1 residues). They were designed to (i) minimize the cleavage action of DDP1V between amino acids 8 and 9, (ii) assess the minimal requirement for insulinotropic action, and (iii) to assess which amino acid differences between exendin-4 and GLP-1 account for the former's 13-fold increase in potency versus GLP-1. The peptides shown in FIG. 1 utilized L- and D-amino acids in their synthesis.

Peptides were synthesized on a PEG-Polystyrene resin using Fmoc-derivatives of amino acids in a Applied Biosystems (Foster, Calif.) automated peptide synthesizer using piperidine-dimethyl formamide for deprotection and HOBt/HBTU for coupling. The finished peptides were cleaved from the resin using trifluoroacetic acid (TFA), precipitated with ether and subjected to purification using reverse phase HPLC on a C-18 hydrophobic resin in 0.1% TFA using an acetonitrile gradient. The purity of the final material was verified using reverse phase HPLC and the mass of the peptide was verified using mass spectrometry. All peptides were of 95% or greater purity.

Other peptides were designed to reduce cleavage by DPP1V using 2-amino hexanoic acid (6-aminohexanoic acid). See Table 2.

TABLE 2

Aha-Containing Peptides

| Peptide No. | Sequence | SEQ ID NO |
|---|---|---|
| 45 | H/Aha/AEGTFTSDVSSYLEGQAAKEFIAWLVKG RPSSGAPPPS | SEQ ID NO: 42 |
| 46 | H/Aha/AEGTFTSDVSSYLEGQAAKEFIAWLVKG RPSSGAPPPSGAP | SEQ ID NO: 43 |
| 47 | H/Aha/AEGTFTSDVSSYLEGQAAKEFIAWLVKG RPSSGAPPPSGAPPSS | SEQ ID NO: 44 |
| 48 | HA/Aha/EGTFTSDVSSYLEGQAAKEFIAWLVKG RPSSGAPPPS | SEQ ID NO: 45 |
|  | HA/Aha/EGTFTSDVSSYLEGQAAKEFIAWLVKG RPSSGAPPPSGAP | SEQ ID NO: 46 |
|  | HA/Aha/EGTFTSDVSSYLEGQAAKEFIAWLVKG RPSSGAPPPSGAPPSS | SEQ ID NO: 47 |
| 49 | Y/Aha/AEGTFISDYSIAMDKIHQQDFVNWLLAQ KGKKNDWKHNITQ | SEQ ID NO: 48 |
| 25 GLP-1(Aha$^9$)$_4$ | HA/(Aha)$_4$/EGTFTSDVSSYLEGQAAKEFIAWLVK GR | SEQ ID NO: 22 |
| 26 GLP-1(Aha$^9$)$_8$ | HA/(Aha)$_8$/EGTFTSDVSSYLEGQAAKEFIAWLVK GR | SEQ ID NO: 23 |

Example 2

Insulin Secretion In Vitro

RIN 1048-36 cells, a gift from Dr. Samuel A. Clark (Bio Hybrid Technologies, Shrewsbury, Mass.) were used to monitor the action of GLP-1, exendin-4 and analogs on insulin secretion. Cells were seeded at a density of $2.5 \times 10^5$ cells/cm$^2$ on glass coverslips placed on the bottom of 12-well dishes and grown for 48 h. Thereafter, they were preincubated for 2 periods of 30 min each with glucose-free buffer (containing mM: 140 NaCl, 5 KCl, 1 NaPO4, 1 MgSO4, 2 CaCl, 20 HEPES buffer (pH 7.4), and 0.1% bovine serum albumin) in a 37° C. humidified incubator. Thereafter, cells were incubated for 1 h at 37° C. in the presence of 1 mL of the same buffer with 5 mM glucose and peptide (1×10-8 M). GLP-1 and exendin-4 (1×10-8 M) were used as standards in all assays. After 1 h the medium was removed and stored at −80° C. prior to quantification of insulin levels by EIA (Crystal Chem, Chicago Ill.), and the cells were lysed with HCl (300 μl, 0.1M, 20 min, RT) for measurement of total protein using the Bradford method (Bio-Rad, Richmond, Calif.) with bovine γ-globulin as a standard.

Figure 2:
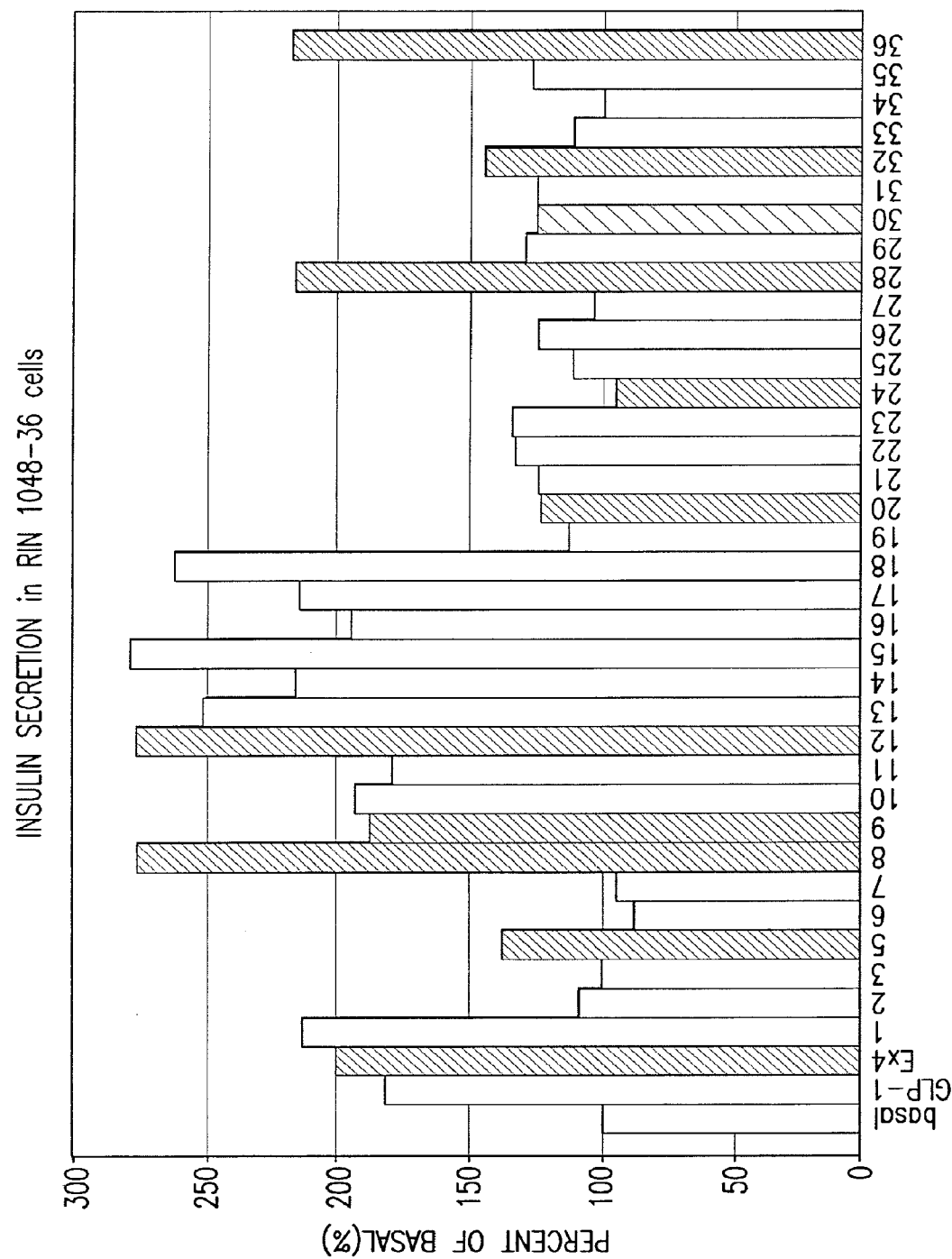
FIG. 2 shows a comparison in insulin secretion in RIN 1048-36 cells in the presence of GLP-1, exendin-4, and the synthetic polypeptides identified in FIG. 1. Levels are expressed as a percentage of basal levels.

As shown in FIG. 2, some of the amino acid modifications induced insulin secretion in a manner comparable to or exceeding inducement by GLP-1 or exendin-4. Several modifications were used to reduce recognition by DDP1V of the cleavage site between amino acid residues 8 and 9. The replacement of L-amino acids with the D-form near amino acid residues 8 and 9, however, proved ineffective, as shown with peptides 2, 3, and 5-7, because the peptides were incapable of inducing insulin secretion. Peptide 4 (not shown in FIG. 1), the GLP-1 sequence with residues 7-14 being D-amino acids, was similarly incapable of inducing insulin secretion. When an amino acid spacer was incorporated before or between residues 8 and 9, peptide 11 (SEQ ID NO:8) (having the 4 amino acid spacer before residue 8) potently induced insulin secretion whereas peptide 25 (SEQ ID NO: 22) (having a 4 amino acid spacer between residues 8 and 9) and peptide 26 (SEQ ID NO:23) (having an 8 amino acid spacer between residues 8 and 9) did not induce insulin secretion. Replacement of amino acid 8 (alanine:A) in GLP-1 with a small neutral amino acid, the peptide in the comparable position in exendin-4 (i.e., glycine:G) induced insulin secretion slightly more than exendin-4. See GLP-1 Gly$^8$ (SEQ ID NO:3).

Additional substitutions of the GLP-1amino acid residues with exendin-4 residues resulted in peptides that retained the ability to induce insulin secretion. For example, peptide 8 (SEQ ID NO:5) (having an A→G substitution at position 8 and a V→L substitution at position 16), peptide 9 (SEQ ID NO: 6) (having A→G, V→L, S→K, Y→Q, and L→M substitutions at position 8, 16, 18, 19, and 20, respectively), peptide 10 (Ex-WOT; SEQ ID NO:7) (having the same substitutions as in peptide 9 and additional having G→E, Q→E, A→V, K→R, E→L, A→E, V→K, K→N, and R→G substitutions at residues 22, 23, 25, 26, 27, 30, 33, 34, 36, respectively) all retained the ability to induce insulin secretion. In fact, peptide 8 (SEQ ID NO:5) had a substantially greater effect on insulin secretion than either GLP-1 or exendin-4.

The addition of the terminal 8-9 amino acids present on exendin-4 onto GLP-1, as in peptide 12 (SEQ ID NO:9), resulted in a peptide that also had a substantially greater effect on insulin secretion than either GLP-1 or exendin-4. When residue 8 in exendin-4 (i.e., glycine:G) was substituted with residue 8 of GLP-1 (i.e., alanine:A) and the terminal 9 amino acids of exendin-4 were retained, as in peptide 13 (SEQ ID NO:10), or removed, as in peptide 14 (SEQ ID NO:11), then both peptides retained the ability to induce insulin secretion; however, peptide 13 had a substantially greater effect than exendin-4 without the modifications.

Truncations of exendin-4 were also tested for their ability to induce insulin secretion. See peptides 15-24 (SEQ ID NOs:12-21). Only those peptides including more than 32 residues (i.e., peptides 15-18 (SEQ ID NOs:12-15)) induced insulin secretion. Of those truncation peptides that induced insulin secretion, peptide 15 (SEQ ID NO:12) (including residues up to and including residue 43) and peptide 18 (SEQ ID NO:15) (including residues up to and including residue 34) were the only ones that had an inducing effect that exceeded that of exendin-4 or GLP-1.

Modifications designed to affect the charge of the peptide were also undertaken. GLP-1 bears a net neutral charge, possessing a total of 4+ charges related to basic amino acids at positions 7, 26, 34 and 36, and 4− charges related to acidic amino acids at positions 9, 15, 21 and 27. Exendin-4 bears a net negative charge related to a basic domain at position 21-23. Exendin-4 possesses a total of 4+ charges (positions 7, 18, 26, 33) and 6− charges (positions 9, 15, 21, 22, 23, 30), whereas its 9 amino acid terminal tail is neutral. The addition of a single basic amino acid (providing a positive charge) for the tail of exendin-4 (i.e., the replacement of small neutral glycine, G, by larger arginine, R, in position 36), as in peptide 34 (SEQ ID NO:31), results in inactivity of the peptide in in vitro insulin secretion. Arginine, R, is well tolerated in position 36 of GLP-1, and when retained or replaced in GLP-1 by neutral glycine, G, and the exendin-4 tail (peptide 12(SEQ ID NO:9) it remains active and actually has an activity that exceeds that of exendin-4. Interestingly, arginine, R, is well tolerated in position 36 of exendin-4 when position 30 is modified from acidic glutamic acid, E, to neutral alanine, A (peptide 36 (SEQ ID NO:33)) when position 27 bears a negative charge. Also, the replacement of a neutral serine, S, by a basic lysine, K, to introduce a positive charge into position 18 (peptide 1 (SEQ ID NO:3) as compared to peptide 30 (SEQ ID NO:27)), results in a loss of activity; however, the replacement of neighboring (position 19, 20) neutral amino acids, tyrosine, Y, and leucine, L, by neutral amino acids, glutamine, Q, and methionine, M, restores activity (peptide 9 (SEQ ID NO:6) as compared to peptide 30 (SEQ ID NO:27)).

Figure 3:
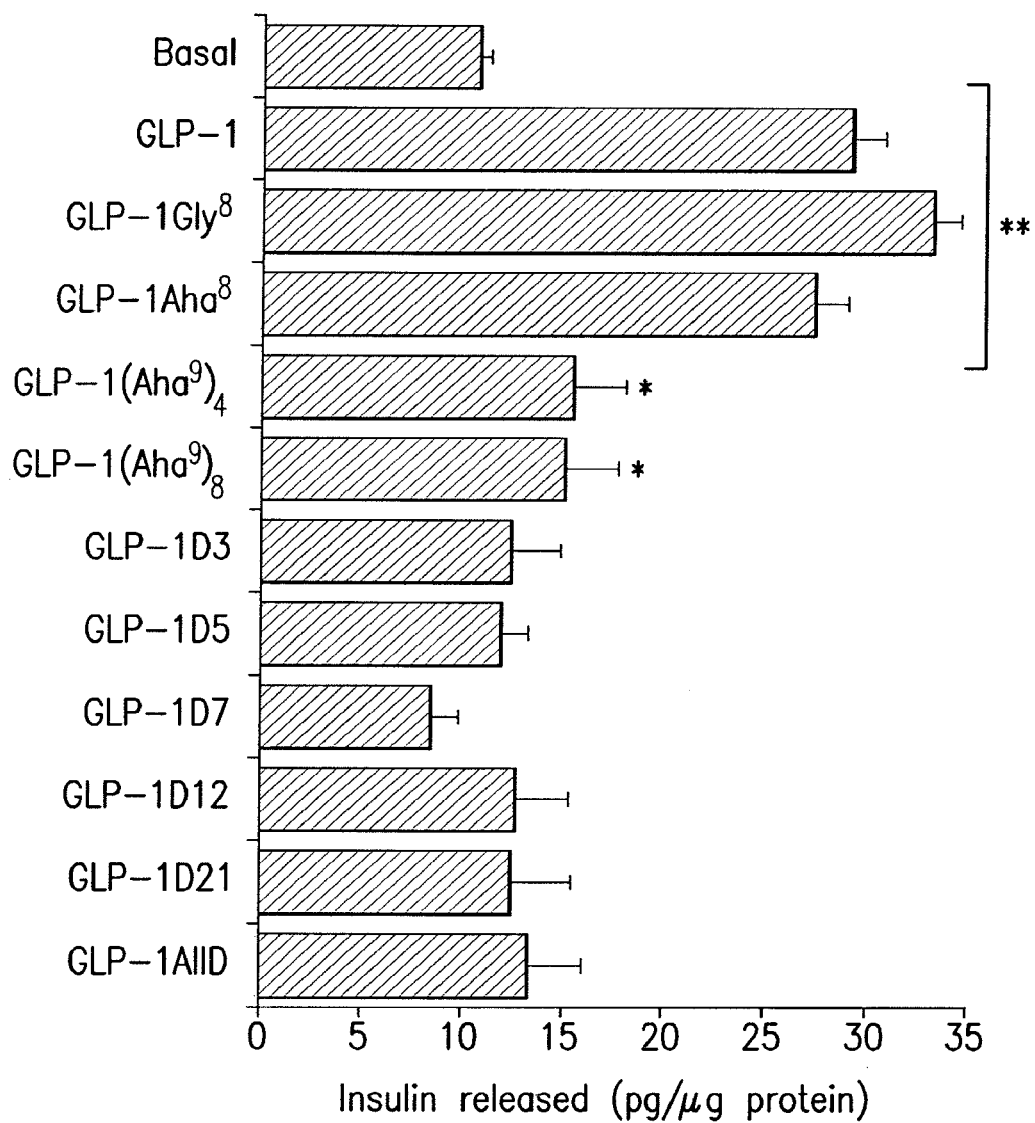
FIG. 3 shows a comparison in insulin secretion in RIN 1048-38 cells in the presence of glucose (5 mM) and in the presence or absence of 10 nM GLP-1 (SEQ ID NO:1, GLP-1 Gly$^8$ (peptide 1; SEQ ID NO:3), GLP-1 6-aminohexanoic acid$^8$ (peptide 11; SEQ ID NO:8), GLP-1 (6-aminohexanoic acid$^9$)$_4$ (peptide 25; SEQ ID NO:22), GLP-1 (6-aminohexanoic acid$^9$)$_8$ (peptide 26; SEQ ED NO: 23), or six analogues of GLP-1 that contain, from the carboxy terminus, 3, 5, 7, 12, 21, and all D-amino acids. The data represent the mean of 2-3 experiments ±SEM. **p<0.001, *p<0.05 for treated versus basal. Levels are expressed in pg of insulin/μg of protein. Basal release is also shown.

When the insulin secreting effects of GLP-1 and the 6-aminohexanoic acid-containing peptides were compared, GLP-1 Aha$^8$ (peptide 11; SEQ ID NO:8) was shown to be as effective as GLP-1. GLP-1 Aha$^8$ (peptide 11; SEQ ID NO:8) induced insulin secretion about 1.2-fold above basal levels. See FIG. 3. The insertion of additional 6-aminohexanoic acid residues, however, as in peptides 25 and 26 (SEQ ID NOs:22-23), abrogated the peptides' ability to induce insulin secretion.

Example 3

Intracellular cAMP Determination

CHO cells stably transfected with the human GLP-1 receptor, GLP-1R cells, were grown to 60-70% confluency on 12-well plates, washed three times with Krebs-Ringer phosphate buffer (KRP), and incubated with 1 ml of KRP containing 0.1% bovine serum albumin (BSA) for 2 h at 37° C. in a humidified air incubator. Cells were then incubated in 1 ml of KRP supplemented with 0.1% BSA with Isobutylmethylxanthine (IBMX) (1 mM; Calbiochem, La Jolla, Calif.) in the presence or absence of the peptides under study. The reaction was stopped 30 min later by washing the intact cells three times with ice-cold phosphate buffered saline (PBS). The intracellular cAMP was extracted by incubating the cells in ice-cold perchloric acid (0.6M, 1 ml, 5 min). After adjusting the pH of the samples to 7 using potassium carbonate (5M, 84 µl), sample tubes were vortexed and the precipitate formed was sedimented by centrifugation (5 min, 2000×g, 4° C.). The supernatant was vacuum-dried and solubilized in 0.05M Tris (pH 7.5) containing 4 mM EDTA, (300 µl). Sodium carbonate (0.15 µM) and zinc sulfate (0.15 µM) were added, to the samples which were then incubated for 15 min on ice. The resulting salt precipitate was removed by centrifugation (5 min, 2000×g, 4° C.). The samples were assayed in duplicate aliquots (50 µl) using a [$^3$H] cAMP competitive binding assay kit (Amersham, Philadelphia Pa.).

Figure 4:
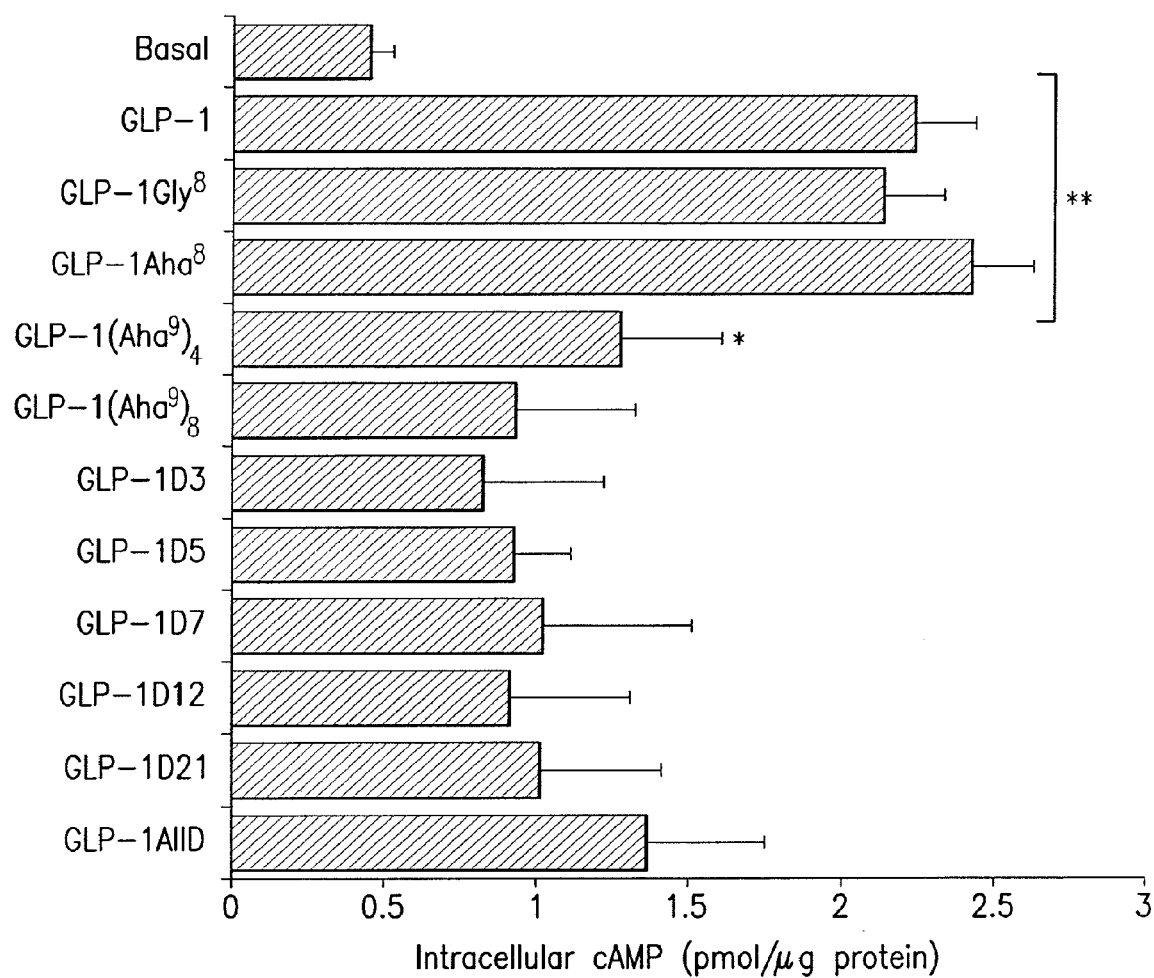
FIG. 4 shows the effect of GLP-1 analogs on the production of intracellular cAMP. CHO/GLP-1R cells were incubated with the indicated polypeptides (10 nM) for 30 min at 37° C., after which they were lysed and the lysates processed for determination of cAMP content. The data are normalized to maximum values obtained in the presence of GLP-1 (10 nM). The data points represent the mean of 2-3 experiments. **p<0.001, *p<0.05 for treated versus basal.
Figure 5:
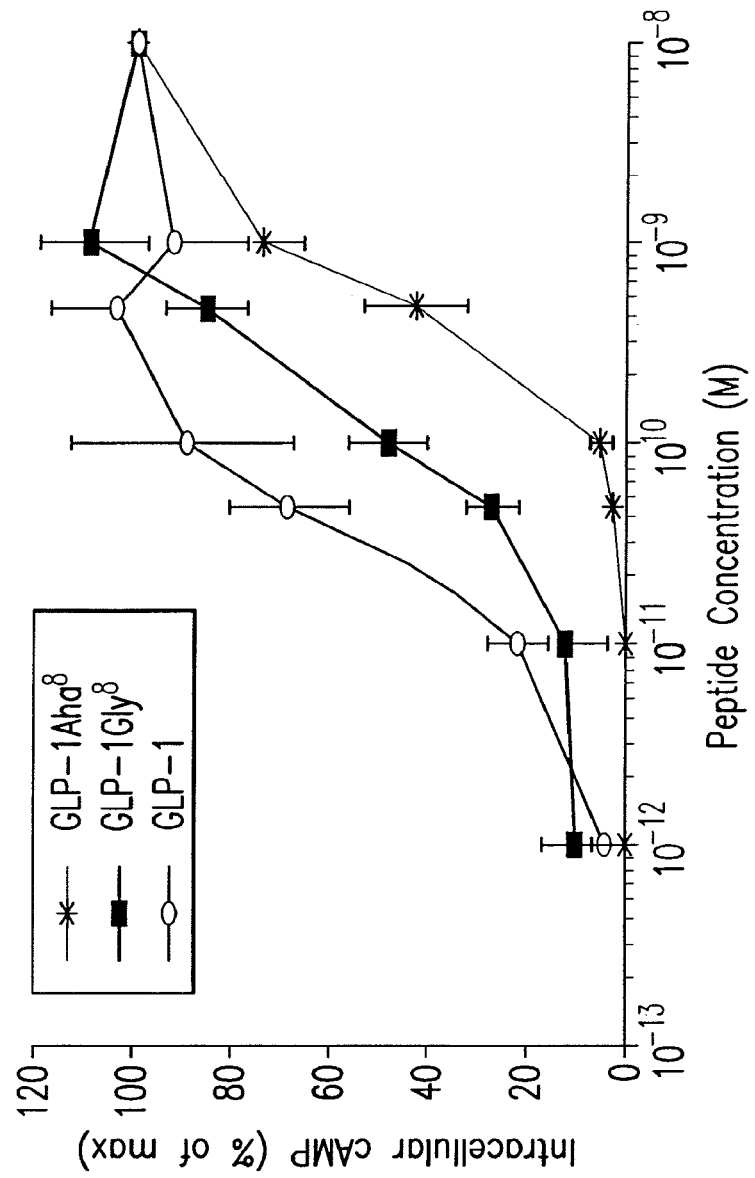
FIG. 5 shows dose response curves for GLP-1, GLP-1 Gly$^8$ (SEQ ID NO:3), and GLP-1 6-aminohexanoic acid$^8$ (SEQ ID NO:8). Intracellular cAMP levels were measured in CHO/GLP-1R cells after treatment with the indicated concentrations of GLP-1, GLP-1 Gly$^8$, and GLP-1 6-aminohexanoic acid$^8$ for 30 min at 37° C. The data were normalized to maximum values obtained in each experiment in the presence of GLP-1 (10 nM). Bars represent the means±SEM of three experiments preformed in triplicate.

Levels of cAMP were measured in cells treated with GLP-1, the 6-aminohexanoic acid-containing peptides, or the D-amino acid containing peptides. Intracellular cAMP levels generated by the GLP-1 analogs were assessed initially at a peptide concentration of 10 nM (the concentration at which maximum cAMP production is seen with GLP-1). The data are shown in FIG. 4. The peptides were incubated with the CHO/GLP-1 R cells in the presence of IBMX for 30 min at 37° C. In agreement with the results from the in vitro insulin assay, the D-amino acid substitutions throughout the GLP-1 molecule resulted in only a small increase above basal levels—i.e., those obtained with IBMX alone. Also, GLP-1 (Aha$^9$)$_4$ (SEQ NO:22) and GLP-1 (Aha$^9$)$_8$ (SEQ ID NO:23) were inactive when compared to the insulinotropic compounds, GLP-1 Gly$^8$ (SEQ ID NO:3) and GLP-1 Aha$^8$ (SEQ ID NO:8). The induction of cAMP in response to varying concentrations of GLP-1, GLP-1 Gly$^8$, or GLP-1 Aha$^5$ was measured. See FIG. 5. Table 3 shows the ED50 values of all three compounds. GLP-1 Aha$^8$ (0.5 nM) stimulated intracellular cAMP production to 4-fold above basal it however exhibited a higher ED50 when compared to GLP-1 and GLP-1 Gly$^8$.

TABLE 3

IC$_{50}$ and EC$_{50}$ Values Derived from the Binding and cAmp Experiments, Respectively

| Peptide Name | IC$_{50}$ (nM)$^a$ | EC$_{50}$ (nM) |
|---|---|---|
| GLP-1 | 3.7 ± 0.2 | 0.036 ± 0.002 |
| GLP-1 Gly$^8$ | 41 ± 9 | 0.13 ± 0.02 |
| GLP-1 Aha$^8$ | 22 ± 7 | 0.58 ± 0.03 |
| GLP-1 (Aha$^9$)$_4$ | 236 ± 25 | ND |
| GLP-1 (Aha$^9$)$_8$ | 400 ± 34 | ND |
| GLP-1 D3 | 301 ± 40 | ND |
| GLP-1 D5 | 350 ± 20 | ND |
| GLP-1 D8 | 265 ± 115 | ND |
| GLP-1 D12 | 574 ± 216 | ND |
| GLP-1 D21 | ND | ND |
| GLP-1 All D | ND | ND |

$^a$The concentration that reached 50% of $^{125}$I-GLP-1 binding was calculated in three to four separate experiments performed in triplicate.

Example 4

Competitive Binding of Peptides to GLP-1 Receptor in Intact Cells

Binding studies were performed in the manner of Montrose-Rafizadeh et al. (1997b), J. Biol. Chem. 272:21201-206. Briefly CHO/GLP-1R cells were grown to confluency on 12-well plates and washed with serum-free Ham F-12 medium for 2 h before the experiment. After two washes in 0.5 ml binding buffer (10), cells were incubated overnight at 4 C with 0.5 ml buffer containing 2% BSA, 17 mg/L Diprotin A (Bachem, Torence, Calif.), 10 mM glucose, 1-1000 nM GLP-1 or other peptides and 30,000 cpm SI-GLP-1 (Amersham, Philadelphia, Pa.). At the end of the incubation the supernatant was discarded, and the cells were washed three times with ice-cold PBS and incubated at room temperature with 0.5 ml of 0.5N NaOH and 0.1% sodium dodecyl sulfate for 10 min. Radioactivity in cell lysates was measured in an ICN Apec-Series g-counter. Specific binding was determined as total binding minus the radioactivity associated with cells incubated in the presence of a large excess of unlabeled GLP-1 (1 µM).

Figure 6:
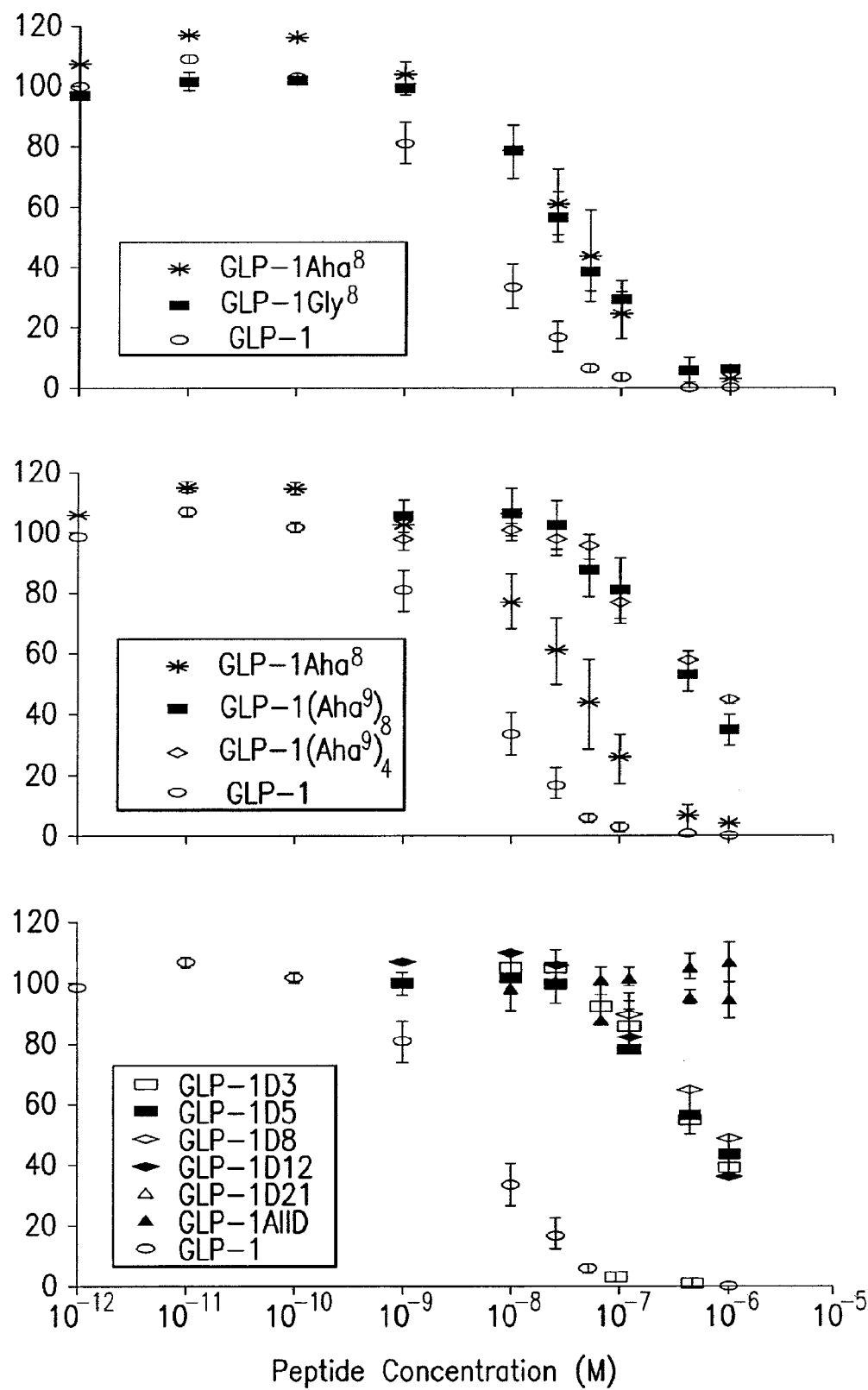
FIG. 6 shows the displacement of [$^{125}$I]-GLP-1 binding to CHO/GLP-1R cells with analogs of GLP-1. [$^{125}$I]-GLP-1 binding to intact CHO/GLPR cells was competed with various concentrations of the polypeptides shown. The data are normalized to maximum values obtained in the presence of 10 nM of the respective polypeptides. The data points represent the mean±SEM of three experiments preformed in triplicate.

The potential of these GLP-1 analogs to displace [$^{125}$I] GLP-1 by binding competitively to the human GLP-1 receptor was then examined. CHO/GLP-1R cells were incubated with [$^{125}$I] labeled GLP-1 in the absence and presence of varying concentrations of the peptides. See FIG. 6.

The IC$_{50}$ values obtained for those compounds which bound competitively to the GLP-1 receptor are shown in Table 3. Insertion of the 6-aminohexanoic acid moiety resulted in a reduction in binding to the receptor. With the increase in the length of the spacer 6-aminohexanoic acid groups in the 9-position, there was a dramatic decrease in affinity for the GLP-1 receptor. The lack of biological activity seen with the D-amino acid substituted compounds can be explained by their markedly reduced ability to bind to the GLP-1 receptor. There was a progressive reduction in receptor recognition with increasing D-amino acid substitution such that compounds GLP-1 D21 (peptide 6) and GLP-1 All D (peptide 7) did not displace the labeled GLP-1.

Example 5

Acute In Vivo Activity

The acute maximal insulin response was determined by quantifying plasma insulin levels in Zucker rats following intravenous peptide administration. Specifically, following overnight fasting, diabetic male rats, approximately 400 g weight, were anesthetized with 50 mg/kg pentobarbital and a catheter was tied into their right femoral artery for blood collection. Thereafter, a bolus of exendin-4, GLP-1 or peptide (0.4 nmol/kg) was administered into their left saphenous vein over 30 s (N=6 per peptide). Blood, taken prior to peptide administration and at 5, 15, 30, 60 and 90 min thereafter, was drawn into heparinized tubes containing EDTA and aprotinin for insulin determination. Plasma was separated, removed and immediately frozen to −70° C. The insulin levels then were quantified by using a rat insulin ELISA kit (Crystal Chem. Inc., Chicago, Ill.).

Figure 7:
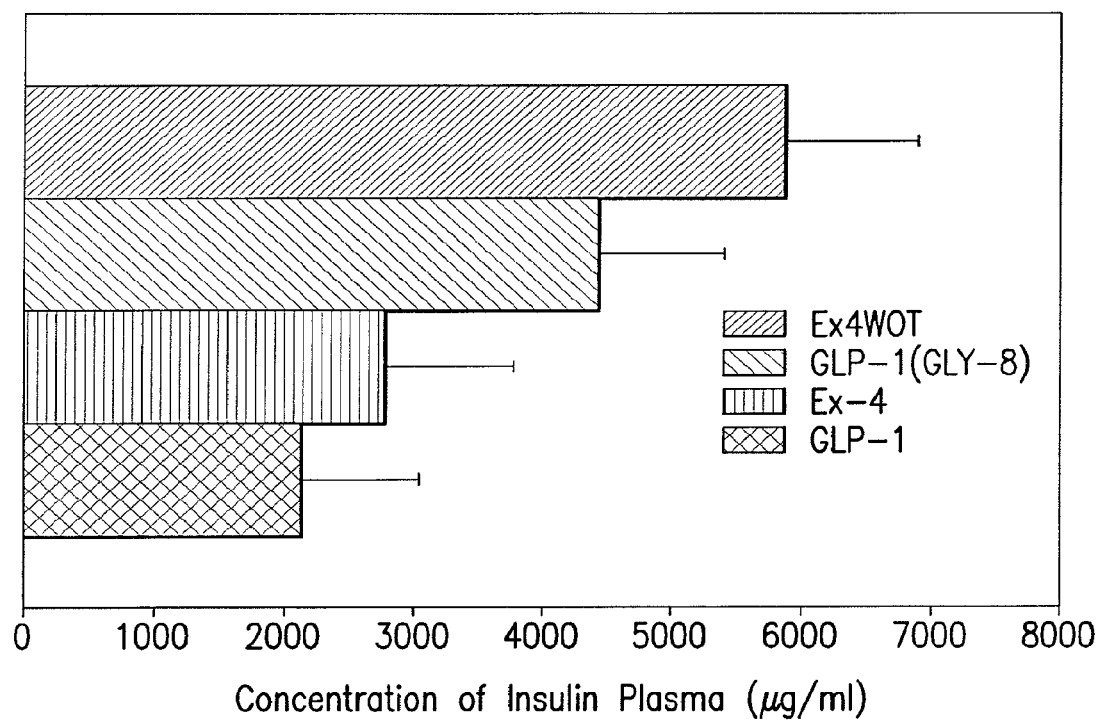
FIG. 7 shows the acute insulin-secreting activity of 0.4 nmol/kg of polypeptide Ex-4 WOT (SEQ ID NO:7) and GLP-1 Gly$^8$ (SEQ ID NO:3) in fasted, diabetic Zucker rats to induce insulin secretion as compared to equimolar concentrations of exendin-4 and GLP-1.

The acute in vivo activity of two examples of potent peptides from the in vitro studies above, peptide No. 10 (Ex-4 WOT; SEQ ID NO:7) and peptide1 (GLP-1 Gly$^8$; SEQ ID NO:3), was assessed in fasted, diabetic Zucker rats to induce insulin secretion. Peak plasma insulin concentrations are shown in FIG. 7 following equimolar administration of peptides (0.4 nmol/kg) and are compared to those achieved after equimolar exendin-4 and GLP-1. Both Ex-4 WOT and Gly-8 potently increased plasma insulin concentrations.

As illustrated in FIG. 7, the in vitro action of peptides to induce insulin secretion in RIN 1048-36 cells correlates with in vivo activity to acutely elevate plasma insulin concentrations in fasted diabetic Zucker rats, as exemplified by peptide 1 (GLP-1 Gly$^8$; SEQ ID NO:3) and peptide10 (Ex-4 WOT; SEQ ID NO:7) after their i.v. administration. Of particular note is the finding that Ex-4 WOT), which lacks the terminal 9 amino acids of exendin-4, proved to be more potent than did equimolar exendin-4. Similarly, peptide 1 (GLP-1 Gly$^8$) proved to be more potent than equimolar GLP-1.

Example 6

Duration of In Vivo Activity

The time-dependent duration of insulinotropic action was evaluated by quantifying plasma insulin and glucose levels in Zucker rats following intraperitoneal (i.p.) peptide administration. Specifically, after overnight fasting, diabetic male rats, approximately 400 g weight, were anesthetized with 50 mg/kg pentobarbital and a catheter was tied into their right femoral artery for blood collection. Thereafter, a bolus of exendin-4, GLP-1 or peptide (0.4 nmol/kg) was administered i.p. (N≥2 per peptide). Blood, taken prior to peptide administration, at 30 and 60 min, and at 2, 4, 6 and 24 h, was drawn into heparinized tubes containing EDTA and aprotinin for insulin determination, and a separate sample was taken to measure glucose. Plasma was separated, removed and immediately frozen to −70° C. Thereafter insulin levels were quantified by using a rat insulin ELISA kit (Crystal Chem. Inc., Chicago, Ill.) and plasma glucose was quantified by the glucose oxidase method.

Figure 8:
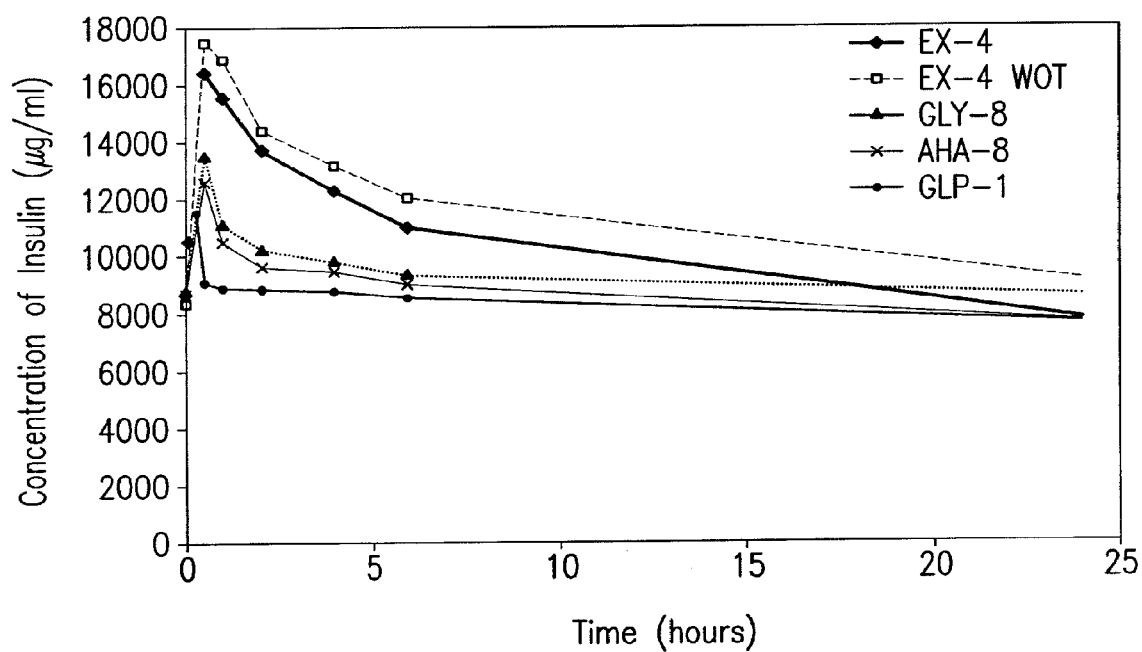
FIG. 8 shows the time course of insulin-secreting activity of 0.4 nmol/kg of polypeptide 10 (Ex-4 WOT (SEQ ID NO:7)), polypeptidel (GLP-1 Gly$^8$ (SEQ ID NO:3)), and polypeptidel 1 (GLP-1 6-aminohexanoic acid$^8$ (SEQ ID NO:8)) in fasted, diabetic Zucker rats up to 24 hours as compared to equimolar concentrations of exendin-4 and GLP-1.

As shown in FIG. 8, specific amino acids modifications provide a long duration of action on in vivo insulin. In this regard, the action of polypeptide 10 (Ex-4 WOT; SEQ ID NO:7) on plasma insulin levels proved to be long acting, like exendin-4. In addition, similar to acute studies, polypeptide 10 proved to be more potent than equimolar exendin-4 in diabetic rats. In contrast, polypeptide 1 (GLP-1 Gly$^8$; SEQ ID NO:3) and polypeptide 11 (GLP-1 Aha$^8$; SEQ ID NO:8) proved to have an action on the time-dependent insulin response that was intermediate between GLP-1 and exendin-4; being longer than the former but shorter than the latter. In addition, similar to acute studies, polypeptides 1 and 11 proved to be more potent than equimolar GLP-1 in diabetic rats.

Example 7

MALDI Mass Spectroscopy

GLP-1 (2 µM) and GLP-1 Aha$^8$ (SEQ ID NO:8) (2 µM) were incubated with 5 mU recombinant DPP1V (Calbiochem, La Jolla, Calif.) in PBS for 10 min and 2 h respectively at 37° C. Both compounds (100 µM, 100 µl) were incubated in an equivalent volume of human serum at 37° C. for 2 h. In all cases, enzymatic reactions were quenched by the addition of trifluoroacetic acid (0.1% v/v final concentration). Samples were immediately analyzed using Matrix Assisted Linear Desorption Ionisation—Time Of Flight (MALDI-TOF) mass spectrometry. A Micromass MALDI-TOF (Micromass, Beverly, Mass.) reflectron instrument was used at a laser energy of 15-25% over a mass range of 1000-6000 Da, with 5 laser shots summed per spectrum. Alpha-cyano-4-hydroxycinnamicacid (Sigma, St. Louis, Mo.) was used as a matrix and was prepared to a concentration of 10 mg/ml in a 8 mg/ml ammonium carbonate (Sigma, St. Louis, Mo.) buffer. One microliter samples were diluted 50/50 v/v with matrix before being transferred to the MALDI plate.

The stability of GLP-1 Aha$^8$ (SEQ ID NO:8) was compared with GLP-1 in the presence of DPP1V and human serum. Treatment of GLP-1 (2 µM) with DPP1V (5 mU) for 10 min or 100% serum for 2 h at 37° C. caused a considerable increase in the amount of N-terminal truncated product (Mr=3089 gmol-1) as measured by MALDI. In contrast GLP-1 Aha$^8$ (2 µM) appeared resistant to either treatment.

Example 8

Determination of Biological Activity of GLP-1Aha$^8$ In Vivo

Six-month old male Zucker fa/fa rats (Harlan, Indianapolis, Ind.) and six-month old Wistar rats were used in this study. They were allowed ad libitum access to chow and water and were on a 12 h light, 12 h dark cycle (lights on 0700 h). The bedding for the Zucker rats was a paper based product, "Carefresh" (Absorption Co., Belingham, Wash.). The Zucker rats were fasted on wire, in the absence of bedding, overnight before the experiment. Wistar rats were fasted on their normal bedding. General anaesthesia was induced by an intraperitoneal injection of pentobarbital (50 mg/kg). A cannula was placed in the femoral artery for blood sampling and the polypeptides (GLP-1 Aha$^8$ (SEQ ID NO:8) and GLP-1 Gly$^8$ (SEQ ID NO:3), 24 nmol/kg) were injected subcutaneously into the nape of the animals' necks (n=5 for each treatment group). Blood glucose levels were measured by the glucose oxidase method using a Glucometer Elite (Bayer Corp. Diagnostics, Tarrytown, N.Y.).

Figure 9:
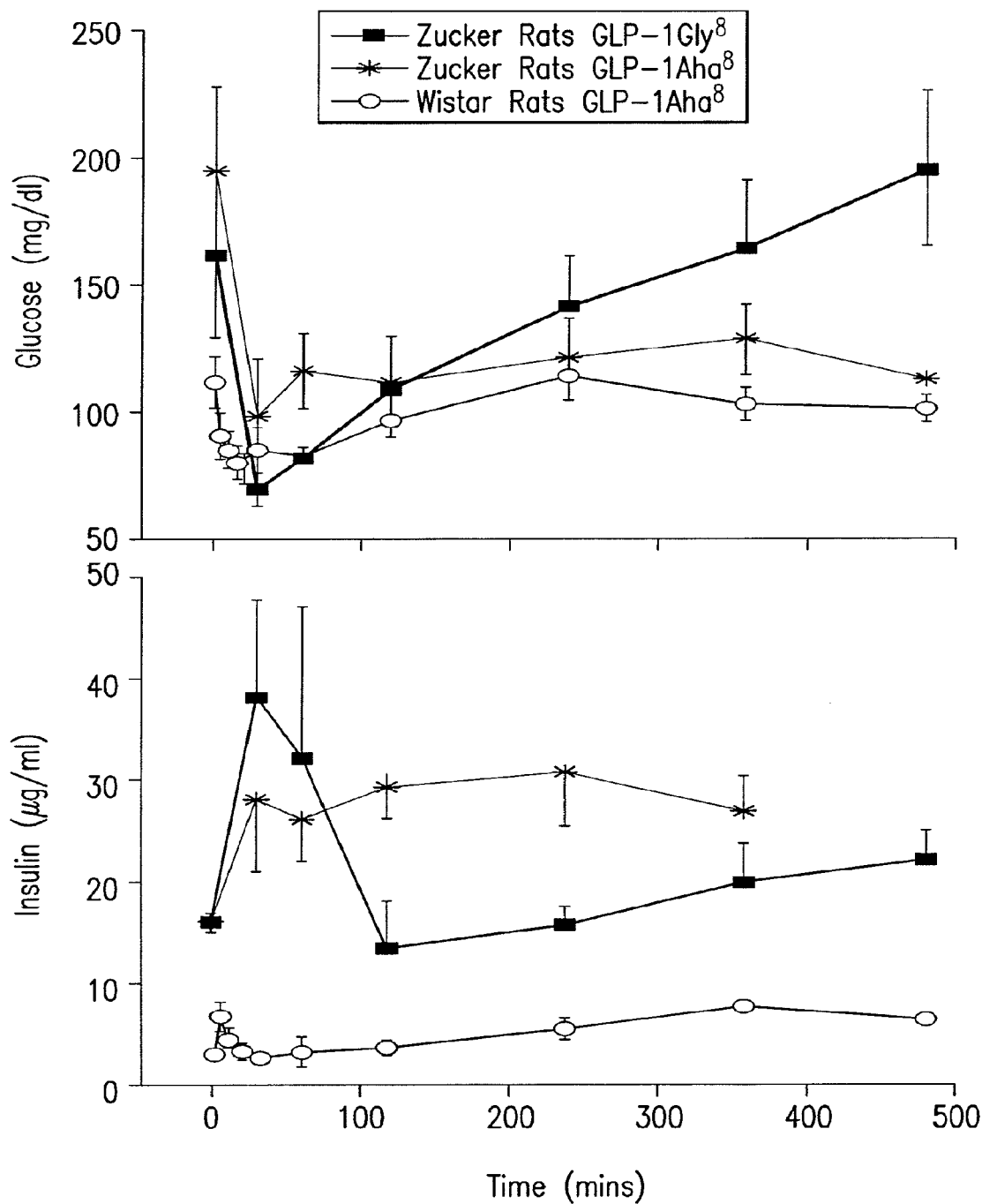
FIG. 9 shows the biological effects of GLP-1 Gly$^8$ (SEQ ID NO:3) and GLP-1 6-aminohexanoic acid$^8$ (SEQ ID NO:8).
Figure 10A:
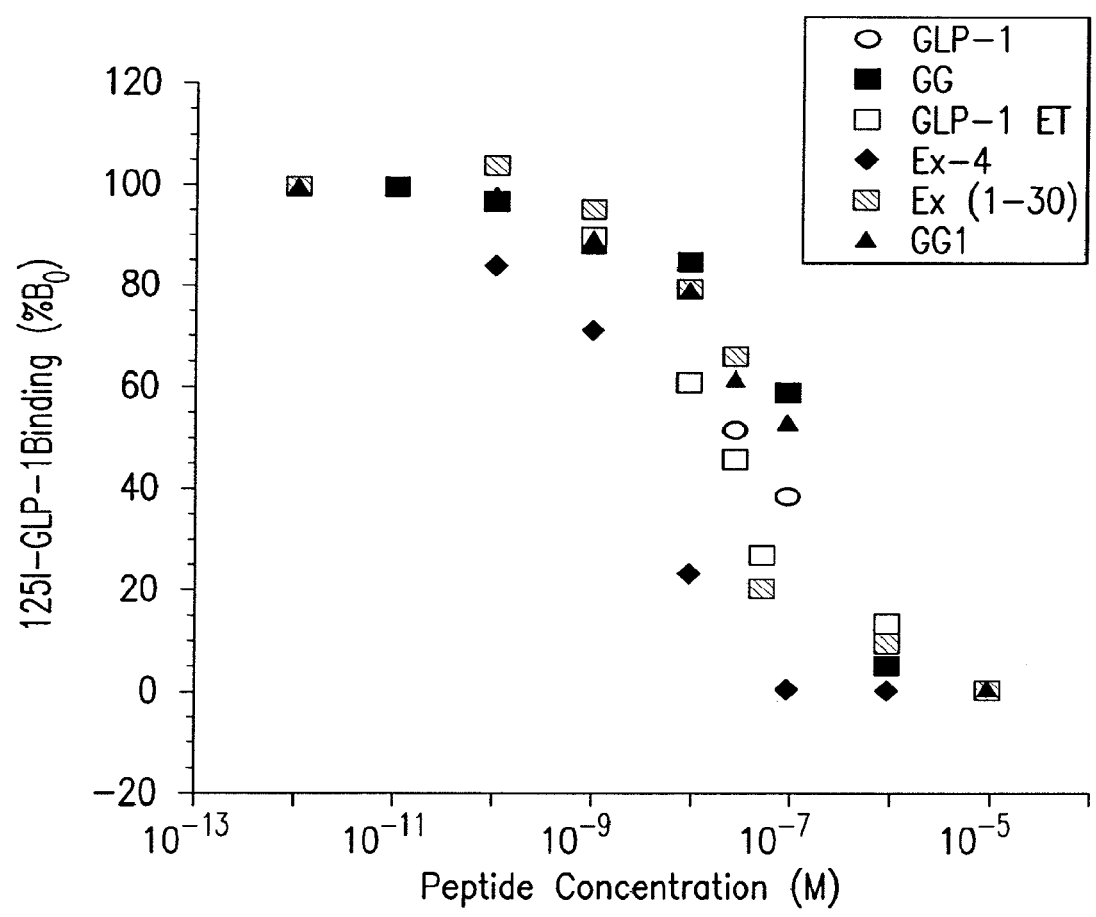
FIG. 10 shows the displacement of [$^{125}$I] GLP-1binding to CHO/GLP-1R cells with the analogs of GLP-1, GLP-1 Gly8 and Ex-4. [$^{125}$I] GLP-1 binding to intact CHO/GLP-1R cells was competed with various concentrations of the peptides shown. Each of FIGS. 10A, B, and C show the data for different peptides. The data are normalized to maximum values obtained in the presence of 10 nM of the respective peptides. The data points respresent the mean of three experiments performed in triplicate. B$_o$, maximum binding in the absence of cold peptide.
Figure 10B:
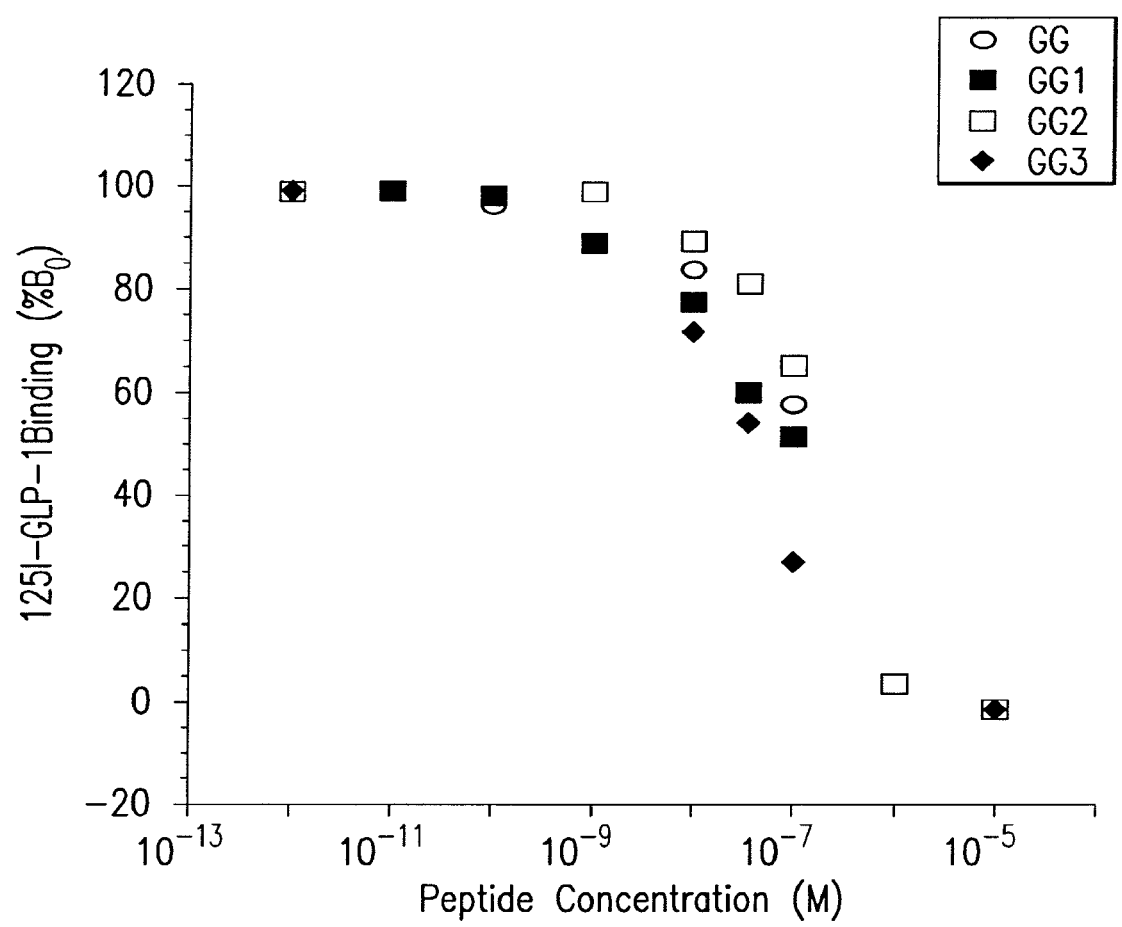
Figure 10C:
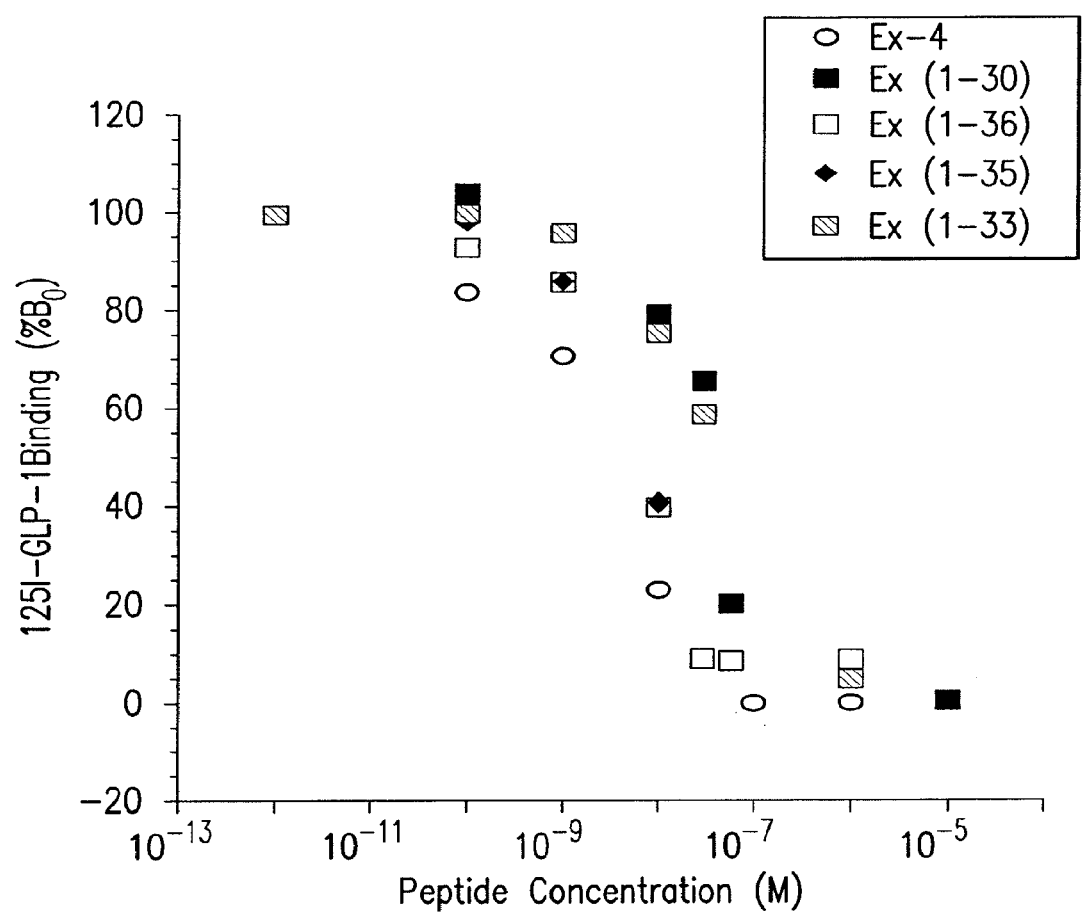

To verify that GLP-1 Aha$^8$ had biological activity in vivo, the polypeptide was administered subcutaneously (24 nmol/kg) to fasted Zucker fatty (fa/fa) and Wistar rats. Another group of Zucker rats received a similar dose of GLP-1 Gly$^8$. Blood glucose was then monitored for the next 8 h. In FIG. 9, the results show that both compounds rapidly lowered blood glucose. In Zucker rats, the reduction in blood glucose was more pronounced with GLP-1 Gly$^8$, due to the fact that the fasting glucose was lower in that group, but the slope and magnitude of the decline was similar for both compounds. Insulin secretion was attenuated in the GLP-1 Gly$^8$ due to the drop in blood glucose into the hypoglycemic range, proving the glucose-dependency of insulinotropism with this class of compounds. As the GLP-1 Aha$^8$-treated Zucker rats did not become hypoglycemic the insulinotropic response did not become abrogated and the prolonged effect can be seen. In Wistar rats, which are not hyperglycemic in the fasting state, insulin levels increased rapidly with GLP-1 Aha$^8$, leading to hypoglycemia and again rapid attenuation of the insulinotropic response.

Example 9

Truncation of Exendin-4 and the Biological Importance of the 9-Amino Acid C-Terminal Tail of Exendin-4

This study was performed to determine the importance of the nine C-terminal amino acids to the biological activity of Ex-4. A sequence of truncated Ex-4 analogs and GLP-1 analogs to which the nine C-terminal sequence has been added were used in the study.

Materials and Cell Lines

Peptides were synthesized as described above. All peptides were of 95% or greater purity. Table 4 shows the sequences of the GLP-1 and exendin-4 analogs studied. Isobutylmethylxanthine (IBMX) was purchased from Calbiochem (La Jolla, Calif.). Exendin-4 and GLP-1-(7-36) amide were obtained from Bachem (Torrance, Calif.). The cloned rat insulinoma cell line RIN 1046-38 was a gift from Dr. Samuel A. Clark (Bio Hybrid Technologies, Shrewsbury, Mass.) and were routinely cultured in M199 with Earle's salts (Mediatech, Inc., Herndon, Va.) supplemented with glucose (11 mM), 50 U/ml penicillin, 50 µg/ml streptomycin, and glutamine (2 mM) in a humidified 5% $CO_2$-95% air incubator at 37 C. Chinese hamster ovary (CHO) cells stably transfected with the human GLP-1 receptor, CHO/GLP-1R cells, were described above. Plasma insulin levels were measured by ELISA (Crystal Chem. Inc., Chicago Ill.). HbA1c was measured as described in Greig et al., 1999. Blood glucose levels were measured using a Glucometer Elite (Bayer Diagnostics, Tarrytown, N.Y.).

Animals

Six-month-old male Zucker fa/fa rats (Harlan, Indianapolis, Ind.), 2-month old C57BLKS/J-Leprdb/Leprdb mice (Jackson Laboratories, Bar Harbor, Mass.) and 2-month old Fisher rats (Harlan, Indianapolis, Ind.) were used in the acute and chronic experiments. All animals were allowed ad libidum access to chow and water. Animals were on a 12 hour light-dark cycle (lights on 7 am). The bedding for the Zucker rats and db/db mice was a paper-based product, Carefresh (Absorption Co., Belingham, Wash.) and the Fisher rats were housed on normal bedding.

Intracellular cAMP Determination

RIN 1046-38 cells, grown to 60-70% confluence on 12-well plates were treated as described in Example 3 and cAMP determinations were performed accordingly. Dose response curves are shown in FIG. 21.

Competitive Binding of Peptides to GLP-1 Receptor in Intact Cells

Binding studies were performed as described in Example 4. Table 5 shows $IC_{50}$ and $EC_{50}$ values derived from the competitive binding in CHO GLP-1R cells and cAMP assays in RIN 1046-38 cells respectively.

TABLE 4

The amino acid sequences of the GLP-1 and exendin-4 analogs studied

| | | | |
|---|---|---|---|
| GLP-1(7-36) | | | 7    11    16    21    20    25<br>36<br>HAEGTFTSDVSSYLEGQAAKEFIAWLVKGR<br>(SEQ ID NO: 1) |
| GLP-1(7-36) Exendin(31-39) | | GLP-1 ET | HAEGTFTSDVSSYLEGQAAKEFIAWLVKGR<u>PSSGAPPPS</u><br>(SEQ ID NO: 9) |
| Exendin-4 | | Ex-4 | 1    5    10    15    20    25<br>30    35<br>H<u>G</u>EGTFTSDLSKQMEEEAVRLFIEWLK<u>N</u>GG<u>PSSGAPPPS</u><br>(SEQ ID NO: 2) |
| Exendin (1-36) | | Ex(1-36) | H<u>G</u>EGTFTSDLSKQMEEEAVRLFIEWLK<u>N</u>GG<u>PSSGAP</u><br>(SEQ ID NO: 49) |
| Exendin (1-35) | | Ex(1-35) | H<u>G</u>EGTFTSDLSKQMEEEAVRLFIEWLK<u>N</u>GG<u>PSSGA</u><br>(SEQ ID NO: 13) |
| Exendin (1-33) | | Ex(1-33) | H<u>G</u>EGTFTSDLSKQMEEEAVRLFIEWLK<u>N</u>GG<u>PSS</u><br>(SEQ ID NO: 14) |
| Exendin (1-30) (Ex-4 WOT) | | Ex(1-30) | H<u>G</u>EGTFTSDLSKQMEEEAVRLFIEWLK<u>N</u>GG<br>(SEQ ID NO: 11) |
| GLP-1Gly$^8$(7-36) | | GG | 7    11    16    21    20    25<br>36<br>H<u>G</u>EGTFTSDVSSYLEGQAAKEFIAWLVKGR<br>(SEQ ID NO: 3) |
| GLP-1Gly$^8$(7-36) Exendin(31-39) | | GG1 | H<u>G</u>EGTFTSDVSSYLEGQAAKEFIAWLVKGR<u>PSSGAPPPS</u><br>(SEQ ID NO: 50) |
| GLP-1Gly$^8$(7-36) Exendin(31-36) | | GG2 | H<u>G</u>EGTFTSDVSSYLEGQAAKEFIAWLVKGR<u>PSSGAP</u><br>(SEQ ID NO: 51) |
| GLP-1Gly$^8$(7-36) Exendin(31-33) | | GG3 | H<u>G</u>EGTFTSDVSSYLEGQAAKEFIAWLVKGR<u>PSS</u><br>(SEQ ID NO: 52) |

The underlined amino acids refer to those from the exendin-4 sequence that are being studied.

TABLE 5

The $IC_{50}$ and $EC_{50}$ values derived from the competitive binding in CHO GLP-1R cells and cAMP assays in RIN 1046-38 cells respectively.

| Peptide Name | $IC_{50}$(nM) | $EC_{50}$(nM) |
| --- | --- | --- |
| GLP-1 | 44.9 ± 3.2 | |
| GG | 220 ± 23 | |
| $GG_1$ | 74 ± 11 | |
| $GG_2$ | 129 ± 39 | |
| $GG_3$ | 34.5 ± 14.5 | |
| GLP-1 ET | 21.2 ± 2.9 | |
| Ex-4 | 3.22 ± 0.9 | |
| Ex (1-36) | 8.8 ± 1.4 | ND |
| Ex (1-35) | 7.0 ± 2 | ND |
| Ex (1-33) | 49.0 ± 1.1 | ND |
| Ex (1-30) | 32.0 ± 5.8 | |
| Ex (1-28) | 45.0 ± 5.7 | |
| Ex(1-26) | No binding | No activity |
| Ex (1-23) | No binding | No activity |
| Ex (1-20) | No binding | No activity |
| Ex (1-17) | No binding | No activity |
| Ex (1-14) | No binding | No activity |
| Ex (1-11) | No binding | No activity |
| Ex (1-8) | No binding | No activity |

The concentration that reached 50% of $[I^{125}]$ GLP-1 binding was calculated in three or four separate experiments performed in triplicate. Peptides of a few as 11 amino acids were assessed and such amino acids had minimal binding.

Statistical Analysis

All values are shown as the mean±SEM, and the differences among the groups were analyzed using ANOVA. The curves for FIGS. 1 and 2 were fitted with a four-parameter sigmoid logistic regression equation using an iterative computer program (20), and the EC50 and IC50 values in Table 2 were calculated from the fitted data.

Acute Time-Course Experiments in Zucker fa/fa Rats

Six-month-old male Zucker fa/fa rats (Harlan, Indianapolis, Ind.) were used in this study as described above in Example 5, except 10 nmol/kg of peptide was administered in a PBS solution containing 0.1% BSA. Blood glucose levels following sc injections of Ex (1-36) and Ex (1-35) are shown in FIG. 22.

Chronic Study with Ex (1-30) in db/db Mice

Animals were housed in our facilities for 2.5 months to facilitate their acclimatization before the experiment commenced. For the first 20 days of treatment the animals were given Ex (1-30) (1 nmol/kg) by intraperitoneal (ip) injection daily at 9 am. Thereafter, animals received ip Ex (1-30) (1 nmol/kg) at approximately 9 am and 9 pm for the following 32 days. At the end of the first 20 days of the treatment protocol blood glucose levels and HbA1c were measured. Food intake and animal weight was determined daily at the time of the 9 am injection. No day was missed in the schedule. Magnetic resonance images (MRI) were taken on 51 and an IPGTT was performed on day 52.

At day 20 the HbA1c were 7.8±0.4 for the Ex(1-30) treated mice and 7.7±0.3 for the saline treated mice. The fasting blood glucose values were 412±92 mg/dl for the Ex(1-30) treated mice and 600±1 mg/dl for the saline treated mice.

Magnetic Resonance Imaging

Magnetic resonance images were obtained using a 1.9 T, 31 cm bore Bruker BioSpec system (Bruker Medizintechnik GmbH, Ettlingen, Germany), a 20 cm inner diameter shielded gradient set and a 5 cm diameter volume resonator. The animals used in the chronic study were placed under isofluorane anesthesia and standard T1 weighted multislice spin-echo images (TR=500 ms, TE=8.5 ms) were obtained over 20 contiguous transverse slices of thickness 2.1 mm each, covering a region which included the entire abdomen. The field of view was 5×5 cm over 128×128 pixels. Each image was acquired using 8 acquisitions, over a total imaging time of approximately 9 minutes. Imaging was performed on all animals at two time points (day 0 and day 51).

Separation of visceral and subcutaneous regions was performed (Bruker Paravision software) by drawing regions of interest (ROIs) for each slice. Segmentation of adipose from normal tissue was achieved using intensity histograms derived from each ROI (NIH Image software, National Institutes of Health, USA). The histograms generally showed two well-separated peaks (corresponding to water and adipose tissue), which were isolated using the valley between them as the demarcation point, enabling the adipose tissue content in each ROI to be summed.

The results are shown in FIG. 23. Although both sets of animals (control and Ex(1-30)-treated) lost weight, the Ex(1-30) treated animals showed a reduction in visceral fat deposition. The treated animals did not lose weight as fast as the controls, which did not receive the drug. Thus the treatment alleviated the diabetes and the treated animals were healthier.

Example 10

The Effect of GLP-1 and GLP-1 Analogues on the Metabolism of β-Amyloid Precursor Protein (βAPP)

One of the important pathological hallmarks of Alzheimer's disease (AD) is the cerebrovascular deposition of senile plaques comprised largely of amyloid-β peptide (Aβ). Aβ is derived from the larger glycosylated membrane-bound protein β-amyloid precursor protein (βAPP). The majority of βAPP is proteolytically cleaved within the Aβ domain to generate a soluble derivative (sAPP), which prevents the formation of amyloidogenic fragments. This study was performed to determine the effect GLP-1 and two analogues on the processing of the β-amyloid precursor protein.

PC12 cells were cultured in RPMI 1640 supplemented with 10% heat-inactivated horse serum, 5% heat-inactivated fetal calf serum, 25 mM Hepes buffer and 1× antibiotic-antimycotic solution (all culture media and sera were obtained from MediaTech Inc. (Herndon Va.). Treatments were carried out in low serum in the presence of GLP-1 (3.3, 33, and 330 μg/ml) (Bachem, Torrance, Calif.), and two analogues, exendin-4 (0.1, 1.0 and 10 μg/ml) and exendin-4-WOT (peptide 10 (Ex-4 WOT; SEQ ID NO:7)) (0.1 and 1.0 μg/ml). NGF (5, 10, 25 and 50 ng/ml) (Promega, Madison, Wis.), which has been shown to stimulate the secretory pathway resulting in more sAPP being secreted by PC12 cells into the conditioned medium, was used as a positive control. Following treatment for three days, conditioned media and cell lysates from untreated (low serum medium alone) and treated cells were subjected to immunoblot analysis using the monoclonal antibody, 22C11 (Roche Molecular Biochemicals, Indianapolis, Ind.). The antibody, raised against E. Coli-made βAPP whose epitope region has been assigned to $βAPP_{66-81}$ in the ectoplasmic cysteine-containing domain, recognizes all mature forms of βAPP found in cell membranes, as well as carboxy-truncated soluble forms secreted into conditioned media. In typical immunoblots of conditioned media or cell lysates from treated or untreated cells, multiple high molecular weight protein bands ($M_r$ 100-140 kDa) were evident. The differences observed in the profile of immunoreactive bands in the immunoblots was due neither to the unequal loading of proteins into the gel nor to the uneven transfer of proteins onto the membrane. Equivalent amounts of total protein were loaded in each lane of the gel and the efficiency of the electrophoretic transfer was monitored by staining the membranes with 0.1% Ponceau S in 5% acetic acid.

Figure 11A:
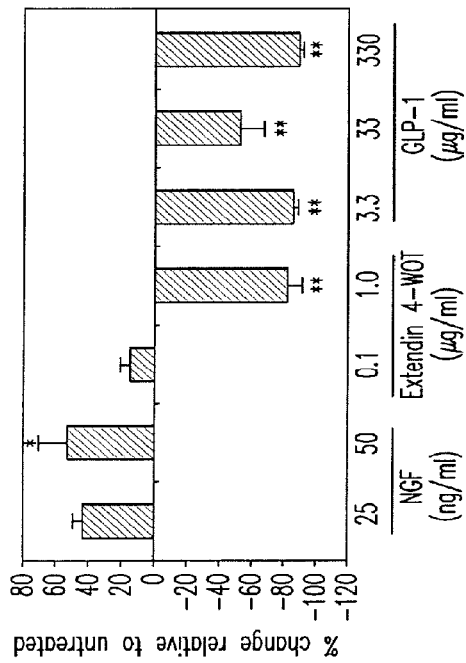
FIG. 11 shows the densitometric quantification of proteins extracted from NGF, exendin-4, exendin-4 WOT and GLP-1 treated PC12 cells. Protein bands obtained from cell lysates and conditioned media samples were analyzed by Western blotting and immunoprobed with the 22C11 monoclonal antibody (epitope: βAPP aa 66-81, Roche Molecular Biochemicals, Indianapolis, Ind.). Data are presented as the percent change in expression of βAPP derivatives from cell lysates samples (A and B) and soluble sAPP from conditioned media samples taken on day 3 of treatment (C and D) relative to untreated control samples cultured in low serum media alone.
Figure 11B:
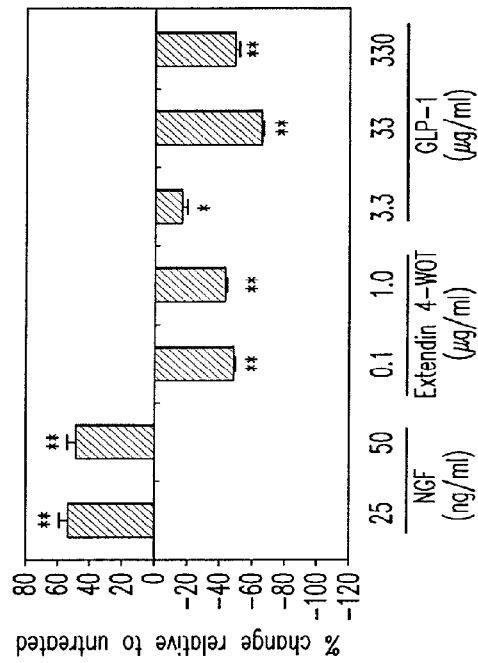

Densitometric quantification of the upper band revealed dramatic increases in intracellular levels of βAPP following NGF treatment (FIG. 11A, bars 1 and 2; FIG. 11B, bars 1 and 2). Inherent variation between cell culture experiments accounts for the difference in the degree of differentiation following treatment with 5 ng/ml and 10 ng/ml NGF in one series of studies (FIGS. 11A and C), and with 25 ng/ml and 50 ng/ml NGF in a different series of studies (FIGS. 11B and D). In contrast to NGF, GLP-1 and analogues decreased intracellular levels of βAPP (FIG. 11A, bars 3-5; FIG. 11B, bars 3-7). The combination of NGF and exendin-4 increased intracellular βAPP relative to untreated cells, but at a level in between that of the two treatment conditions alone (FIG. 11A, bar 6).

Figure 11C:
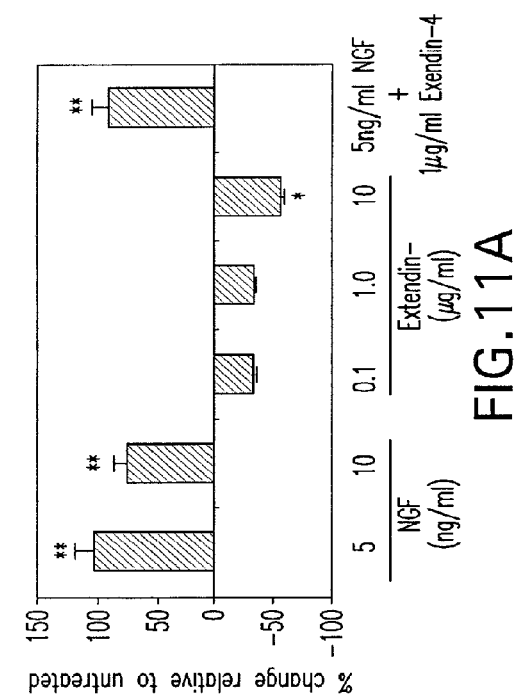
Figure 11D:
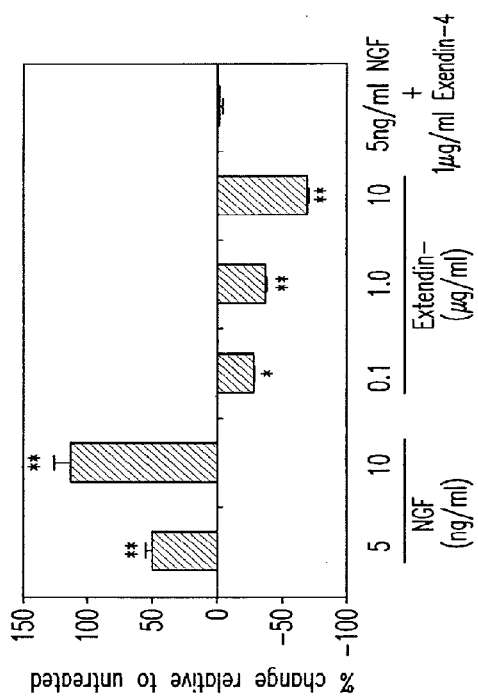

As shown in FIGS. 11C and D, all doses of nerve growth factor treatment resulted in dramatic increases in secreted, soluble derivatives of βAPP which could be detected in the conditioned medium (FIG. 11C, bars 1 and 2; FIG. 11D, bars 1 and 2). Following a similar pattern to intracellular βAPP levels from cell lysates, treatment with all doses of GLP-1, exendin-4 and exendin-4-WOT, produced decreases in detectable levels of sAPP in conditioned media (FIG. 11, bars 3-5; FIG. 11D, bars 3-7). The combination of NGF and exendin-4 did not produce any change in sAPP levels relative to untreated cells (FIG. 11C, bar 6).

Using the lactate dehydrogenase (LDH) kit from Sigma Co., the assay of LDH was performed as described below in the conditioned medium and cell lysate samples of both treated and untreated cells that were used. No significant change was observed in the level of LDH between treated and untreated cells under the conditions used. The possibility of toxicity as a result of treatment with GLP-1 and analogues, at the doses used, can be ruled out.

The data indicate reduced levels of secreted derivatives and mature forms of βAPP following GLP-1 treatment in PC12 cells. These reductions in sAPP secretion may be a consequence of reduced βAPP synthesis.

Example 11

GLP-1 and Analogues Promote Neuronal Proliferation and Differentiation

The effects of GLP-1 and two of its long-acting analogues, exendin-4 and exendin-4 WOT, on neuronal proliferation and differentiation and on the metabolism of neuronal proteins in the rat pheochromocytoma (PC12) cell line were tested. GLP-1 and exendin-4 induced neurite outgrowth, which was reversed by co-incubation with the selective GLP-1 receptor antagonist, exendin (9-39). Furthermore, exendin-4 enhanced nerve growth factor (NGF) initiated differentiation and rescued degenerating cells following NGF-mediated withdrawal.

Materials

7S NGF was purchased from Promega (Madison, Wis.). GLP-1 and exendin (9-39) were obtained from Bachem (Torrance, Calif.). Exendin-4 and its analogue exendin-4 WOT were synthesized and assessed to be >95% pure by HPLC analysis as described above. All other chemicals were of high purity and obtained from Sigma Chemicals (St. Louis, Mo.), unless otherwise stated.

Data Analysis

Statistical analyses were performed where appropriate. Results are expressed as mean±SEM (where SEM=standard error of the difference between the means). Analysis of variance (ANOVA) was carried out using SPSS version VII, where $p<0.05$ was considered statistically significant. Following significant main effects, planned comparisons were made using Tukey's Honestly Significant Difference test (Tukey's HSD).

Culture Conditions

Pheochromocytoma cells were obtained from Dr. D. K. Lahiri (Indianapolis) and RIN 1046-38 cells (a clonal rat insulinoma cell line) were a gift from Dr. Samuel A. Clark (Bio Hybrid Technology, Shrewsbury, Mass.). PC12 cells were cultured in RPMI 1640 supplemented with 10% heat-inactivated horse serum, 5% heat-inactivated fetal calf serum, 25 mM Hepes buffer and 1× antibiotic-antimycotic solution. RIN 1046-38 cells were grown in medium 199 containing 12 mM glucose and supplemented with 5% heat-inactivated fetal calf serum, 0.03% glutamine, 50 U/ml penicillin and 50 mg/ml streptomycin. Cell culture media and sera were obtained from MediaTech (Cellgro), Inc. (Herndon, Va.). The cells were grown in a humidified atmosphere containing 5.0% $CO_2$. They were seeded at approximately $2.0×10^6$ cells per 60 mm dish. PC12 cells were grown on cultureware coated in rat-tail collagen (Roche Molecular Biochemicals, Indianapolis). The 7S NGF was prepared by dilution in growth media at a concentration of 100 mg/ml and stored at −20° C. Stock solutions of GLP-1 and analogues were made fresh in sterile water and stored at −20° C.

Three dishes for each treatment condition were prepared. Treatments began 24 hours after seeding, once cells were well attached. The medium was aspirated, and 3 ml of fresh low serum media (containing only 0.5% fetal calf serum) with the appropriate compound(s), added.

Preparation of Cell Lysates

Conditioned media and cell pellets were harvested daily for protein analysis by immunoblotting. Cell lysates were prepared as follows. The cells from the plate were collected gently and centrifuged at 800 g for 10 minutes. The cell pellet was suspended in lysis buffer containing 10 mM Tris-HCl (pH 7.4), 1% SDS, 0.174 mg/ml phenylmethylsulfonyl fluoride (PMSF), 1 mg/ml each of aprotinin, leupeptin, pepstatin A, and 4 ml of a mixture of 45.98 mg/ml sodium vanadate and 10.5 mg/ml sodium fluoride. The suspended cells were triturated and centrifuged at 14,000 g for 15 minutes. The proteins of the supernatant solution (cell lysate) were measured (Bradford, 1976) and analysed by immunoblotting.

Protein Analysis by Western Blotting

Western blot analysis was performed on ten micrograms of protein from each cell lysate and conditioned media sample using 10% Tris-glycine gels containing 2.6% Bis-acrylamide (Novex, San Diego Calif.). Proteins were blotted onto PVDF paper. Transferred proteins were visualized by staining the membrane with 0.1% Ponceau S solution in 5% acetic acid (Sigma).

Exendin-4 and GLP-1 Mediated Neurite Outgrowth

PC12 cells were grown on 60 mm dishes as above and cultured for four days. During this time neurite outgrowth was quantified daily. Five random fields of cells were evaluated per dish and the proportion of neurite-bearing cells was determined. Approximately 100 cells per field were scored for neurites equal to or greater in length than that of the cell body. A cell was only scored once, although it may have had more than one process per cell.

PC12 cells, when grown in complete media without the presence of neurotrophic compounds, displayed none of the characteristics of neuronal cell types. When exposed to NGF in low serum medium, the cells stopped dividing and developed morphological properties similar to sympathetic neurons. The cells extended long processes, some becoming highly branched with the cell body exhibiting a more flattened appearance than in cells cultured in low serum medium alone.

Treatment with GLP-1 or exendin-4 in low serum medium produced similar effects on differentiation to those induced by NGF. GLP-1 and exendin-4 induced neurites were generally shorter in length, and less branched than neurites generated following treatment with NGF. In contrast, the GLP-1 antagonist, exendin (9-39) in combination with exendin-4 failed to initiate neurite extension.

Daily quantification of neuritic development was also performed. The results shown in FIG. 12 represent the counts taken on day 3 of treatment and are expressed as a percentage of control untreated cells. Growing PC12 cells in the presence of low serum medium alone resulted in 5-10% of the cells extending neuritic projections. Analysis revealed a significant main effect of treatment condition ($F=263.5$, $df=8.89$, $p<0.001$). As expected, NGF treatment significantly induced the neuronal phenotype at the three doses tested here; 10, 30 and 100 ng/ml (all $p<0.01$). For example, the treatment of cells with 10 and 30 ng/ml NGF produced 550 and 720% increase in neurite projections from controls, respectively. Under the same conditions when PC12 cells were treated with exendin-4, a significant neuritic outgrowth was also observed at 1 μg/ml (98% increase relative to untreated, $p<0.05$) and 10 μg/ml (160% increase relative to untreated, $p<0.01$) of the compound. However, the neurite extension with exendin-4 was not as pronounced as that of NGF-treated cells. To determine the synergistic effect of the two compounds, a combination treatment paradigm was tried. When exendin-4 (100 ng/ml) was co-treated with either NGF at 10 ng/ml or 30 ng/ml, a significant increase in neurite outgrowth was observed relative to untreated control cells (596% and 819% increase respectively, both $p<0.01$). Enhancement in neurite outgrowth relative to NGF treatment alone was only significant at 30 ng/ml ($p<0.01$). Similar results were observed with other doses of exendin-4 either alone or in combination with NGF. These data suggest that exendin-4 can initiate differentiation and can enhance NGF-induced differentiation.

Effect of Exendin-4 on NGF-Mediated Cell Death

PC12 cells were grown in complete media (RPMI 1640+5% Fetal bovine serum+10% Horse serum) in the presence/absence of 50 ng/ml NGF or the presence/absence of exendin-4 (1 or 5 mg/ml). Cells were harvested after 4 or 7 days, and subsequently allowed to rejuvenate in regular media for an additional 3 days. On the final day, cells were harvested and a MTT assay was performed to determine the proportion of viable cells. In a second series of experiments (prevention) cells were cultured in the presence of 50 ng/ml NGF and exendin-4 (1 or 5 mg/ml) for 4 or 7 days. Cells were harvested and allowed to rejuvenate as above. In a third series of experiments (rescue) cells were cultured in the presence of 50 ng/ml NGF for 4 days. Exendin-4 at 5 mg/ml was added to the media for an additional 3 days. Cells were harvested on day 7 and allowed to rejuvenate as above.

In a fourth series of experiments (rescue), cells were grown in the presence of NGF. On day 4, 5 mg/ml exendin-4 was added for an additional 3 days. Cells were harvested on day 7 and allowed to rejuvenate as above. Cells were counted in each plate (4 plates/treatment condition) by the trypan blue exclusion method and MTT assays were performed on Days 4 and 7, as described below.

In these experiments NGF withdrawal after 4 days failed to cause massive cell death, and, largely, cells were capable of almost fully rejuvenating. Exendin-4 co-treatment did not show significant effects. Withdrawal of NGF after 7 days of treatment caused a 15-20% reduction in cell viability, and the cells were not capable of fully rejuvenating (FIG. 13, bar 2). In this case exendin-4 co-treatment did not prevent cell death, at either the low (FIG. 13, bar 4) or the high (FIG. 13, bar 6) dose, or when added after 4 days of NGF treatment (FIG. 13, bar 7). However, when exendin-4 treatment was carried out following NGF-withdrawal, revival processes were enhanced. For example, when PC12 cells were cultured in the presence of NGF for 4 days, NGF was withdrawn and exendin-4 added from days 4-7 (FIG. 13, bars 8 and 9), cell survivability reached control values (>95%). This was the case for both the high (5 mg/ml) and the low (1 mg/ml) dose of exendin-4.

MTT Assay

The CellTiter 96® Aqueous One Solution Cell Proliferation Assay Reagent from Promega (Madison, Wis.) was used in a colourimetric procedure for determination of the number of viable cells in a modified MTT assay. The Reagent contains a novel tetrazolium compound [3-(4,5-dimethyl-2-yl)-5-(3 carboxymethoxyphenyl)-2-(4-sulfophenyl)-2H-tetrazolium, inner salt; MTS] and an electron coupling reagent (phenazine ethosulfate; PES). PES has enhanced chemical stability, which allows combination with MTS to form a stable solution. The MTS tetrazolium compound is bioreduced by cells into a coloured formazan product, which is soluble in tissue culture medium. This conversion is presumably accomplished by NADPH or NADH produced by dehydrogenase enzymes in metabolically active cells (Berridge and Tan 1993). Assays are performed by the addition of a small amount of the Reagent directly to cultured wells, incubation for 1-4 hours and subsequent absorbance at 490 nm with a 96-well plate reader. The quantity of formazan product, as measured by the amount of 490 nm absorbance, is directly proportional to the number of living cells in culture. Since the MTS formazan product is soluble in tissue culture medium the present procedure requires fewer steps than procedures that use tetrazolium components such as MTT.

Partial Inhibition of Neurite Outgrowth by a PKA Inhibitor

Differentiated cultures were treated with 50 μM PD98059 or 40 μM LY294002, which inhibit ERK MAPK and PI3-K, respectively, to determine the mechanism of GLP-1 and exendin-4 induced neurite outgrowth. To determine whether cAMP-dependent MAPK phosphorylation was controlled by PKA, GLP-1 and NGF-induced neurites were treated with the PKA specific inhibitor, H89.

Specifically, the cultures were treated for 48 hours with the GLP-1 antagonist, exendin (9-39); with the PI3 kinase inhibitor, LY294002 (40 μM); with the MAP kinase inhibitor, PD98059 (50 μM) or with the PKA inhibitor, H89 (20 μM). Cells were seeded onto 60 mm dishes at approximately $1 \times 10^5$ cells/ml and treated with either 10 nM GLP-1 or 0.3 μM exendin-4 with each of the aforementioned compounds. NGF at 50 ng/ml and forskolin (PKA activator) (20 μM) were used as positive controls in these treatments.

Both PD98059 and LY294002 reduced GLP-1 and exendin-4 induced neurite outgrowth of the cells. Similarly, NGF-induced neuritic extension was reduced following PD98059 and LY294002 treatment. The involvement of both the ERK MAP kinase and the PI3 kinase signaling pathways is thus implicated in GLP-1 and exendin-4 mediated neurite production in PC12 cells. Treatment with H89 demonstrated some inhibitory effects on GLP-1 and NGF-induced neurite outgrowth. These data suggest that PKA is involved in the regulation of the MAP kinase signaling pathway but other signaling pathways are also involved.

Expression of Synaptophysin and Beta-2/NeuroD

To examine the molecular changes that are occurring during GLP-1, exendin-4, or exendin-WOT induced differentiation of PC12cells, the profile of synaptophysin, which is a 37 kDa phosphorylated protein well expressed in the synaptic vesicle membrane, was studied. The synaptophysin monoclonal antibody (Oncogene Research Products, San Diego Calif.), which stains neurosecretory vesicles of PC12 cells, was used. The membranes were blocked with 20 mM Tris, 500 mM NaCl pH 7.4, 1% (w/v) casein (BioRad, San Diego Calif.) at 37° C. for 1 hour. Primary antibody was diluted in block and incubated with the proteins overnight at 4° C. The membrane was vigorously washed with 20 mM Tris pH 7.4, 150 mM NaCl and 0.05% Tween-20 (TBST), three times for 15 minutes at room temperature. The peroxidase-linked secondary antibody in block was incubated with the membrane for 2 hours at room temperature. Peroxidase-linked anti-mouse IgM (Chemicon, Tenecula, Calif.) was used as the secondary antibody against synaptophysin. Excess antibody was washed off with three vigorous washes in TBST prior to incubation in ECL Plus (Amersham, Philadelphia, Pa.) for 5 minutes. The membrane was subsequently exposed to photographic film. Densitometric quantification of the protein bands was performed using Molecular Analyst software (Bio-Rad, Hercules, Calif.).

Western immunoblot analysis of cell lysate samples using the synaptophysin antibody revealed a molecular weight band of approximately 37 kDa. Treatment with NGF, GLP-1 and GLP-1 analogues dramatically reduced the expression of the synaptophysin protein compared to untreated cells. Densitometric quantification of the protein bands showed significant reductions for all treatment conditions relative to untreated (FIG. 14, all p<0.01), which appeared to be dose-dependent. No immunoreactive band was detected in conditioned media samples from PC12 cells.

The high degree of differentiation in PC12 cells as a result of NGF treatment was accompanied by a marked decrease in synaptophysin expression relative to untreated control cells. Nerve growth factor demonstrated dose related changes in cellular synaptophysin expression, producing an approximately 70% maximal decrease relative to control cells. GLP-1 and analogues, which showed similar effects on neuritic extension to NGF-mediated differentiation but to a lesser degree, showed comparatively smaller decreases in synaptophysin expression. Interestingly, NGF and exendin-4 in combination produced a larger decrease in synaptophysin expression than either compound alone, reflecting the additive morphological effects (FIG. 14). Overall, exendin-4 showed a more pronounced induction of differentiation in PC12 cells, in terms of synaptophysin expression, than did either GLP-1 or exendin-4 WOT.

To investigate the role of the transcription factor Beta-2/NeuroD in GLP-1 induced differentiation in PC12 cells, cell lysates were probed with the NeuroD polyclonal antibody (Santa Cruz Biotechnology Inc., Santa Cruz, Calif.). Beta-2/NeuroD plays a major role in both neuronal and pancreatic endocrine development. Expression of NeuroD appears to be transient in sensory and motor neurons of the peripheral nervous system, sensory organs as well as parts of the brain and spinal cord during neuronal differentiation; however detection in the adult brain may suggest a secondary role in mature neurons (Lee et al 1997). Beta-2 expression in pancreatic endocrine cells, the intestine and the brain, activates insulin gene transcription and can induce neurons to differentiate. Mutant mice lacking the functional Beta-2 gene have a striking reduction in the number of insulin-producing beta cells, fail to develop mature islets and as a consequence develop severe diabetes often resulting in perinatal death (Naya et al 1997). Thus, Beta-2/NeuroD is essential for in vivo pancreatic development and neuronal differentiation.

NeuroD production was determined by Western blot analysis using anti-NeuroD antibody as described above for synaptophysin antibody, except peroxidase-linked anti-goat IgG (Santa Cruz Biotechnology Inc.) was used as the secondary antibody. A 43 kDa band, apparent in both untreated and GLP-1 treated PC12 cell lysates was detected, which was increased following GLP-1 treatment. Beta-2/NeuroD expression is increased following treatment with GLP-1, providing further evidence for the neuronal differentiation properties of this insulinotropic polypeptide. As anticipated, cultures exposed to low serum medium alone showed nominal expression of Beta-2/NeuroD. Indeed, Noma et al (1999) have shown that overexpression of NeuroD in transfected PC12 cells induced morphological changes such as neurite-like processes and synapse-like structures, without a differentiating-inducing agent such as NGF.

Demonstration of GLP-1 Receptor Presence in PC12 Cells

PC12 cells were plated onto poly-L-lysine coated glass coverslips in 35 mm culture dishes and grown under standard conditions (as described above). Cells were fixed with 0.25% glutaraldehyde for 30 minutes. Endogenous peroxidase activity was quenched with 0.3% $H_2O_2$ and incubation in the primary polyclonal antibody (dilution factor 1:1500) raised against the N-terminal of the GLP-1 receptor (a gift from Dr. Joel F. Habener, Massachusetts General Hospital, MA) was carried out at room temperature for 1 hour. Visualization used the avidin-biotin peroxidase method with subsequent development in diaminobenzidine dihydrochloride (DAB) following incubation in the biotinylated anti-rabbit IgG secondary antibody.

The presence of GLP-1R-positive immunoreactive staining in PC12 cells confirmed the presence of the GLP-1 receptor. More specifically, staining was on the cell body and to a lesser extent on the neurite terminal. However, not all PC12 cells expressed positive immunoreactive staining to the same degree, although almost all cells appeared positive.

Reverse Transcriptase Polymerase Chain Reaction (RT-PCR)

RT-PCR was performed as a sensitive assay for GLP-1 receptor mRNA. Rat insulinoma cells (RIN cells) were used as a positive control. Total RNA was isolated from PC12 cells using the method of Chomczynski and Sacchi (1987). 2.5 mg RNA was used in our RT-PCR reaction. RT-PCR was undertaken in a volume of 50 ml of buffer containing 50 mM KCl, 10 mM Tris-HCl, 3.5 mM MgCl2), 200 mM dNTP's and 0.4 mM of each rat GLP-1R sense (5' ACAGGTCTCTTCTG-CAACC 3') and antisense (5' AAGATGACTTCATGCGT-GCC 3') oligonucleotide primers (5'- and 3'-ends of the pancreatic GLP-1 receptor sequences). Amplification was undertaken for 30 cycles in the presence of [a-32P]dCTP. Rat islet cells were used as the positive control. RT-PCR products (10 ml) were separated on a 4-20% polyacrylamide gel with appropriate size markers. The gel was subsequently dried under a vacuum at 80° C. for 1 hour and exposed to X-ray film.

RT-PCR products of the expected size for the GLP-1 receptor were obtained. Clear bands at 928-bp in rat islet mRNA and PC12 cell mRNA confirmed the presence of the GLP-1 receptor on PC12 cells.

cAMP Determination

Before cAMP determination, PC12 cells were treated with 33 µg/ml GLP-1 for 3 days. Triplicate cultures were harvested at 5-minute intervals after the onset of treatment for a total period of 30 minutes. Cells harvested at the start of treatment (zero minutes) were used for baseline levels of cAMP. Cyclic AMP was measured according to the method of Montrose-Rafizadeh et al (1997a).

Activation of the GLP-1 receptor has been shown to stimulate adenylyl cyclase, leading to an increase in intracellular cAMP. Cyclic AMP was assayed over 30 minutes following treatment of PC12 cells with 33 mg/ml GLP-1. There was a maximal 1200-fold increase in cAMP levels within 15 minutes of stimulation, which returned to near baseline within 30 minutes. These findings demonstrate the presence and activity of the GLP-1 receptor on PC12 cells.

Toxicity Assay

The potentially toxic effects of exendin-4 were tested in vitro by two methods: LDH assay and trypan blue exclusion method. The LDH assay was performed using a Sigma kit. Conditioned media samples collected at different time intervals following treatments were subjected to a sensitive lactate dehydrogenase (LDH) assay. The LDH assay provided a measure of the number of cells via total cytoplasmic LDH or by membrane integrity as a function of the amount of cytoplasmic LDH released into the medium. The measurement of released LDH was based on the reduction of NAD by the action of LDH. The resulting reduced NAD (NADH) was utilized in the stoichiometric conversion of a tetrazolium dye. The final coloured compound was measured spectrophotometrically. If the cells were lysed prior to assaying the medium, an increase or decrease in cell number resulted in a concomitant change in the amount of substrate converted. This indicated the degree of cytolysis or membrane damage (cytotoxicity) caused by the test material.

There were no significant changes in viable cell numbers following treatment, suggesting our compounds were not toxic to PC12 cells under the conditions studied. See FIG. 15. To determine the integrity of the cell membrane during treatment, LDH levels were measured in the conditioned medium from control and treated cells under the same conditions on day 3, in two separate series of experiments. As expected, LDH levels were elevated relative to the media standards (samples were taken at the start of treatment). However, with the sole exception of 10 ng/ml NGF and 10 µg/ml exendin-4, no dose of any treatment significantly elevated LDH levels beyond control untreated cells. Exendin-4 at 10 µg/ml elevated levels to 1.65-fold that of controls ($p<0.01$) and 10 ng/ml NGF showed a 1.38-fold increase ($p<0.05$).

Cell Turnover in PC12 Cells Determined by Incorporation of Bromodeoxyuridine

To determine whether GLP-1 affects the proliferation of PC12 cells in culture, cell proliferation in low serum medium was assessed by monitoring incorporation of 5'-bromo-2'-deoxy-uridine (BrdU). Immunocytochemistry with an anti-BrdU antibody after labeling was used to identify cells that were actively replicating DNA at the time of labeling. PC12 cells were cultured for 3 days in the presence or absence of 33 µg/ml GLP-1 or 50 ng/ml NGF. 10 µM BrdU was added to the culture medium for 6 hours prior to fixing in 4% paraformaldehyde, to label cellular DNA. The remainder of the method was followed according to the proliferation kit (Roche, Indianapolis, Ind.). Proliferating cells (those that were undergoing DNA replication at the time of BrdU labeling) exhibited dark-staining nuclei with the chromagen reaction. BrdU incorporation was quantitated on days 1, 2 and 3 of treatment. Three dishes for each treatment condition were counted and expressed as the percentage of labeled cells relative to the total number of cells. PC12 cells showed increased incorporation of BrdU on day 1 following treatment with NGF (9% increase relative to untreated) and GLP-1 (18% relative to untreated).

Example 12

Protection and Reversal of Excitotoxic Neuronal Damage by Glucagon-Like Peptide-1 and Exendin-4

The ability of GLP-1 and its long-acting analogue, exendin-4, to protect cultured hippocampal neurons against cell death induced by glutamate, and to attenuate ibotenic acid-induced cholinergic marker deficit in adult rats was tested.

Culture Conditions

Hippocampal neuronal cultures were prepared from 18-day-old embryonic Sprague Dawley rats using methods similar to those described previously (Mattson et al., 1995). Briefly, cells were dissociated by mild trypsination and trituration and plated in Minimal Essential Medium containing 10% FBS and 1% antibiotic solution ($10^4$ U/ml penicillin G, 10 mg/ml streptomycin and 25 µg/ml amphotericin B; Sigma Chemicals, St. Louis, Mo.). Hippocampal neurons were plated at a density of 100,000 cells/ml on 25 mm diameter poly-D-lysine coated glass coverslips. Three hours after plating the media was replaced with serum-free Neurobasal medium containing 1% B-27 supplement (Gibco/Life Technologies, Carlsbad, Calif.).

Immunofluorescence staining for MAP-2 (neurons) and GFAP (astrocytes) showed that more than 98% of the cells were neurons and the remainder were predominantly astrocytes. Cultures were used within 7-10 days of plating.

Binding Studies

Binding studies were performed as described by Montrose-Rafizadeh (1997b). Duplicate hippocampal neuronal cultures were washed in 0.5 ml binding buffer and subsequently incubated in 0.5 ml buffer containing 2% BSA, 17 mg/liter diprotin A (Bachem, Torrance, Calif.), 10 mM glucose, 0.001-1000 nM GLP-1 and 30,000 cpm $^{125}$I-GLP-1 (Amersham Pharmacia Biotech, Little Chalfont, UK), overnight at 4° C. At the end of the incubation the supernatant was discarded, and the cells washed three times in ice-cold PBS and incubated at room temperature with 0.5 ml 0.5M NaOH and 0.1% SDS for 10 min. Radioactivity in cell lysates was measured in an Apec-Series γ-counter (ICN Biomedicals, Inc., Costa Mesa, Calif.). Specific binding was determined as the total binding minus the radioactivity associated with cells incubated in the presence of a large excess of unlabelled GLP-1 (1 µM). The GLP-1 concentration associated with 50% binding, $EC_{50}$, was determined by logit plot analysis.

Figure 16A:
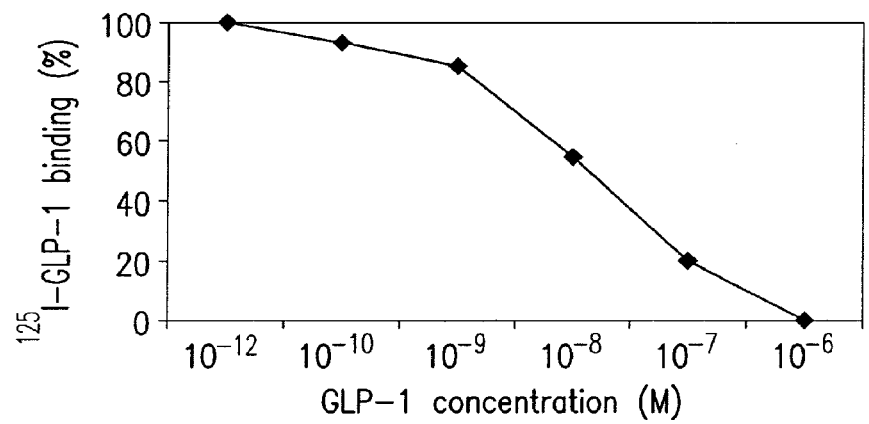

Binding of $^{125}$I-GLP-1 to cultured hippocampal neurons was displaced, concentration-dependently, by unlabelled GLP-1 (FIG. 16A). The concentration of GLP-1 required to displace 50% bound $^{125}$I-GLP-1 was determined by logit plot analysis and required a concentration of 14 nM GLP-1 ($r=-0.999$) in cultured hippocampal neurons.

cAMP Determination

To demonstrate presence of functional GLP-1 receptors, cyclic AMP was measured according to the method of Montrose-Rafizadeh et al., (1997a). Triplicate hippocampal neuronal cell cultures were treated with 10 nM GLP-1 and harvested at 5-minute intervals after the onset of drug treatment for a total period of 30 minutes. Cells harvested at the start of drug treatment (zero minutes) were used for baseline levels of cAMP.

Figure 16B:
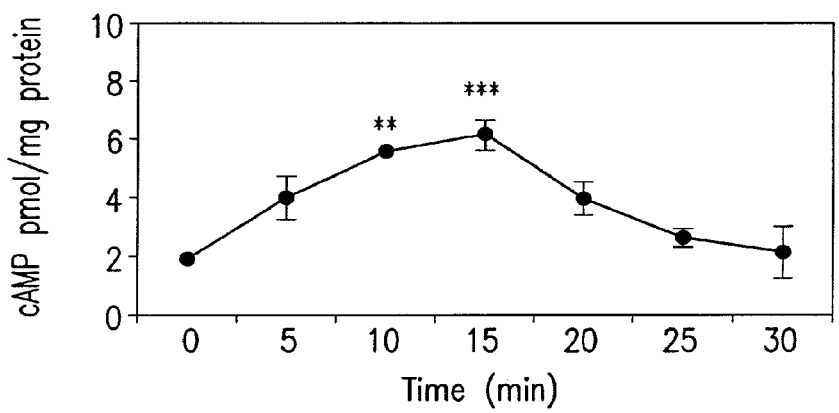

Treatment of cultured hippocampal neurons with 10 nM GLP-1 evoked an increase in cAMP production (FIG. 16B). There was a maximal two- to three-fold increase in cAMP levels within 15 minutes of stimulation, which returned to near baseline within 30 minutes. One-way ANOVA demonstrated significant main effects ($F=9.45$, $df=6.20$, $p<0.001$) of treatment on cAMP production. Subsequent multiple comparisons using Tukey's HSD test revealed significant increases in cAMP production after 10 ($p<0.01$) and 15 ($p<0.001$) min. These data demonstrate that primary hippocampal neurons express functional GLP-1 receptors, making them an appropriate in vitro system in which to study potential protective and trophic effects of these peptides.

Apoptotic Cell Death

The fluorescent DNA binding dye Hoescht 33342 was used to measure apoptotic cell death. Neurons were incubated in Locke's buffer with GLP-1 (10 nM) or exendin-4 (0.3 μM) in the presence of absence of glutamate (10 μM) for 16 h. The concentration of GLP-1 used was based on the $EC_{50}$ value derived from the binding experiment, which was demonstrated to stimulate the release of cAMP, and which induced differentiation without causing cell death in our previous neuronal cell studies. Cells were fixed in a solution of 4% paraformaldehyde in PBS and membranes were permeabilized with 0.2% Trition X-100. Following incubation with Hoechst 33342 (1 μM) for 30 min, nuclei were visualized under epifluorescence illumination (340 nm excitation, 510 nm barrier filter) using a 40× oil-immersion objective. Approximately 200 cells were counted in at least three separate dishes for each treatment condition, and experiments were repeated at least twice. Cells were considered apoptotic if nuclear DNA was fragmented or condensed, whereas cells with nuclear DNA of a more diffuse and uniform distribution, were considered viable. At the time of counting, the investigator was unaware of the identity of the treatment groups. The percentage of cells with condensed or fragmented nuclei was determined in each culture.

Figure 16C:
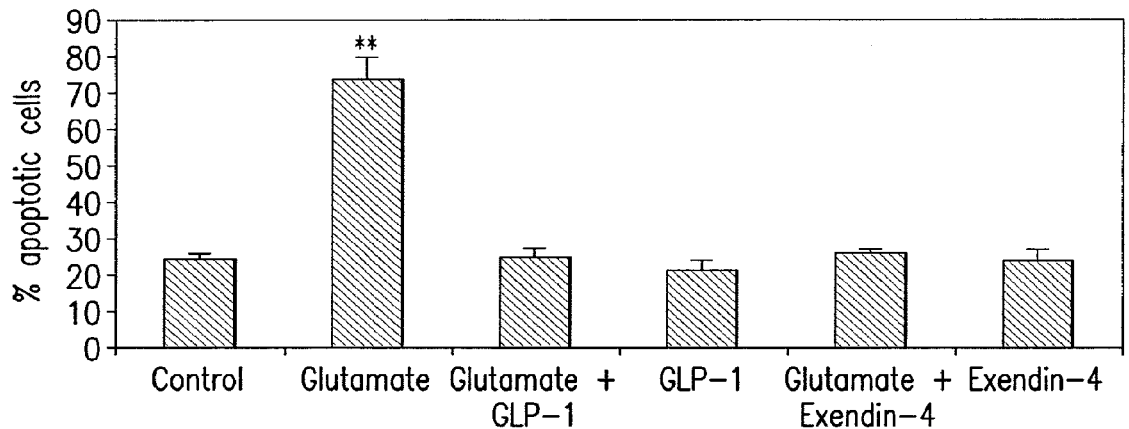
Figure 17A:
Figure 17B:
Figure 17C:
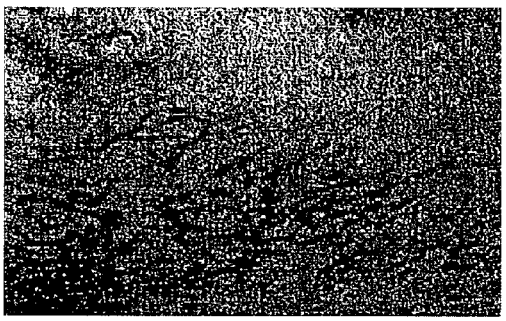
Figure 17D:
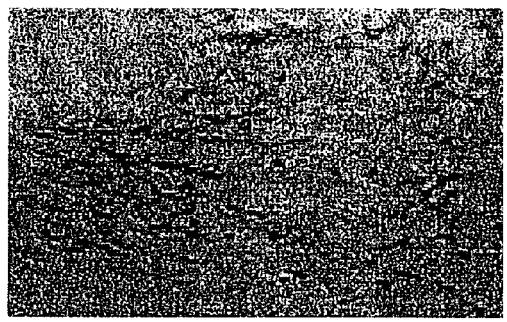
Figure 17E:
Figure 17F:

Primary hippocampal neurons were treated overnight with 10 μM glutamate. Post-fixation, the cells were stained with Hoechst 33342, and the number of apoptotic cells counted. In cells cultured in medium alone, 23% of the neurons exhibited apoptotic nuclei. Glutamate treatment produced 73% apoptosis (FIG. 16C). Concurrent treatment with either 10 nM GLP-1 (24% apoptotic cells) or 0.3 μM exendin-4 (25% apoptotic cells) completely protected against the cell death (FIG. 16B). Treatment with GLP-1 or exendin-4 alone did not produce any increase in the percentage of apoptotic cells (20% and 23%, respectively) beyond that of control levels. The values represent the pooled means of six individual experiments. The percentage of cells undergoing apoptosis as a result of each treatment condition were subjected to ANOVA using StatView statistical software (Cary, N.C.). Following significant main effects, a posteriori comparisons of treatment vs. control were made using Tukey's Honestly Significant Difference (HSD) test, using the pooled ANOVA error term and degrees of freedom. One-way ANOVA demonstrated statistically significant differences in the extent of cell death between each insult ($F=35.31$, $df=5.36$, $p<0.001$), and subsequent multiple comparison using Tukey's HSD test ($Tc=14.91$ and $18.165$) revealed significant increases in the percentage of apoptotic cells following glutamate treatment ($p<0.01$, compared to controls). Concurrent treatment of the cultures with GLP-1 or exendin-4 significantly protected against glutamate-induced cell death (both $p<0.01$, compared to glutamate alone). There were no significant differences between the concurrent glutamate/peptide cultures and controls, demonstrating complete protection of neurons against the effects of glutamate.

Animal and Surgical Procedures

Thirty-five adult male Fischer-344 rats weighing approximately 300 g each were housed under controlled light/dark and temperature conditions with food and water available ad libitum. Rats were anaesthetized with ketamine (90 mg/kg) and acepromazine (0.91 mg/kg). Stereotaxic surgery was carried out as described above. Ibotenic acid dissolved in 0.1 M phosphate-buffered saline (PBS) was infused unilaterally into the left lateral branch of the forebrain bundle; referred to as the basal nucleus by Paxinos & Watson (1998) see references, at 10 μg/μl (0.5 μl, 2 sites). Prior pilot examination of the efficacy of this particular batch of toxin demonstrated that this dose produced a 60% loss of choline acetyltransferase (ChAT)-positive immunoreactivity in the basal forebrain, with a comparable loss of projections to the cortex. A second series of animals receiving infusions of vehicle were used as controls. Each infusion was made over 2.5 min and a further 2.5 min were allowed for diffusion before the cannula was retracted. After two weeks, animals were reanaesethetized and stereotaxically implanted with an intracerebroventricular cannula into the right lateral ventricle (AP=−0.8 mm, L=+1.4 mm, V=−4.0 mm).

The cannulae were attached via a catheter to an osmotic minipump (ALZA Pharmaceuticals, Mountain View, Calif.). Pumps were filled with $2\times10^{-8}$ M GLP-1, $2\times10^{-9}$ M exendin-4 or vehicle (artificial cerebrospinal fluid). Both peptides were diluted in vehicle. The pumps were set to deliver 0.25 μl/h over 14 days (total of 5.54 ng GLP-1 at 0.8 nM/kg/min and 0.7 ng exendin-4 at 0.08 nM/kg/min). The brain infusion kits were assembled 5-6 h prior to implantation, and left in sterile saline at 37° C. The minipumps were inserted into a subcutaneous pocket between the shoulder blades, the wounds sutured and the animals allowed to recover. Animals receiving infusions of GLP-1 or exendin-4, became modestly aphagic and adipsic, as a result of the insulinotropic nature of the peptides, which resulted in a slight drop in body weight. This was recouped within 3-4 days with the administration of twice daily fluids (0.9% saline) and soft diet, and by the time of sacrifice there were no differences in body weight between the groups. On expiry of the minipumps (14 days), animals were terminally anaesthetized 0.1 mg/kg sodium pentobarbitone and transcardially perfused with 100-150 ml PBS (pH 7.4) followed by 250-350 ml 4% paraformaldehyde solution in PBS, PBS, at a constant pressure of 100 mm Hg over a period of 15-20 min. The brains were taken for immunocytochemical assessment and quantification of the lesion-induced damage and any resulting effects of peptide infusion on the cholinergic contingent of the basal forebrain.

Immunohistochemistry

Adjacent coronal brain sections were taken at 40 μm thickness, through the lesion area, and processed free-floating for ChAT; using the polyclonal goat anti-ChAT antibody at 1:100 dilution (Chemicon, International Inc., Temecula, Calif.), and glial fibrillary acidic protein (GFAP); using the polyclonal rabbit anti-GFAP antibody at 1:750 dilution (Chemicon). Visualization of positive immunoreactivity was carried out using an avidin-biotin/horse radish peroxidase protocol. In addition, one series of sections were stained for acetylcholinesterase (AChE) activity, as a histochemical marker for cholinergic neurons of the basal forebrain using a modified method by Geula and Mesulam, 1989. An additional series of sections were mounted onto gelatin-coated slides and stained with cresyl violet to visualize cell bodies.

ChAT-positive immunoreactive cell bodies in the forebrain area were visualized under ×100 magnification and manually counted on both sides. The raw counts were corrected with the Abercrombie (1946) formula for an estimate of the total number of cell bodies in the area. Characterization of the cell loss in the basal nucleus as a result of the ibotenic acid lesion, was made by comparison of left (lesion side) relative to right (infusion side) counts, and the data presented as the percent change. The animal names were coded such that cell counts were formally conducted blind to the experimental condition. Differences were subjected to analysis of variance, and a posteriori comparisons using Tukey's HSD test as above. Significance was accepted at $p<0.05$ for all statistical analyses.

Ibotenic Acid Induced Cholinergic Marker Deficit

Choline acetyltransferase immunoreactivity was used as a marker for cholinergic neurons throughout the basal forebrain. The ChAT antibody stained numerous large multipolar neurons, with a similar size and distribution to the acetylcholinesterase (AChE) positive cells. The immunocytochemical staining had low background and provided a clear picture of the cell morphology (FIG. 17). Injection of ibotenic acid with subsequent infusion of vehicle resulted in a substantial (43%) loss of ChAT-immunoreactive neurons (FIG. 18, bar 4) over an approximately 1 mm radius from the injection site in the left basal nucleus. The sham-operated control group receiving vehicle infusion, showed an increase in the percentage of ChAT-positive cell bodies in the left basal nucleus relative to the right basal nucleus (FIG. 18, bar 1). Ibotenate lesioned animals that received GLP-1 or exendin-4 infusions resulted in a decreased loss of ChAT-immunoreactive cell bodies in the left basal nucleus relative to those lesioned animals that received vehicle infusion. More specifically, infusion of exendin-4 produced a decrease in the loss of ChAT-immunoreactive cell bodies in the left basal nucleus, from 43% as was apparent following vehicle infusion, to just 24% below that of the right basal nucleus (FIG. 18, bar 5). Furthermore, GLP-1 infusion resulted in more striking reversal effects, decreasing the loss of ChAT-positive immunoreactive cell bodies in the left basal nucleus to just 6% below that of the right basal nucleus (FIG. 18, bar 6). Standard ANOVA demonstrated an overall significant effect of treatment condition ($F=21.363$, $df=5.28$, $p<0.001$). Multiple comparisons of peptide vs. vehicle treatment ($Tc=14.14$ and $19.71$) revealed significant improvements in ChAT-immunoreactivity in the left basal nucleus following infusion of exendin-4 ($p<0.05$) and GLP-1 ($p<0.01$) after an ibotenic acid lesion. Although infusion of GLP-1 following an ibotenic acid lesion decreased the ChAT-positive cell loss in the left basal nucleus to produce near equal values with the right side, the overall percent difference was still significantly lower than the sham vehicle group ($p<0.001$). This is likely due to the perceptible increase in ChAT-immunoreactivity in the sham group receiving vehicle infusion (FIG. 18, bar 1).

Separating the left and right ChAT-positive immunoreactive neuronal counts for the sham vehicle group (Table 6) revealed a significant difference between left ($586\pm32$) and right ($478\pm40$) basal nuclei ChAT-positive cell counts ($p<0.01$). Pressure effects from cannula implantation and treatment delivery may account for the apparent decrease in ChAT-immunoreactivity in the right basal nucleus. These observations suggest that any disturbance of tissue integrity, however mild or non-specific, can produce a functional disruption of ChAT immunoreactivity. Furthermore, such effects may account for the lower than anticipated percent loss in ChAT-positive immunoreactivity in the ibotenic acid group receiving vehicle infusion (FIG. 18, bar 4). To examine this further, rather than comparing 'within' groups (i.e., left vs. right), 'between' groups comparisons were performed of left basal nucleus counts ($F=6.136$, $df=5.28$, $p<0.001$; Table 6) for the sham aCSF and ibotenic acid aCSF groups ($586\pm32$ and $260\pm28$, respectively). The between group comparisons revealed a 56% loss in ChAT-immunoreactivity. These data indicate that non-specific damage in the right basal nucleus produced decreases in the number of ChAT-immunoreactive cell bodies, affecting the overall percent loss when comparisons were made within individual experimental groups. In addition, there was no significant difference between groups when right basal nucleus ChAT-positive cell counts were analysed separately ($F=0.512$, $df=5.28$, $p>0.05$, Table 6), implying that such disruption of tissue integrity affected all experimental groups equally.

TABLE 6

Abercrombie corrected ChAT-positive cell counts in the basal nucleus.

| Group (Number of animals) | Left basal nucleus (lesion side) [F = 6.136, df = 5.28, p < 0.001] | Right basal nucleus (infusion side) [F = 0.512, df = 5.28, p > 0.05] |
| --- | --- | --- |
| Sham aCSF (n = 4) | 586 ± 32 | 478 ± 40** |
| Sham exendin-4 (n = 5) | 417 ± 49 | 416 ± 52 |
| Sham GLP-1 (n = 6) | 517 ± 50 | 499 ± 41 |
| Lesion aCSF (n = 6) | 260 ± 28 | 461 ± 54*** |
| Lesion exendin-4 (n = 7) | 357 ± 35 | 468 ± 30*** |
| Lesion GLP-1 (n = 6) | 404 ± 59 | 423 ± 45 |

Example 13

Glucagon-Like Peptide-1 Decreases Amyloid-β Peptide (Aβ) Production and Protects Neurons Against Death Induced by Aβ and Iron The protective effects of GLP-1 and/or exendin-4 following cell death induced by Aβ1-42 or Fe2+, and the effects of GLP-1, exendin-4 and exendin-4 WOT on the processing of βAPP between secreted and intracellular forms in vitro, and ultimately on levels of the Aβ peptide in vivo in control mice were tested.

Culture Conditions

PC12 cells were cultured in RPMI 1640 supplemented with 10% heat-inactivated horse serum, 5% heat-inactivated fetal bovine serum (FBS), and 25 mM Hepes buffer as described elsewhere (Lahiri et. al., 2000). All culture media and sera were obtained from MediaTech Inc. (Herndon, Va.). Cells were seeded at approximately $2.0\times10^6$ cells/60-mm dish, on cultureware coated in rat-tail collagen (Roche Molecular Biochemicals, Indianapolis, Ind.). Treatments in triplicate began 24 h after seeding, once cells were well attached. The medium was aspirated, and 3 ml of fresh low serum media containing 0.5% FBS with the appropriate compound(s) was added. Cells were treated with GLP-1 (3.3, 33, and 330 μg/ml) (Bachem, Torrence, Calif.), and two GLP-1 analogues, exendin-4 (0.1, 1.0 and 10 μg/ml) and exendin4-WOT (0.1 and 1.0 μg/ml). Treatment of PC12 cells with NGF (5, 10, 25 and 50 ng/ml) (Promega, Madison, Wis.) was used as a positive control. In addition, 5 ng/ml NGF and 0.1 μg/ml exendin-4 were added simultaneously in combination. Exendin-4 and its analogue exendin 4-WOT were synthesized and assessed to be >95% pure by high-performance liquid chromatography analysis.

Toxicity Assay

Treatment induced cellular toxicity was examined by assay of secreted lactate dehydrogenase (LDH) levels in the conditioned media from both treated and untreated PC12 cells (using the LDH kit from Sigma, St. Louis, Mo.). As expected, LDH levels were elevated relative to the media standards taken at the start of drug treatment (FIG. 19A). Analysis of variance demonstrated an overall significant effect of treatment on LDH secretion ($F=2.22$, $df=11.35$, $p<0.001$). Subsequent multiple a posteriori comparisons with controls using Tukey's HSD test ($Tc=0.42$ and $0.51$) revealed a single significant increase in LDH secretion following 10 μg/ml Ex4 treatment (1.65-fold elevation; $p<0.01$). The possibility of toxicity as a result of treatment with GLP-1 and analogues, at the doses and time points used; with the exception of 10 µg/ml exendin-4, can be ruled out. This was further substantiated by the cell counts (after staining with trypan blue) carried out before and after GLP-1 treatment, which did not demonstrate any significant change in total cell number.

Western Analysis

Following treatment for three days, conditioned media and cell lysates (prepared as described above) from untreated (low serum medium alone) and treated PC12 cells were subjected to Western immunoblot analysis using the monoclonal antibody, 22C11 (Roche Molecular Biochemicals, Indianapolis, Ind.). The antibody, raised against E. Coli-made βAPP whose epitope region has been assigned to residues 66-81 in the ectoplasmic cysteine-containing domain, recognizes all mature forms of βAPP found in cell membranes, as well as carboxyl-truncated soluble forms secreted into conditioned media and βAPP-like proteins (APLP). Visualization of the immunoreactive product was carried out by chemiluminescence, hence molecular weight markers were not visible on the photographic film. Molecular weight identification of the luminescent product was achieved by superimposing the standard molecular weight markers visible on the PVDF membrane. Densitometric quantification of the protein bands was performed using NIH image.

Western immunoblots of cell lysates from treated or untreated cells, revealed multiple higher molecular weight protein bands (100-140 kDa) that likely represent different isoforms of mature βAPP (βAPP695-βAPP770) and/or their post-translationally modified derivatives. Secreted APP was detected in conditioned media from treated and untreated cells, as a 110-120 kDa protein band, likely representing derivatives of βAPP generated by either α- or β-secretase. The differences observed in the profile of immunoreactive bands in the immunoblots of intracellular proteins, was due neither to the unequal loading of proteins into the gel nor to the uneven transfer of proteins onto the membrane, as demonstrated by equal β-actin immunoreactive staining (using the polyclonal β-actin antibody raised against a specific region at the carboxyl terminus of human β-actin; Santa Cruz Biotechnology, Santa Cruz, Calif.) on the same blots. A visual reaction product was produced directly on the PVDF membrane using a biotinylated secondary antibody. The standard molecular weight marker was therefore visible, and confirmed β-actin as a single 42 kDa protein band. Equivalent amounts of total proteins were loaded in each lane of the gel and the efficiency of the electrophoretic transfer was monitored by staining the membranes with 0.1% Ponceau S in 5% acetic acid.

Densitometric quantification of the βAPP and sAPP blots are shown in FIGS. 19B and C, respectively. One-way analysis of variance of the quantified βAPP levels (top two high molecular weight bands) demonstrated overall significant effects of treatment (F=2.24; df=11.34; p<0.001). Multiple comparisons with controls were conducted using Tukey's HSD test (Tc=47.0 and 55.75) and revealed increases in intracellular levels of βAPP following treatment with both doses of NGF; 5 ng/ml (FIG. 19B, bar 1; p<0.01) and 10 ng/ml (FIG. 19B, bar 2; p<0.01). In contrast to NGF, GLP-1 and analogues significantly decreased intracellular levels of βAPP (FIG. 19B; 10 ng/ml Ex4, bar 5 (p<0.01), 1.0 µg/ml Ex4-WOT, bar 10 (p<0.01), 3.3 µg/ml GLP-1, bar 11 (p<0.01), 33 µg/ml GLP-1, bar 12 (p<0.05) and 330 µg/ml GLP-1, bar 13 (p<0.01). The combination treatment of 5 ng/ml NGF and 0.1 µg/ml Ex4 significantly increased intracellular βAPP levels relative to untreated cells (FIG. 19B, bar 6; p<0.01).

Analysis of the quantified secreted soluble derivatives of βAPP protein detected in the conditioned medium, revealed overall significant effects of treatment (F=2.22, df=11.35, p<0.001). Subsequent multiple comparisons (Tc=20.11 and 23.91) revealed both doses of NGF treatment resulted in a significant increase in sAPP (5 ng/ml and 10 ng/ml (both p<0.01); FIG. 19C, bars 1-2). Following a similar pattern to intracellular βAPP levels, all doses of GLP-1 (3.3 µg/ml (p>0.05), 33 µg/ml (p<0.01) and 330 µg/ml (p<0.01); FIG. 19C, bars 9-11), Ex4 (0.1 µg/ml, 1.0 µg/ml and 10 µg/ml (all p<0.01); FIG. 19C, bars 3-5) and Ex4-WOT (0.1 µg/ml and 1.0 µg/ml (both p<0.01); FIG. 19C, bars 7-8) produced decreases in detectable levels of sAPP in conditioned media. The combination NGF and Ex4 treatment (FIG. 19C, bar 6) failed to produce any significant change in sAPP levels from that of the control cells.

To investigate whether the decline in βAPP levels following GLP-1 treatment could be extrapolated to a decline in secreted Aβ1-40 levels, conditioned media samples were assayed for Aβ1-40. We have previously demonstrated very low basal levels of Aβ1-42 secretion in PC12 cells, and generally any detectable treatment induced effects do not reach significance. In addition, the predominant Aβ peptide secreted is Aβ1-40 and in similar studies using neuroblastoma cells (Lahiri et. al., 1998) Aβ1-40 levels were reflective of effects on Aβ1-42, making it unnecessary to look for Aβ1-42 specific changes. Quantified Aβ1-40 levels were subjected to one-way analysis of variance, which demonstrated significant overall effects of treatment (F=2.22, df=11.35, p<0.001). Multiple comparisons using Tukey's HSD test (Tc=69.91 and 83.13) revealed significant increases in Aβ1-40 levels following treatment with NGF alone (both p<0.01) or in combination with exendin-4 (p<0.01). Treatment with GLP-1, exendin-4 or exendin-4 WOT alone did not significantly alter levels of Aβ1-40 production from that of the control cells.

Whole brain homogenates were assayed for Aβ1-40 levels following intracerebroventricular infusions of GLP-1, exendin-4, NGF or vehicle in normal control mice. Animals were housed under controlled light/dark and temperature conditions with food and water available ad libitum. Lean db+/db+ control male mice (n=24) were anaesthetized with 50 mg/kg pentobarbitone and placed in a stereotaxic surgical frame with mouse adaptor (David Kopf Instruments, Tujunga, Calif.) using temporal bone cup holders. Bilateral infusions of GLP-1 (3.3 µg; n=3 and 6.6 µg; n=4), exendin-4 (0.2 µg; n=3), NGF (2 µg; n=5) or vehicle (artificial cerebrospinal fluid; n=9) were made into the lateral ventricles (AP=−0.2 mm, L=±1.0 mm, V=−2.5 mm), at 0.25 µl/min over 4 minutes. An additional 4 minutes was allowed for diffusion before the cannula was retracted and the animal sutured and allowed to recover. After 48 h all animals were sacrificed by cervical dislocation, the brains removed and rapidly frozen in liquid nitrogen. Brains were pulverized and stored at −80° C. prior to assaying for Aβ levels.

Aβ Assay

Equivalent volumes of conditioned media and whole brain homogenate were assayed for Aβ1-40 using a sandwich ELISA (Suzuki et. al., 1994). The monoclonal antibody BAN50 (raised against Aβ1-16) was used as the capture antibody for all species of Aβ (Aβ1-40 and Aβ1-42), and the monoclonal antibody BA27 was used to specifically detect Aβ1-40 levels. Levels of Aβ1-40 were expressed in pM concentrations for conditioned media samples and fmol/g for the mouse brain homogenates, as deduced from the appropriate standard curve run in parallel with the assay.

All treatments reduced levels of Aβ1-40 compared to vehicle (FIG. 20). Multiple comparisons following significant main effects of treatment (F=10.577, df=4.19, p<0.001) demonstrated Aβ1-40 levels were reduced significantly following 6.6 µg GLP-1 (36%, p<0.01) and 2 µg NGF (40%, p<0.01) treatment. All other comparisons failed to reach significance; 3.3 µg GLP-1 (16%), 0.2 µg exendin-4 (23%) (Tc=139.00 and 172.34, using a harmonic mean correction for unequal group sizes)

Primary Hippocampal Cell Culture

Hippocampi were removed from embryonic day 18 Sprague-Dawley rats, and cells were dissociated by mild trypsination and trituration and seeded onto polyethyleneimine-coated plastic 35 mm diameter dishes at a density of approximately 150 cells/mm$^2$ of culture surface. Cultures were maintained in Neurobasal medium containing B-27 supplements (Gibco BRL, Carlsbad, Calif.), 2 mM L-glutamine, 1 mM Hepes and 0.001% gentamicin sulfate (Sigma, St. Louis, Mo.) in a 6% $CO_2$/94% room air atmosphere at 37° C. When maintained under these conditions, the hippocampal cultures consisted of approximately 95% neurons and 5% astrocytes as determined by immunostaining with antibodies against the neuronal antigen NeuN and the astrocyte protein glial fibrillary acidic protein. Aβ1-42 was purchased from Bachem (Torrance, Calif.) and was prepared as a 1 mM stock solution in sterile water. $FeSO_4$ was prepared as a 200 µM stock in sterile water. GLP-1 and exendin-4 were prepared as 500× stocks in saline.

Neuronal survival was quantified as described previously (Mark et. al., 1997). Briefly, viable neurons in premarked fields (10× objective) were counted before experimental treatment and at specified time points thereafter. Hippocampal neurons were pretreated with GLP-1 (0, 1, 5, 10 and 20 nM) or exendin-4 (0, 50, 100, 200 and 500 nM) for 2 hours. Cultures were then exposed to 2 µM Aβ (1-42) or 1 µM $Fe^{2+}$ for 24 hours. Neurons with intact neurites of uniform diameter and a cell body with a smooth round appearance were considered viable, whereas neurons with fragmented neurites and vacuolated soma were considered non-viable. The counting was done without knowledge of culture treatment history.

Exposure of cultured hippocampal cells to Aβ1-42 or to iron (which induces hydroxyl radical production and membrane lipid peroxidation) resulted in the death of 55-75% of the neurons during a 24 h time period. To determine if GLP-1 or exendin-4 could protect neurons against cell death induced by Aβ1-42 and/or $Fe^{2+}$, cells were pretreated with increasing concentrations of GLP-1 and exendin-4, and then exposed to Aβ1-42 or $Fe^{2+}$. GLP-1 protected neurons against death induced by Aβ1-42 and $Fe^{2+}$ with a maximum effect occurring with 10 nM GLP-1. Exendin-4 also protected neurons against death induced by Aβ1-42 and $Fe^{2+}$, but was less potent, with a maximum effect occurring with 200 nM exendin-4.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Abercrombie M (1946) Estimation of nuclear population from microtome sections. *Anat Rec* 94:239-247.

Bressler et al. "Pharmacological regulation of blood glucose levels in non-insulin dependent diabetes," *Arch. Int. Med.* 157:836-848 (1997)

Calvo et al. "Structural characterization by affinity cross-linking of glucagon-like peptide-1 (7-36) amide receptor in rat brain," *J. Neurochem.* 64(1):299-306 (1995)

Campos et al. "Divergent tissue-specific and developmental expression of receptors for glucagon and glucagon-like peptide-1 in the mouse," *Endocrinology* 134:2156-64 (1994)

Chen et al. "Tissue-specific expression of unique mRNAs that encode pro-glucagon-derived peptides or exendin-4 in the lizard," *J. Biol. Chem.* 272: 4108-4115 (1997)

De Ore et al. "The effect of GLP-1 on insulin release in young and old rats in the fasting state and during an intravenous glucose tolerance test," *J. Gerontol.* 52:B245-249 (1997)

Drucker et al. "Glucagon-like peptide I stimulates insulin gene expression and increases cyclic AMP levels in a rat islet cell line," *Proc. Natl. Acad. Sci.* 84:3434-3438 (1987)

Elahi et al. "The insulinotropic actions of glucose-dependent insulinotropic polypeptide (GIP) and glucagon-like peptide-1 (7-36) in normal and diabetic subjects," *Regul. Pep.* 51:63-74 (1994)

Fehmann et al. "Cell and Molecular Biology of the Incretin Hormones Glucagon-Like Peptide-I and Glucose-Dependent Insulin Releasing Polypeptide," *Endocrine Rev.* 16:390-410 (1995)

Fehmann et al. "Insulinotropic hormone glucagon-like peptide-1 (7-37) stimulation of proinsulin gene expression and proinsulin biosynthesis in insulinoma βTC-1 cells", *Endocrinology* 130: 159-166 (1992)

Geula and Mesulam "Cortical cholinergic fibers in aging and Alzheimer's disease: a morphometric study," *Neuroscience.* 33:469-81 (1989)

Ghazzi et al. "Cardiac and glycemic benefits of troglitazone treatment in NIDDM," *Diabetes* 46: 433-439. Care. 15: 270-276 (1997)

Goke et al. "Cardiac and Glycemic Benefits of Troglitazone Treatment in NIDDM," *Diabetes* 46:433-439 (1993)

Goke et al. "Distribution of GLP-1 binding sites in the rat brain: evidence that exendin-4 is a ligand of brain GLP-1 binding sites, *Eur. J. Neurosci* 7:2294-2300 (1995)

Goke et al. "Exendin-4 is a high potency agonist and truncated exendin-4 (9-39)-amide in an antagonist at the GLP-1 (7-36)-amide receptor of insulin-secreting-cells," *J. Biol. Chem.* 268:19650-19655 (1993)

Greig N et al. "Once daily injection of exendin-4 to diabetic mice achieves long-term beneficial effects on blood glucose concentrations." *Diabetologia* 42:45-50, (1999).

Gross and Meienhofer (eds.) "The Peptides: Analysis, Synthesis," Biology 3: Protection of Functional Groups in *Peptide Synthesis*, Academic Press, N.Y. (1981)

Gutniak et al. "Antidiabetogenic effect of glucagon-like peptide-1 (7-36) amide in normal subjects and patients with diabetes mellitus," *N. Engl. J. Med.* 326:1316-1322 (1992)

Jin et al. "Distribution of glucagonlike peptide I (GLP-I), glucagon, and glicentin in the rat brain: an immunocytochemical study," *J. Comp. Neurol.* 271:519-32. (1988)

Lahiri D K, Farlow M R, Hintz N, Utsuki T and Greig N H. 2000 Cholinesterase inhibitors, beta-amyloid precursor protein and amyloid beta-peptides in Alzheimer's disease *Acta Neurol Scand Suppl* 176:60-67.

Mark R J, Pang Z, Geddes J W, Uchida K and Mattson M P. 1997 Amyloid beta-peptide impairs glucose transport in hippocampal and cortical neurons: involvement of membrane lipid peroxidation *J Neurosci* 17:1046-1054.

Mattson M P, Lovell M A, Furukawa K et al., (1995) Neurotrophic factors attenuate glutamate-induced accumulation of peroxides, elevation of intracellular Ca2+ concentration, and neurotoxicity and increase antioxidant enzyme activities in hippocampal neurons. *J Neurochem* 65(4): 1740-1751.

Moceri et al. "Early-life risk factors and the development of Alzheimer's disease," *Neurology* 54:415-420 (2000)

Montrose-Rafizadeh C, Wang Y, Janczewski A M et al., (1997a) Overexpression of glucagon-like peptide-1 receptor in an insulin-secreting cell line enhances glucose responsiveness. *Mol Cell Endocrinol* 130(1-2):109-117.

Montrose-Rafizadeh et al. "High potency antagonists of the pancreatic glucagon-like peptide-1 receptor," *J. Biol. Chem.* 272:21201-21206 (1997b)

Montrose-Rafizadeh et al. "Incretin hormones regulate glucose dependent insulin secretion in RIN 1046-38 cells: mechanisms of action," *Endocrinology* 135:589-594 (1994)

Nathan et al. "Insulinotropic action of glucagonlike peptide-I-(7-37) in diabetic and nondiabetic subjects," *Diabetes Care* 15:270-276 (1992)

Nauck et al. "Preserved incretin activity of Glucagon-like peptide 1 (7-36) amide but not of synthetic human gastric inhibitory polypeptide in patients with Type-2 diabetes mellitus," *J. Clin. Invest.* 91: 301-307 (1993)

Nauck et al. "Normalization of fasting hyperglycemia by exogenous glucagon-like peptide-1 (7-36) amide in type II (non-insulin dependent) diabetic patients," *Diabetologia* 36:741-744 (1993)

Naya et al. "Diabetes, defective pancreatic morphogenesis, and abnormal enteroendocrine differentiation in BETA2/neuroD-deficient mice," *Genes Dev.* 11:2323-2334 (1997)

Orskov "Glucagon-like peptide-1, a new hormone of the entero-insular axis," *Diabetologia* 35: 701-711 (1992)

Ott et al. "Diabetes mellitus and the risk of dementia: The Rotterdam Study," *Neurology* 53:1937-42 (1999)

Paxinos and Watson. "The rat brain in stereotaxic coordinates", Academic Press, NSW Australia (1998).

Perry et al. "Behavioural, histological and immunocytochemical consequences following 192 IgG-saporin immunolesions of the basal forebrain cholinergic system," *Brain Res. Bull.* 54:29-48 (2001)

*Remington's Pharmaceutical Sciences* (Martin, E. W. (ed.) latest edition Mack Publishing Co., Easton, Pa.)

Ritzel et al. "Pharmacokinetic, insulinotropic, and glucagonostatic properties of GLP-1 [7-36 amide] after subcutaneous injection in healthy volunteers. Dose-response-relationships," *Diabetologia.* 38:720-725 (1995)

Sambrook et al., *Molecular Cloning, a Laboratory Manual*, (2nd ed.) Vol. 1-3 Cold Spring Harbor Laboratory Press, NY (1989)

Satoh et al. "Characterization of human and rat glucagon-like peptide-1 receptors in the neurointermediate lobe: lack of coupling to either stimulation or inhibition of adenylyl cyclase," *Endocrinology* 141:1301-9 (2000)

Shughrue et al. "Glucagon-like peptide-1 receptor (GLP1-R) mRNA in the rat hypothalamus," *Endocrin.* 137(11):5159-62 (1996)

Suzuki N, Cheung T T, Cai X D, Odaka A, Otvos L, Jr, Eckman C, Golde T E and Younkin S G. 1994 An increased percentage of long amyloid beta protein secreted by familial amyloid beta protein precursor (beta APP717) mutants *Science* 264:1336-1340.

Thorens et al. "Cloning and functional expression of the human islet GLP-1 receptor. Demonstration that exendin-4 is an agonist and exendin(9-39) an antagonist of the receptor," *Diabetes* 42:1678-1682 (1993)

Thorens et al. "Glucagon-like peptide-1 and the control of insulin secretion in the normal state and in NIDDM," *Diabetes* 42:1219-1225 (1993)

U.S. Pat. No. 3,710,795 "Drug-Delivery device with Stretched, Rate-Controlling Membrane," Higuchi et al. (Jan. 16, 1973)

Wang et al. "GIP regulates glucose transporters, hexokinases, and glucose-induced insulin secretion in RIN 1046-38 cells," *Moll. Cell. Endo.* 116:81-87 (1996)

Wang et al. "Glucagon-like peptide-1 affects gene transcription and messenger ribonucleic acid stability of components of the insulin secretory system in RIN 1046-38 cells," *Endocrinology* 136:4910-4917 (1995)

Wei et al. "Tissue-specific expression of the human receptor for glucagon-like peptide-I: brain, heart and pancreatic forms have the same deduced amino acid sequences," *FEBS Lett* 358(3):219-224 (Jan. 30, 1995)

Wilms et al. "Gastric emptying, glucose responses, and insulin secretion after a liquid test meal: effects of exogenous glucagon-like peptide-1 (7-36) amide in Type II (non-insulin-dependent) diabetic patients," *J. Clin. Edocrinol. Metab.* 81:327-332 (1996)

What is claimed is:

1. A method of treating a subject with a neurodegenerative disease or of reducing one or more symptoms of a neurodegenerative disease in a subject in need thereof, comprising administering to the subject a therapeutically effective amount of a polypeptide comprising GLP-1, exendin-4, or a therapeutically effective GLP-1 or exendin-4 analogue, wherein the polypeptide binds to and activates a receptor that binds GLP-1, exendin-4, or both, and wherein the neurodegenerative disease is traumatic brain injury or spinal cord injury.

2. The method of claim 1, wherein the neurodegenerative disease is traumatic brain injury.

3. The method of claim 1, wherein the neurodegenerative disease is spinal cord injury.

4. The method of claim 1, wherein the polypeptide is insulinotropic.

5. The method of claim 1, wherein the polypeptide is longer acting than GLP-1.

6. The method of claim 1, wherein the polypeptide has a greater binding affinity for the GLP-1 receptor than does GLP-1.

7. The method of claim 1, wherein the polypeptide is selected from the group consisting of SEQ ID NOs: 9, 42-48, and 50-52.

8. The method of claim 1, wherein the polypeptide comprises GLP-1 or a therapeutically effective GLP-1 analogue.

9. The method of claim 8, wherein the polypeptide is selected from the group consisting of SEQ ID NOs: 5-6 and 8.

10. The method of claim 8, wherein the polypeptide is insulinotropic.

11. The method of claim 8, wherein the polypeptide is longer acting than GLP-1.

12. The method of claim 8, wherein the polypeptide has a greater binding affinity for the GLP-1 receptor than does GLP-1.

13. The method of claim 1, wherein the polypeptide comprises exendin-4 or a therapeutically effective exendin-4 analogue.

14. The method of claim 13, wherein the polypeptide is selected from the group consisting of SEQ ID NOs: 10-12 and 33.

15. The method of claim 13, wherein the polypeptide is insulinotropic.

16. The method of claim 13, wherein the polypeptide is longer acting than GLP-1.

17. The method of claim 14, wherein the polypeptide has a greater binding affinity for the GLP-1 receptor than does GLP-1.

18. A method for treating a neurodegenerative disease in a human in need thereof, comprising administering a therapeutically effective amount of exendin-4 to the human to treat the neurodegenerative disease, wherein the neurodegenerative disease is traumatic brain injury or spinal cord injury.

19. The method of claim 18, wherein the neurodegenerative disease is traumatic brain injury.

20. The method of claim 18, wherein the neurodegenerative disease is spinal cord injury.

* * * * *